United States Patent
Blanc et al.

(10) Patent No.: US 8,992,912 B2
(45) Date of Patent: Mar. 31, 2015

(54) METHODS OF USE FOR ANTIBODIES THAT SPECIFICALLY BIND TO THE EPHA2 RECEPTOR

(71) Applicant: Sanofi, Paris (FR)

(72) Inventors: Veronique Blanc, Paris (FR); Claudia Fromond, Paris (FR); Fabienne Parker, Paris (FR); Jiawen Han, Paris (FR); Daniel Tavares, Natick, MA (US); Chonghui Zhang, Brookline, MA (US); Min Li, Sudbury, MA (US); Xiao-Mai Zhou, Watertown, MA (US); Michel Streuli, Brookline, MA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/787,293

(22) Filed: Mar. 6, 2013

(65) Prior Publication Data
US 2013/0302316 A1    Nov. 14, 2013

Related U.S. Application Data

(63) Continuation of application No. 12/373,574, filed as application No. PCT/IB2007/003074 on Jul. 13, 2007, now Pat. No. 8,460,667.

(30) Foreign Application Priority Data

Jul. 18, 2006 (EP) .................................... 06291160

(51) Int. Cl.
*A61K 39/395* (2006.01)
*C07K 16/00* (2006.01)
*C07K 16/18* (2006.01)
*C07K 16/28* (2006.01)
*C07K 16/30* (2006.01)
*A61K 39/00* (2006.01)

(52) U.S. Cl.
CPC ............ *C07K 16/30* (2013.01); *C07K 16/2866* (2013.01); *A61K 2039/505* (2013.01); *C07K 2316/96* (2013.01); *C07K 2317/24* (2013.01)
USPC .................. 424/130.1; 424/134.1; 424/141.1; 424/143.1; 530/387.1; 530/387.3; 530/388.22

(58) Field of Classification Search
None
See application file for complete search history.

(56) References Cited

U.S. PATENT DOCUMENTS

2004/0028685 A1* 2/2004 Kinch et al. ............... 424/155.1
2009/0304721 A1* 12/2009 Kinch et al. ............... 424/183.1

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Pasquale. 'Eph receptors and ephrins in cancer: bidirectional signalling and beyond'. Nature Reviews Cancer. 2010, vol. 10, No. 3, pp. 165-180.
Kiewlich et al. 'Anti-EphA2 antibodies decrease EphA2 protein levels in murine CT26 colorectal and human MDA-231 breast tumors but do not inhibit tumor growth'. Neoplasia. 2006, vol. 8, No. 1, pp. 18-30.

* cited by examiner

*Primary Examiner* — Christine J Saoud
*Assistant Examiner* — Jon M Lockard
(74) *Attorney, Agent, or Firm* — Lathrop & Gage LLP; James H. Velema

(57) ABSTRACT

Antibodies, humanized antibodies, resurfaced antibodies, antibody fragments, derivatized antibodies, and conjugates of same with cytotoxic agents, which specifically bind to, and inhibit A class of Eph receptors, antagonize the effects of growth factors on the growth and survival of tumor cells, and which have minimal agonistic activity or are preferentially devoid of agonist activity. Said antibodies and fragments thereof may be used in the treatment of tumors that express elevated levels of A class of Eph receptors, such as breast cancer, colon cancer, lung cancer, ovarian carcinoma, synovial sarcoma and pancreatic cancer, and said derivatized antibodies may be used in the diagnosis and imaging of tumors that express elevated levels of A class of Eph receptors. Also provided are cytotoxic conjugates comprising a cell binding agent and a cytotoxic agent, therapeutic compositions comprising the conjugate, methods for using the conjugates in the inhibition of cell growth and the treatment of disease, and a kit comprising the cytotoxic conjugate are disclosed are all embodiments of the invention. In particular, the cell binding agent is a monoclonal antibody, and epitope-binding fragments thereof, that recognizes and binds the A class of Eph receptors.

29 Claims, 23 Drawing Sheets

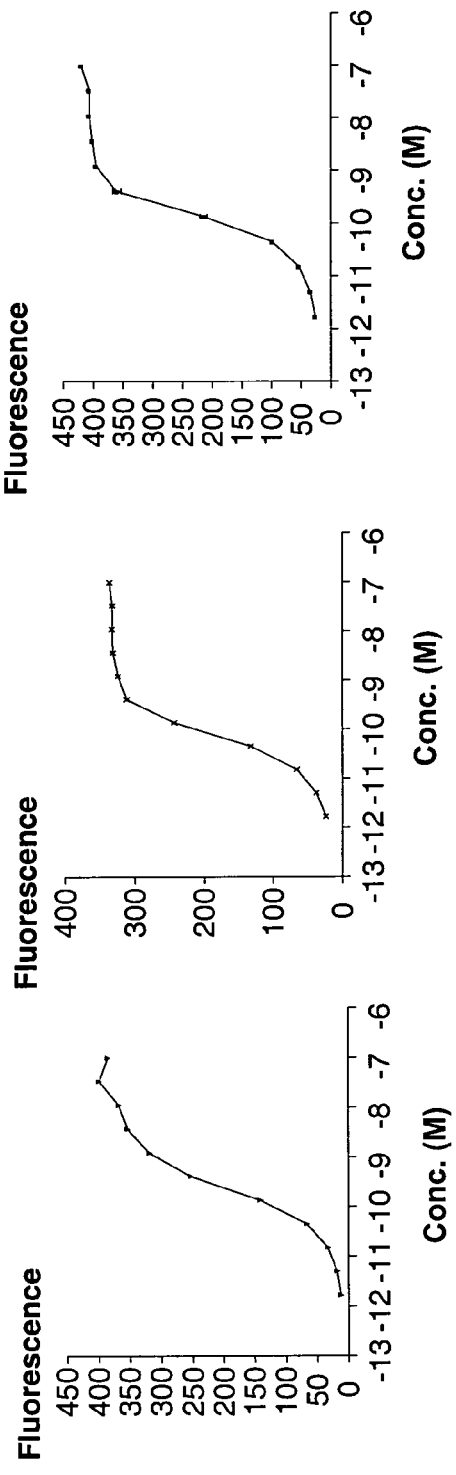

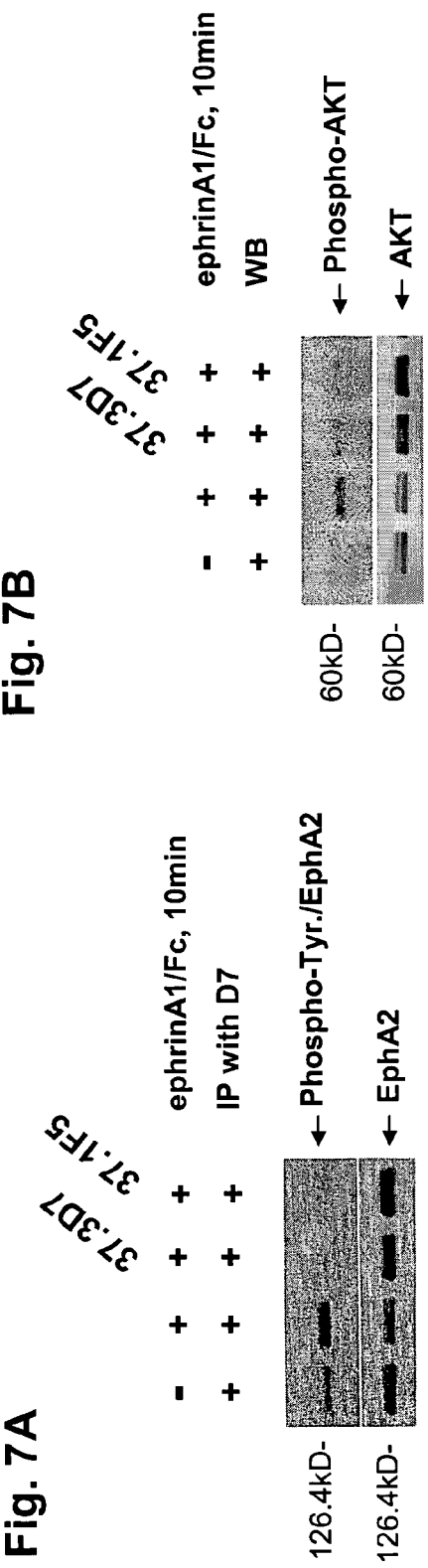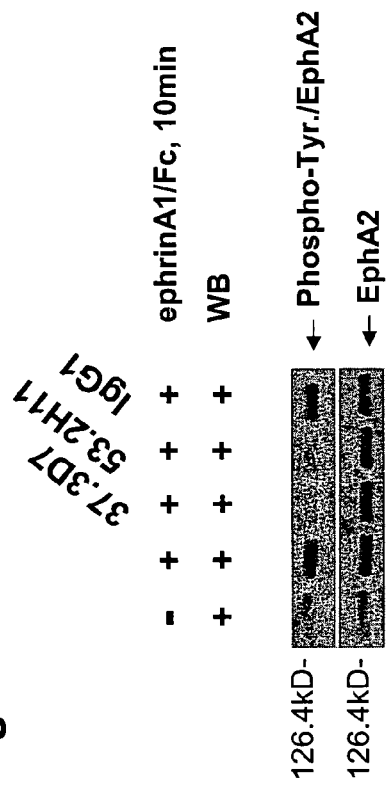
Fig. 7A
Fig. 7B
Fig. 7C

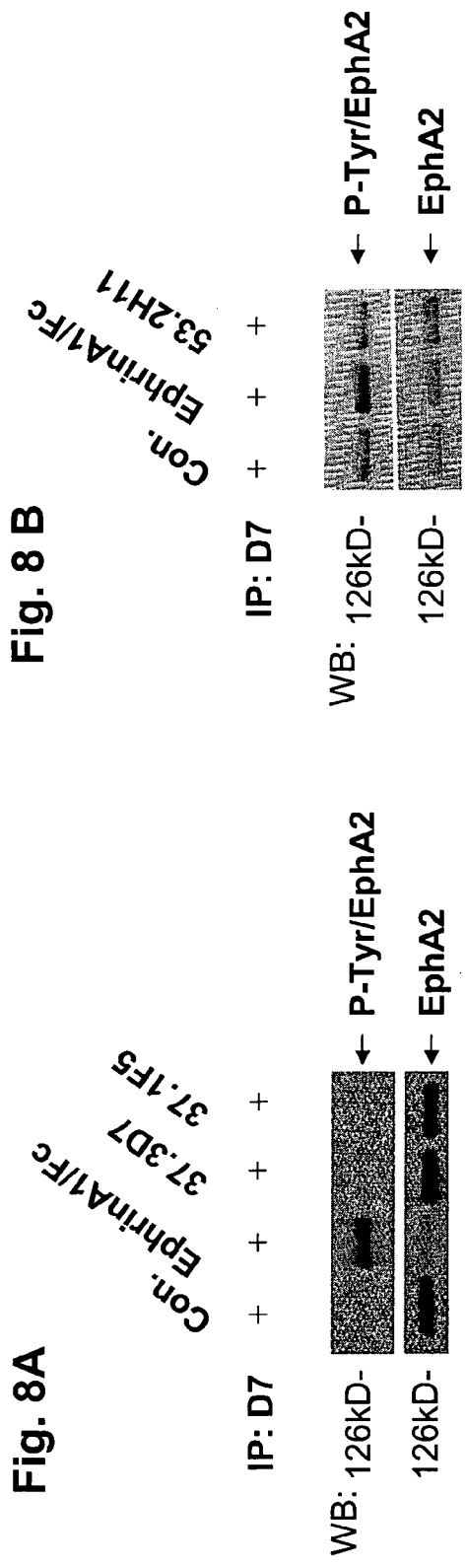

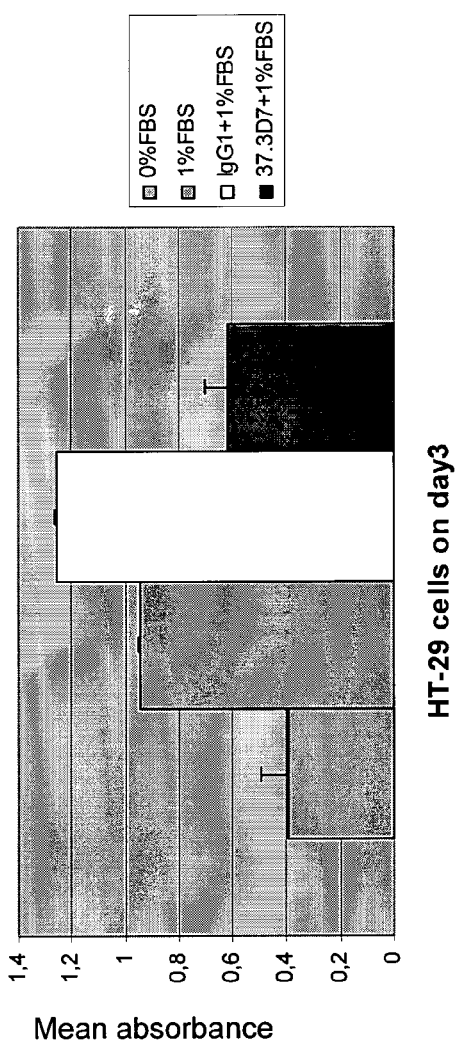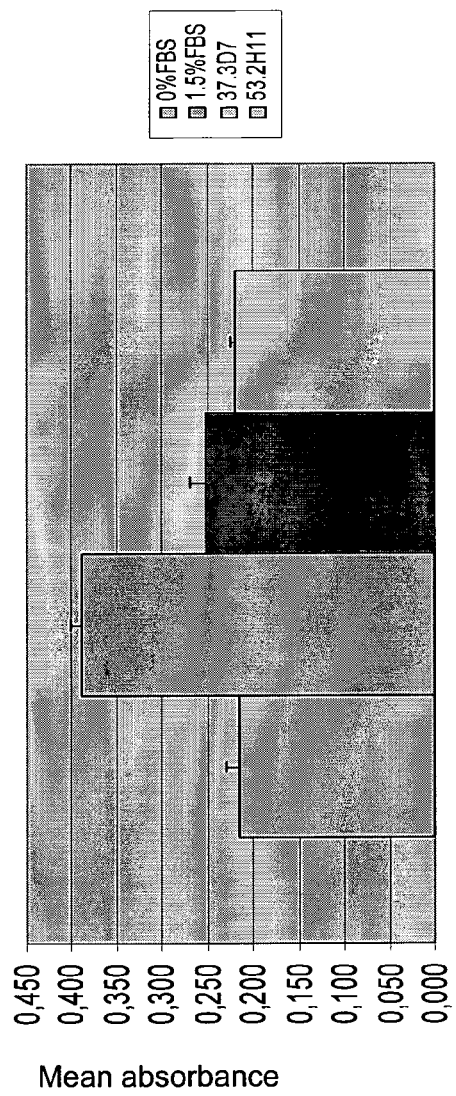
Fig. 9A
Fig. 9B

SEQUENCE LISTING

```
<160> NUMBER OF SEQ ID NOS: 80

<210> SEQ ID NO 1
<211> LENGTH: 5
<212> TYPE: PRT
<213> ORGANISM: Mus sp.

<400> SEQUENCE: 1

Ser Tyr Trp Met His
1               5

<210> SEQ ID NO 2
<211> LENGTH: 17
<212> TYPE: PRT
<213> ORGANISM: Mus sp.

<400> SEQUENCE: 2

Asn Ile Tyr Pro Gly Thr Gly Asn Thr Asn Tyr Asp Glu Lys Phe Met
1               5                   10                  15

Asn

<210> SEQ ID NO 3
<211> LENGTH: 12
<212> TYPE: PRT
<213> ORGANISM: Mus sp.

<400> SEQUENCE: 3

Trp Gly Leu Val Arg Tyr Phe Phe Ala Met Asp Tyr
1               5                   10

<210> SEQ ID NO 4
<211> LENGTH: 12
<212> TYPE: PRT
<213> ORGANISM: Mus sp.

<400> SEQUENCE: 4

Thr Val Ser Ser Ser Val Asn Ser Ser Tyr Leu His
1               5                   10

<210> SEQ ID NO 5
<211> LENGTH: 7
<212> TYPE: PRT
<213> ORGANISM: Mus sp.

<400> SEQUENCE: 5

Ser Thr Ser Asn Leu Pro Ser
1               5
```

```
<210> SEQ ID NO 6
<211> LENGTH: 10
<212> TYPE: PRT
<213> ORGANISM: Mus sp.

<400> SEQUENCE: 6

His Gln Tyr His Arg Ser Pro Gln Phe Thr
1               5                   10

<210> SEQ ID NO 7
<211> LENGTH: 5
<212> TYPE: PRT
<213> ORGANISM: Mus sp.

<400> SEQUENCE: 7

Gly Tyr Thr Met Asn
1               5

<210> SEQ ID NO 8
<211> LENGTH: 17
<212> TYPE: PRT
<213> ORGANISM: Mus sp.

<400> SEQUENCE: 8

Leu Ile Asn Pro His Asn Gly Gly Ser Ser Tyr Asn Leu Lys Phe Lys
1               5                   10                  15

Gly

<210> SEQ ID NO 9
<211> LENGTH: 9
<212> TYPE: PRT
<213> ORGANISM: Mus sp.

<400> SEQUENCE: 9

Trp Gly Asp Tyr Gly Ser Phe Ala Tyr
1               5

<210> SEQ ID NO 10
<211> LENGTH: 15
<212> TYPE: PRT
<213> ORGANISM: Mus sp.

<400> SEQUENCE: 10

Arg Ala Ser Glu Ser Val Asp Thr Phe Gly Tyr Ser Phe Ile Tyr
1               5                   10                  15

<210> SEQ ID NO 11
<211> LENGTH: 7
<212> TYPE: PRT
<213> ORGANISM: Mus sp.

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Mus sp.

<400> SEQUENCE: 12

Gln Gln Ser Asn Glu Asp Pro Pro Thr
1               5
```

<210> SEQ ID NO 13
<211> LENGTH: 5
<212> TYPE: PRT
<213> ORGANISM: Mus sp.

<400> SEQUENCE: 13

Ala Tyr Tyr Met His
1               5

<210> SEQ ID NO 14
<211> LENGTH: 17
<212> TYPE: PRT
<213> ORGANISM: Mus sp.

<400> SEQUENCE: 14

Leu Val Asn Pro Tyr Asn Gly Phe Ser Ser Tyr Asn Gln Asn Phe Glu
1               5                   10                  15

Asp

<210> SEQ ID NO 15
<211> LENGTH: 10
<212> TYPE: PRT
<213> ORGANISM: Mus sp.

<400> SEQUENCE: 15

Glu Phe Tyr Gly Tyr Arg Tyr Phe Asp Val
1               5                   10

<210> SEQ ID NO 16
<211> LENGTH: 16
<212> TYPE: PRT
<213> ORGANISM: Mus sp.

<400> SEQUENCE: 16

Lys Ser Ser Gln Ser Leu Ile His Ser Asp Gly Lys Thr Tyr Leu Asn
1               5                   10                  15

<210> SEQ ID NO 17
<211> LENGTH: 7
<212> TYPE: PRT
<213> ORGANISM: Mus sp.

<400> SEQUENCE: 17

Leu Val Ser Arg Leu Asp Ser
1               5

<210> SEQ ID NO 18
<211> LENGTH: 9
<212> TYPE: PRT
<213> ORGANISM: Mus sp.

<400> SEQUENCE: 18

Trp Gln Gly Ser His Phe Pro Arg Thr
1               5

<210> SEQ ID NO 19
<211> LENGTH: 363
<212> TYPE: DNA
<213> ORGANISM: Mus sp.
<220> FEATURE:
<221> NAME/KEY: CDS
<222> LOCATION: (1)..(363)

<400> SEQUENCE: 19

```
cag gtc caa ctg caa caa cct ggg tct gaa ctg gtg agg cct gga gct     48
Gln Val Gln Leu Gln Gln Pro Gly Ser Glu Leu Val Arg Pro Gly Ala
1               5                   10                  15 tca gtg cag ctg tcc tgt aag gct tct ggc tac tca ttc acc agc tac     96
Ser Val Gln Leu Ser Cys Lys Ala Ser Gly Tyr Ser Phe Thr Ser Tyr
            20                  25                  30 tgg atg cac tgg gtg aga cag agg cct gga caa ggc ctt caa tgg att    144
Trp Met His Trp Val Arg Gln Arg Pro Gly Gln Gly Leu Gln Trp Ile
        35                  40                  45 gga aat att tat cct ggt act ggt aat act aat tac gat gag aaa ttc    192
Gly Asn Ile Tyr Pro Gly Thr Gly Asn Thr Asn Tyr Asp Glu Lys Phe
    50                  55                  60 atg aac aag gcc aca ctg act gta gac aca tat tcc agc aca acc tac    240
Met Asn Lys Ala Thr Leu Thr Val Asp Thr Tyr Ser Ser Thr Thr Tyr
65                  70                  75                  80 atg cag ctc agc agc ctg aca tct gag gac tct gcg gtc tat tac tgt    288
Met Gln Leu Ser Ser Leu Thr Ser Glu Asp Ser Ala Val Tyr Tyr Cys
                85                  90                  95 gca aga tgg ggg tta gta cgg tat ttc ttt gca atg gac tac tgg ggt    336
Ala Arg Trp Gly Leu Val Arg Tyr Phe Phe Ala Met Asp Tyr Trp Gly
            100                 105                 110 caa gga acc tca gtc acc gtc tcc tca                                363
Gln Gly Thr Ser Val Thr Val Ser Ser
        115                 120

<210> SEQ ID NO 20
<211> LENGTH: 121
<212> TYPE: PRT
<213> ORGANISM: Mus sp.

<400> SEQUENCE: 20

Gln Val Gln Leu Gln Gln Pro Gly Ser Glu Leu Val Arg Pro Gly Ala
1               5                   10                  15

Ser Val Gln Leu Ser Cys Lys Ala Ser Gly Tyr Ser Phe Thr Ser Tyr
            20                  25                  30

Trp Met His Trp Val Arg Gln Arg Pro Gly Gln Gly Leu Gln Trp Ile
        35                  40                  45

Gly Asn Ile Tyr Pro Gly Thr Gly Asn Thr Asn Tyr Asp Glu Lys Phe
    50                  55                  60

Met Asn Lys Ala Thr Leu Thr Val Asp Thr Tyr Ser Ser Thr Thr Tyr
65                  70                  75                  80

Met Gln Leu Ser Ser Leu Thr Ser Glu Asp Ser Ala Val Tyr Tyr Cys
                85                  90                  95

Ala Arg Trp Gly Leu Val Arg Tyr Phe Phe Ala Met Asp Tyr Trp Gly
            100                 105                 110

Gln Gly Thr Ser Val Thr Val Ser Ser
        115                 120

<210> SEQ ID NO 21
<211> LENGTH: 354
<212> TYPE: DNA
<213> ORGANISM: Mus sp.
<220> FEATURE:
<221> NAME/KEY: CDS
<222> LOCATION: (1)..(354)

<400> SEQUENCE: 21 gag gtc cag ctg caa cag tct gga cct gag ctg gtg aag cct gga gct     48
Glu Val Gln Leu Gln Gln Ser Gly Pro Glu Leu Val Lys Pro Gly Ala
1               5                   10                  15
```

```
tca atg aag att tcc tgc agg gct tct ggt tac tca ttc act ggc tac      96
Ser Met Lys Ile Ser Cys Arg Ala Ser Gly Tyr Ser Phe Thr Gly Tyr
         20                  25                  30 acc atg aac tgg gtg agg cag agc cat gga aag aac ctt gag tgg att     144
Thr Met Asn Trp Val Arg Gln Ser His Gly Lys Asn Leu Glu Trp Ile
     35                  40                  45 gga ctt att aat cct cac aat ggt ggt tct agc tac aac ctg aag ttc     192
Gly Leu Ile Asn Pro His Asn Gly Gly Ser Ser Tyr Asn Leu Lys Phe
 50                  55                  60 aag ggc aag gcc aca tta act gta gac aag tca tcc agc aca gcc tac     240
Lys Gly Lys Ala Thr Leu Thr Val Asp Lys Ser Ser Ser Thr Ala Tyr
65                  70                  75                  80 atg gag ctc ctc agt ctg aca tct gaa gac tct gca gtc tat tac tgt     288
Met Glu Leu Leu Ser Leu Thr Ser Glu Asp Ser Ala Val Tyr Tyr Cys
                 85                  90                  95 gta aga tgg ggt gac tac ggc tct ttt gct tac tgg ggc caa ggg act     336
Val Arg Trp Gly Asp Tyr Gly Ser Phe Ala Tyr Trp Gly Gln Gly Thr
            100                 105                 110 ctg gtc act gtc tct gca                                             354
Leu Val Thr Val Ser Ala
        115

<210> SEQ ID NO 22
<211> LENGTH: 118
<212> TYPE: PRT
<213> ORGANISM: Mus sp.

<400> SEQUENCE: 22

Glu Val Gln Leu Gln Gln Ser Gly Pro Glu Leu Val Lys Pro Gly Ala
1               5                   10                  15

Ser Met Lys Ile Ser Cys Arg Ala Ser Gly Tyr Ser Phe Thr Gly Tyr
            20                  25                  30

Thr Met Asn Trp Val Arg Gln Ser His Gly Lys Asn Leu Glu Trp Ile
        35                  40                  45

Gly Leu Ile Asn Pro His Asn Gly Gly Ser Ser Tyr Asn Leu Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Val Arg Trp Gly Asp Tyr Gly Ser Phe Ala Tyr Trp Gly Gln Gly Thr
            100                 105                 110

Leu Val Thr Val Ser Ala
        115

<210> SEQ ID NO 23
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 23 gag gtc cag ctg caa cag tct gga cct gag ctg gtg aag cct ggg gct      48
Glu Val Gln Leu Gln Gln Ser Gly Pro Glu Leu Val Lys Pro Gly Ala
1               5                   10                  15 tca gtg aag att tcc tgc aag gct tct ggt tac tca ttc act gcc tac      96
Ser Val Lys Ile Ser Cys Lys Ala Ser Gly Tyr Ser Phe Thr Ala Tyr
            20                  25                  30
```

| | | | | | | | | | | | | | | | | |
|---|---|---|---|---|---|---|---|---|---|---|---|---|---|---|---|---|
| tac | atg | cac | tgg | gtg | aag | caa | agt | cat | gta | aag | agt | ctt | gag | tgg | att | 144 |
| Tyr | Met | His | Trp | Val | Lys | Gln | Ser | His | Val | Lys | Ser | Leu | Glu | Trp | Ile | |
| | | | 35 | | | | | 40 | | | | | 45 | | | |
| gga | ctt | gtt | aat | cct | tac | aat | ggt | ttt | agt | agc | tac | aac | cag | aat | ttc | 192 |
| Gly | Leu | Val | Asn | Pro | Tyr | Asn | Gly | Phe | Ser | Ser | Tyr | Asn | Gln | Asn | Phe | |
| | 50 | | | | | 55 | | | | | 60 | | | | | |
| gag | gac | aag | gcc | agc | ttg | act | gta | gat | aag | ttc | tcc | agc | acc | gcc | tac | 240 |
| Glu | Asp | Lys | Ala | Ser | Leu | Thr | Val | Asp | Lys | Phe | Ser | Ser | Thr | Ala | Tyr | |
| 65 | | | | | 70 | | | | | 75 | | | | | 80 | |
| atg | gaa | ctc | cac | agc | ctg | aca | tct | gag | gac | tct | gca | gtc | tat | tac | tgt | 288 |
| Met | Glu | Leu | His | Ser | Leu | Thr | Ser | Glu | Asp | Ser | Ala | Val | Tyr | Tyr | Cys | |
| | | | | 85 | | | | | 90 | | | | | 95 | | |
| gca | aga | gaa | ttc | tac | ggc | tac | cgg | tac | ttc | gat | gtc | tgg | ggc | gca | ggg | 336 |
| Ala | Arg | Glu | Phe | Tyr | Gly | Tyr | Arg | Tyr | Phe | Asp | Val | Trp | Gly | Ala | Gly | |
| | | | 100 | | | | | 105 | | | | | 110 | | | |
| acc | gcg | gtc | acc | gtc | tcc | tca | | | | | | | | | | 357 |
| Thr | Ala | Val | Thr | Val | Ser | Ser | | | | | | | | | | |
| | | | 115 | | | | | | | | | | | | | |

<210> SEQ ID NO 24
<211> LENGTH: 119
<212> TYPE: PRT
<213> ORGANISM: Mus sp.

<400> SEQUENCE: 24

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Tyr Met His Trp Val Lys Gln Ser His Val Lys Ser Leu Glu Trp Ile
        35                  40                  45

Gly Leu Val Asn Pro Tyr Asn Gly Phe Ser Ser Tyr Asn Gln Asn Phe
    50                  55                  60

Glu Asp Lys Ala Ser Leu Thr Val Asp Lys Phe Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Ala Gly
            100                 105                 110

Thr Ala Val Thr Val Ser Ser
        115

<210> SEQ ID NO 25
<211> LENGTH: 333
<212> TYPE: DNA
<213> ORGANISM: Mus sp.
<220> FEATURE:
<221> NAME/KEY: CDS
<222> LOCATION: (1)..(333)

<400> SEQUENCE: 25

| | | | | | | | | | | | | | | | | |
|---|---|---|---|---|---|---|---|---|---|---|---|---|---|---|---|---|
| caa | att | gtt | ctc | acc | cag | tct | cca | gca | atc | atg | tct | gca | tct | cta | ggg | 48 |
| Gln | Ile | Val | Leu | Thr | Gln | Ser | Pro | Ala | Ile | Met | Ser | Ala | Ser | Leu | Gly | |
| 1 | | | | 5 | | | | | 10 | | | | | 15 | | |
| gaa | cgg | gtc | acc | atg | acc | tgc | act | gtc | agc | tca | agt | gtg | aat | tcc | agt | 96 |
| Glu | Arg | Val | Thr | Met | Thr | Cys | Thr | Val | Ser | Ser | Ser | Val | Asn | Ser | Ser | |
| | | | 20 | | | | | 25 | | | | | 30 | | | |
| tac | ttg | cac | tgg | tac | cag | cag | aag | cca | gga | tcc | tcc | ccc | aaa | ctc | tgg | 144 |
| Tyr | Leu | His | Trp | Tyr | Gln | Gln | Lys | Pro | Gly | Ser | Ser | Pro | Lys | Leu | Trp | |
| | 35 | | | | | 40 | | | | | 45 | | | | | |

```
att tat agc aca tcc aac ctg cct tct gga gtc cca gct cgc ttc agt      192
Ile Tyr Ser Thr Ser Asn Leu Pro Ser Gly Val Pro Ala Arg Phe Ser
    50                  55                  60 ggc agt gga tct ggg acc tct tac tct ctc aca atc agc acc ata gag      240
Gly Ser Gly Ser Gly Thr Ser Tyr Ser Leu Thr Ile Ser Thr Ile Glu
 65                  70                  75                  80 tct gaa gat gct gcc act tat tac tgt cac cag tat cat cgt tcc cca      288
Ser Glu Asp Ala Ala Thr Tyr Tyr Cys His Gln Tyr His Arg Ser Pro
                 85                  90                  95 caa ttc acg ttc ggc tcg ggg aca aag ttg gag ata aaa cgg gct          333
Gln Phe Thr Phe Gly Ser Gly Thr Lys Leu Glu Ile Lys Arg Ala
            100                 105                 110
```

<210> SEQ ID NO 26
<211> LENGTH: 111
<212> TYPE: PRT
<213> ORGANISM: Mus sp.

<400> SEQUENCE: 26

```
Gln Ile Val Leu Thr Gln Ser Pro Ala Ile Met Ser Ala Ser Leu Gly
 1               5                  10                  15

Glu Arg Val Thr Met Thr Cys Thr Val Ser Ser Ser Val Asn Ser Ser
                20                  25                  30

Tyr Leu His Trp Tyr Gln Gln Lys Pro Gly Ser Ser Pro Lys Leu Trp
             35                  40                  45

Ile Tyr Ser Thr Ser Asn Leu Pro Ser Gly Val Pro Ala Arg Phe Ser
    50                  55                  60

Gly Ser Gly Ser Gly Thr Ser Tyr Ser Leu Thr Ile Ser Thr Ile Glu
 65                  70                  75                  80

Ser Glu Asp Ala Ala Thr Tyr Tyr Cys His Gln Tyr His Arg Ser Pro
                 85                  90                  95

Gln Phe Thr Phe Gly Ser Gly Thr Lys Leu Glu Ile Lys Arg Ala
            100                 105                 110
```

<210> SEQ ID NO 27
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 27

```
gac att gtg ctg acc caa tct cca gct tct ttg gct gtg tct cta ggg      48
Asp Ile Val Leu Thr Gln Ser Pro Ala Ser Leu Ala Val Ser Leu Gly
 1               5                  10                  15 cag agg gcc acc ata tcc tgc aga gcc agt gaa agt gtt gat act ttt      96
Gln Arg Ala Thr Ile Ser Cys Arg Ala Ser Glu Ser Val Asp Thr Phe
                20                  25                  30 ggc tat agt ttt ata tac tgg tac cag cag aag cca gga cag cca ccc     144
Gly Tyr Ser Phe Ile Tyr Trp Tyr Gln Gln Lys Pro Gly Gln Pro Pro
             35                  40                  45 aga ctc ctc atc tat cgt gca tcc aac cta gaa tct ggg atc cct gcc     192
Arg Leu Leu Ile Tyr Arg Ala Ser Asn Leu Glu Ser Gly Ile Pro Ala
    50                  55                  60 agg ttc agt ggc agt ggg tct agg aca gac ttc acc ctc acc att aat     240
Arg Phe Ser Gly Ser Gly Ser Arg Thr Asp Phe Thr Leu Thr Ile Asn
 65                  70                  75                  80 cct gtg gag gct gat gat gtt gca acc tat tac tgt cag caa agt aat     288
Pro Val Glu Ala Asp Asp Val Ala Thr Tyr Tyr Cys Gln Gln Ser Asn
```

```
                      85                  90                  95
gag gat cct ccg acg ttc ggt gga ggc acc aag ctg gaa atc aaa cgg        336
Glu Asp Pro Pro Thr Phe Gly Gly Gly Thr Lys Leu Glu Ile Lys Arg
            100                 105                 110

<210> SEQ ID NO 28
<211> LENGTH: 112
<212> TYPE: PRT
<213> ORGANISM: Mus sp.

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Phe
            20                  25                  30

Gly Tyr Ser Phe Ile Tyr Trp Tyr Gln Gln Lys Pro Gly Gln Pro Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Gly Gly Thr Lys Leu Glu Ile Lys Arg
            100                 105                 110

<210> SEQ ID NO 29
<211> LENGTH: 339
<212> TYPE: DNA
<213> ORGANISM: Mus sp.
<220> FEATURE:
<221> NAME/KEY: CDS
<222> LOCATION: (1)..(339)

<400> SEQUENCE: 29 gat gtt gtg atg tcc cag att cca ctc act ttg tcg gtc acc att gga         48
Asp Val Val Met Ser Gln Ile Pro Leu Thr Leu Ser Val Thr Ile Gly
1               5                   10                  15 caa cca gcc tcc atc tct tgc aag tca agt cag agc ctc ata cat agt         96
Gln Pro Ala Ser Ile Ser Cys Lys Ser Ser Gln Ser Leu Ile His Ser
            20                  25                  30 gat gga aag aca tat ttg aat tgg ttg tta cag agg cca ggc cag tct        144
Asp Gly Lys Thr Tyr Leu Asn Trp Leu Leu Gln Arg Pro Gly Gln Ser
        35                  40                  45 cca aag cgc cta att tat ctg gtg tct aga ctg gac tct gga gtc cct        192
Pro Lys Arg Leu Ile Tyr Leu Val Ser Arg Leu Asp Ser Gly Val Pro
    50                  55                  60 gac agg ttc act ggc agt gga tca ggg aca gat ttc aca ctg aaa atc        240
Asp Arg Phe Thr Gly Ser Gly Ser Gly Thr Asp Phe Thr Leu Lys Ile
65                  70                  75                  80 agc aga gtg gag gct gag gat ttg gga gtt tat tat tgc tgg caa ggt        288
Ser Arg Val Glu Ala Glu Asp Leu Gly Val Tyr Tyr Cys Trp Gln Gly
                85                  90                  95 tca cat ttt cct cgg acg ttc ggt gga ggc acc aag ctg gaa atc aaa        336
Ser His Phe Pro Arg Thr Phe Gly Gly Gly Thr Lys Leu Glu Ile Lys
            100                 105                 110 cgg                                                                    339
Arg

<210> SEQ ID NO 30
```

-continued

<211> LENGTH: 113
<212> TYPE: PRT
<213> ORGANISM: Mus sp.

<400> SEQUENCE: 30

Asp Val Val Met Ser Gln Ile Pro Leu Thr Leu Ser Val Thr Ile Gly
1               5                   10                  15

Gln Pro Ala Ser Ile Ser Cys Lys Ser Ser Gln Ser Leu Ile His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Arg Thr Phe Gly Gly Gly Thr Lys Leu Glu Ile Lys
            100                 105                 110

Arg

<210> SEQ ID NO 31
<211> LENGTH: 363
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(363)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
<220> FEATURE:
<221> NAME/KEY: source
<222> LOCATION: (148)..(192)
<223> OTHER INFORMATION: Mus sp.
<220> FEATURE:
<221> NAME/KEY: source
<222> LOCATION: (193)..(294)
<223> OTHER INFORMATION: homo sapiens
<220> FEATURE:
<221> NAME/KEY: source
<222> LOCATION: (295)..(330)
<223> OTHER INFORMATION: Mus sp.
<220> FEATURE:
<221> NAME/KEY: source
<222> LOCATION: (331)..(363)
<223> OTHER INFORMATION: homo sapiens

<400> SEQUENCE: 31 cag gtt cag ctt gtc cag cct gga gct gaa gtg gta aag cca gga gcc      48
Gln Val Gln Leu Val Gln Pro Gly Ala Glu Val Val Lys Pro Gly Ala
1               5                   10                  15 tct gtg aag ctc tct tgt aaa gca agc ggc tac aac ttc acc agc tat      96
Ser Val Lys Leu Ser Cys Lys Ala Ser Gly Tyr Asn Phe Thr Ser Tyr
            20                  25                  30 tgg atg cac tgg gtg cgt cag cgt ccc ggc cag gga ctc cag tgg ata     144

```
                                                             -continued

Trp Met His Trp Val Arg Gln Arg Pro Gly Gln Gly Leu Gln Trp Ile
         35                  40                  45 ggc aac atc tac ccc ggc acc ggt aat aca aac tat gac cag aag ttc    192
Gly Asn Ile Tyr Pro Gly Thr Gly Asn Thr Asn Tyr Asp Gln Lys Phe
 50                  55                  60 caa ggc aag gct acc ctt aca gtt gac acc tct acc agc act act tat    240
Gln Gly Lys Ala Thr Leu Thr Val Asp Thr Ser Thr Ser Thr Thr Tyr
 65                  70                  75                  80 atg caa ttg tcc agc ctg act agc gag gat tcc gcc gtg tat tat tgt    288
Met Gln Leu Ser Ser Leu Thr Ser Glu Asp Ser Ala Val Tyr Tyr Cys
                 85                  90                  95 gcc agg tgg ggc ctt gtt agg tac ttc ttc gct atg gat tac tgg ggg    336
Ala Arg Trp Gly Leu Val Arg Tyr Phe Phe Ala Met Asp Tyr Trp Gly
            100                 105                 110 cag ggt act agc gtt aca gtt tcc agt                                363
Gln Gly Thr Ser Val Thr Val Ser Ser
        115                 120

<210> SEQ ID NO 32
<211> LENGTH: 121
<212> TYPE: PRT
<213> ORGANISM: Artificial
<220> FEATURE:
<223> OTHER INFORMATION: Synthetic Construct

<400> SEQUENCE: 32

Gln Val Gln Leu Val Gln Pro Gly Ala Glu Val Val Lys Pro Gly Ala
  1               5                  10                  15

Ser Val Lys Leu Ser Cys Lys Ala Ser Gly Tyr Asn Phe Thr Ser Tyr
             20                  25                  30

Trp Met His Trp Val Arg Gln Arg Pro Gly Gln Gly Leu Gln Trp Ile
         35                  40                  45

Gly Asn Ile Tyr Pro Gly Thr Gly Asn Thr Asn Tyr Asp Gln Lys Phe
 50                  55                  60

Gln Gly Lys Ala Thr Leu Thr Val Asp Thr Ser Thr Ser Thr Thr Tyr
 65                  70                  75                  80

Met Gln Leu Ser Ser Leu Thr Ser Glu Asp Ser Ala Val Tyr Tyr Cys
                 85                  90                  95

Ala Arg Trp Gly Leu Val Arg Tyr Phe Phe Ala Met Asp Tyr Trp Gly
            100                 105                 110

Gln Gly Thr Ser Val Thr Val Ser Ser
        115                 120

<210> SEQ ID NO 33
<211> LENGTH: 363
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(363)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
```

```
<220> FEATURE:
<221> NAME/KEY: source
<222> LOCATION: (148)..(192)
<223> OTHER INFORMATION: Mus sp.
<220> FEATURE:
<221> NAME/KEY: source
<222> LOCATION: (193)..(294)
<223> OTHER INFORMATION: homo sapiens
<220> FEATURE:
<221> NAME/KEY: source
<222> LOCATION: (295)..(330)
<223> OTHER INFORMATION: Mus sp.
<220> FEATURE:
<221> NAME/KEY: source
<222> LOCATION: (331)..(363)
<223> OTHER INFORMATION: homo sapiens

<400> SEQUENCE: 33 cag gtg cag ctc gtc cag ccc ggt gcc gaa gtg gtg aaa ccc ggt gct      48
Gln Val Gln Leu Val Gln Pro Gly Ala Glu Val Val Lys Pro Gly Ala
1               5                   10                  15 tct gtg aag ctg tca tgc aag gcc tca ggc tat agt ttc acc tca tat      96
Ser Val Lys Leu Ser Cys Lys Ala Ser Gly Tyr Ser Phe Thr Ser Tyr
            20                  25                  30 tgg atg cat tgg gtc cgc cag agg cca ggc cag ggc ctc caa tgg atc     144
Trp Met His Trp Val Arg Gln Arg Pro Gly Gln Gly Leu Gln Trp Ile
        35                  40                  45 gga aac atc tac cct ggc aca gga aat acc aat tat gac cag aaa ttc     192
Gly Asn Ile Tyr Pro Gly Thr Gly Asn Thr Asn Tyr Asp Gln Lys Phe
    50                  55                  60 caa ggt aag gcc act ctg acc gtg gac act agc aca tca acc aca tac     240
Gln Gly Lys Ala Thr Leu Thr Val Asp Thr Ser Thr Ser Thr Thr Tyr
65                  70                  75                  80 atg cag ctg tct tct ctc act tca gaa gac agt gct gtc tac tac tgc     288
Met Gln Leu Ser Ser Leu Thr Ser Glu Asp Ser Ala Val Tyr Tyr Cys
                85                  90                  95 gca cga tgg ggc ctc gtt cgt tat ttc ttc gca atg gat tat tgg ggt     336
Ala Arg Trp Gly Leu Val Arg Tyr Phe Phe Ala Met Asp Tyr Trp Gly
            100                 105                 110 caa ggc aca tca gtt acc gtg tcc tct                                 363
Gln Gly Thr Ser Val Thr Val Ser Ser
        115                 120

<210> SEQ ID NO 34
<211> LENGTH: 121
<212> TYPE: PRT
<213> ORGANISM: Artificial
<220> FEATURE:
<223> OTHER INFORMATION: Synthetic Construct

<400> SEQUENCE: 34

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Arg Gln Arg Pro Gly Gln Gly Leu Gln Trp Ile
        35                  40                  45

Gly Asn Ile Tyr Pro Gly Thr Gly Asn Thr Asn Tyr Asp Gln Lys Phe
    50                  55                  60

Gln Gly Lys Ala Thr Leu Thr Val Asp Thr Ser Thr Ser Thr Thr Tyr
65                  70                  75                  80

Met Gln Leu Ser Ser Leu Thr Ser Glu Asp Ser Ala Val Tyr Tyr Cys
                85                  90                  95
```

```
Ala Arg Trp Gly Leu Val Arg Tyr Phe Phe Ala Met Asp Tyr Trp Gly
            100                 105                 110

Gln Gly Thr Ser Val Thr Val Ser Ser
        115                 120

<210> SEQ ID NO 35
<211> LENGTH: 363
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(363)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
<220> FEATURE:
<221> NAME/KEY: source
<222> LOCATION: (148)..(192)
<223> OTHER INFORMATION: Mus sp.
<220> FEATURE:
<221> NAME/KEY: source
<222> LOCATION: (193)..(294)
<223> OTHER INFORMATION: homo sapiens
<220> FEATURE:
<221> NAME/KEY: source
<222> LOCATION: (295)..(330)
<223> OTHER INFORMATION: Mus sp.
<220> FEATURE:
<221> NAME/KEY: source
<222> LOCATION: (331)..(363)
<223> OTHER INFORMATION: homo sapiens

<400> SEQUENCE: 35 cag gtg cag ctg gtg cag ccc ggg gct gag gtg gta aag cca gga gcc      48
Gln Val Gln Leu Val Gln Pro Gly Ala Glu Val Val Lys Pro Gly Ala
1               5                   10                  15 agt gtg aag ttg tcc tgc aag gcc tcc ggg tac aat ttc acc tct tac      96
Ser Val Lys Leu Ser Cys Lys Ala Ser Gly Tyr Asn Phe Thr Ser Tyr
            20                  25                  30 tgg atg cat tgg gtg cgt cag cgg cct ggg caa gga ctt caa tgg atc     144
Trp Met His Trp Val Arg Gln Arg Pro Gly Gln Gly Leu Gln Trp Ile
        35                  40                  45 ggg aat att tac ccc ggt acc ggc aat aca aat tat gat cag aag ttc     192
Gly Asn Ile Tyr Pro Gly Thr Gly Asn Thr Asn Tyr Asp Gln Lys Phe
    50                  55                  60 cag ggc aag gct aca ttg acc gtg gat acc tac act tct act act tac     240
Gln Gly Lys Ala Thr Leu Thr Val Asp Thr Tyr Thr Ser Thr Thr Tyr
65                  70                  75                  80 atg caa ctg agc tca ctg acc tcc gag gac tca gcc gtg tac tat tgc     288
Met Gln Leu Ser Ser Leu Thr Ser Glu Asp Ser Ala Val Tyr Tyr Cys
                85                  90                  95 gca cgc tgg gga ctc gtc agg tat ttc ttt gcc atg gat tac tgg gga     336
Ala Arg Trp Gly Leu Val Arg Tyr Phe Phe Ala Met Asp Tyr Trp Gly
            100                 105                 110 cag ggg acc tct gtc acc gtg agc agt                                 363
Gln Gly Thr Ser Val Thr Val Ser Ser
        115                 120
```

```
<210> SEQ ID NO 36
<211> LENGTH: 121
<212> TYPE: PRT
<213> ORGANISM: Artificial
<220> FEATURE:
<223> OTHER INFORMATION: Synthetic Construct

<400> SEQUENCE: 36

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Asn Phe Thr Ser Tyr
            20                  25                  30

Trp Met His Trp Val Arg Gln Arg Pro Gly Gln Gly Leu Gln Trp Ile
        35                  40                  45

Gly Asn Ile Tyr Pro Gly Thr Gly Asn Thr Asn Tyr Asp Gln Lys Phe
    50                  55                  60

Gln Gly Lys Ala Thr Leu Thr Val Asp Thr Tyr Thr Ser Thr Thr Tyr
65                  70                  75                  80

Met Gln Leu Ser Ser Leu Thr Ser Glu Asp Ser Ala Val Tyr Tyr Cys
                85                  90                  95

Ala Arg Trp Gly Leu Val Arg Tyr Phe Phe Ala Met Asp Tyr Trp Gly
            100                 105                 110

Gln Gly Thr Ser Val Thr Val Ser Ser
        115                 120

<210> SEQ ID NO 37
<211> LENGTH: 118
<212> TYPE: PRT
<213> ORGANISM: Artificial
<220> FEATURE:
<223> OTHER INFORMATION: Humanized antibody

<400> SEQUENCE: 37

Glu Val Gln Leu Leu Gln Ser Gly Gly Glu Leu Val Gln Pro Gly Ala
1               5                   10                  15

Ser Met Arg Ile Ser Cys Ala Ala Ser Gly Tyr Thr Phe Thr Gly Tyr
            20                  25                  30

Thr Met Asn Trp Val Arg Gln Ser Pro Gly Lys Asn Leu Glu Trp Ile
        35                  40                  45

Gly Leu Ile Asn Pro His Asn Gly Gly Ser Ser Tyr Asn Asp Ser Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ala Glu Asp Ser Ala Val Tyr Tyr Cys
                85                  90                  95

Val Arg Trp Gly Asp Tyr Gly Ser Phe Ala Tyr Trp Gly Gln Gly Thr
            100                 105                 110

Leu Val Thr Val Ser Ser
        115

<210> SEQ ID NO 38
<211> LENGTH: 118
<212> TYPE: PRT
<213> ORGANISM: Artificial
<220> FEATURE:
<223> OTHER INFORMATION: Humanized antibody

<400> SEQUENCE: 38

Glu Val Gln Leu Leu Gln Ser Gly Gly Glu Leu Val Gln Pro Gly Ala
```

```
1               5                   10                  15
Ser Met Arg Ile Ser Cys Ala Ala Ser Gly Tyr Ser Phe Thr Gly Tyr
                20                  25                  30

Thr Met Asn Trp Val Arg Gln Ser Pro Gly Lys Asn Leu Glu Trp Ile
            35                  40                  45

Gly Leu Ile Asn Pro His Asn Gly Gly Ser Ser Tyr Asn Asp Ser Phe
        50                  55                  60

Lys Gly Lys Ala Thr Leu Thr Val Asp Lys Ser Ser Thr Ala Tyr
65                  70                  75                  80

Met Glu Leu Leu Ser Leu Thr Ala Glu Asp Ser Ala Val Tyr Tyr Cys
                85                  90                  95

Val Arg Trp Gly Asp Tyr Gly Ser Phe Ala Tyr Trp Gly Gln Gly Thr
                100                 105                 110

Leu Val Thr Val Ser Ser
        115
```

<210> SEQ ID NO 39
<211> LENGTH: 357
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(357)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
<220> FEATURE:
<221> NAME/KEY: source
<222> LOCATION: (148)..(195)
<223> OTHER INFORMATION: Mus sp.
<220> FEATURE:
<221> NAME/KEY: source
<222> LOCATION: (196)..(294)
<223> OTHER INFORMATION: homo sapiens
<220> FEATURE:
<221> NAME/KEY: source
<222> LOCATION: (295)..(324)
<223> OTHER INFORMATION: Mus sp.
<220> FEATURE:
<221> NAME/KEY: source
<222> LOCATION: (325)..(357)
<223> OTHER INFORMATION: homo sapiens

<400> SEQUENCE: 39

```
cag gtg caa ctg gtg caa tcc ggt gcc gag gtc gtc aaa ccc gga gca    48
Gln Val Gln Leu Val Gln Ser Gly Ala Glu Val Val Lys Pro Gly Ala
1               5                   10                  15 tct gtg aag ata tcc tgt aag gcc tcc ggc tac act ttt aca gcc tac    96
Ser Val Lys Ile Ser Cys Lys Ala Ser Gly Tyr Thr Phe Thr Ala Tyr
                20                  25                  30 tat atg cat tgg gtt aaa cag agt ccc gtg cag tcc ctg gaa tgg atc   144
Tyr Met His Trp Val Lys Gln Ser Pro Val Gln Ser Leu Glu Trp Ile
            35                  40                  45 ggc ttg gtg aac cct tat aac gga ttc tca agt tac aat caa aag ttt   192
Gly Leu Val Asn Pro Tyr Asn Gly Phe Ser Ser Tyr Asn Gln Lys Phe
        50                  55                  60
```

```
cag ggc aag gct tcc ctg act gta gac aag agc agt tcc aca gcc tac     240
Gln Gly Lys Ala Ser Leu Thr Val Asp Lys Ser Ser Ser Thr Ala Tyr
65                  70                  75                  80 atg gag ctc cat tca ctg aca tca gaa gac agc gcc gta tac tat tgc     288
Met Glu Leu His Ser Leu Thr Ser Glu Asp Ser Ala Val Tyr Tyr Cys
                85                  90                  95 gca cgt gag ttc tac ggc tat aga tac ttt gac gtc tgg ggc caa ggc     336
Ala Arg Glu Phe Tyr Gly Tyr Arg Tyr Phe Asp Val Trp Gly Gln Gly
            100                 105                 110 aca gcc gtc aca gtg agc tct                                          357
Thr Ala Val Thr Val Ser Ser
        115
```

<210> SEQ ID NO 40
<211> LENGTH: 119
<212> TYPE: PRT
<213> ORGANISM: Artificial
<220> FEATURE:
<223> OTHER INFORMATION: Synthetic Construct

<400> SEQUENCE: 40

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Ala Tyr
            20                  25                  30

Tyr Met His Trp Val Lys Gln Ser Pro Val Gln Ser Leu Glu Trp Ile
        35                  40                  45

Gly Leu Val Asn Pro Tyr Asn Gly Phe Ser Ser Tyr Asn Gln Lys Phe
    50                  55                  60

Gln Gly Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Gln Gly
            100                 105                 110

Thr Ala Val Thr Val Ser Ser
        115
```

<210> SEQ ID NO 41
<211> LENGTH: 357
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(357)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
<220> FEATURE:
<221> NAME/KEY: source
<222> LOCATION: (148)..(195)
<223> OTHER INFORMATION: Mus sp.
<220> FEATURE:
<221> NAME/KEY: source

```
<222> LOCATION: (196)..(294)
<223> OTHER INFORMATION: homo sapiens
<220> FEATURE:
<221> NAME/KEY: source
<222> LOCATION: (295)..(324)
<223> OTHER INFORMATION: Mus sp.
<220> FEATURE:
<221> NAME/KEY: source
<222> LOCATION: (325)..(357)
<223> OTHER INFORMATION: homo sapiens

<400> SEQUENCE: 41 cag gtc cag ttg gtg cag tct gga gca gag gtt gtg aaa cca ggc gca        48
Gln Val Gln Leu Val Gln Ser Gly Ala Glu Val Val Lys Pro Gly Ala
1               5                   10                  15 agt gtc aaa atc agc tgt aag gct agc gga tac tcc ttt aca gca tat        96
Ser Val Lys Ile Ser Cys Lys Ala Ser Gly Tyr Ser Phe Thr Ala Tyr
            20                  25                  30 tat atg cac tgg gtg aag cag agc cct gtt cag agc ctg gaa tgg atc       144
Tyr Met His Trp Val Lys Gln Ser Pro Val Gln Ser Leu Glu Trp Ile
        35                  40                  45 ggt ctc gtc aac cct tat aat gga ttt tct tct tat aac caa aag ttc       192
Gly Leu Val Asn Pro Tyr Asn Gly Phe Ser Ser Tyr Asn Gln Lys Phe
    50                  55                  60 cag ggc aaa gcc agc ctg aca gtg gat aag agt agc agc act gcc tat       240
Gln Gly Lys Ala Ser Leu Thr Val Asp Lys Ser Ser Ser Thr Ala Tyr
65                  70                  75                  80 atg gaa ctg cat tct ctc acc tct gaa gat agt gca gtg tac tat tgt       288
Met Glu Leu His Ser Leu Thr Ser Glu Asp Ser Ala Val Tyr Tyr Cys
                85                  90                  95 gct cgc gag ttc tac ggt tat cga tat ttc gac gtg tgg ggc cag ggt       336
Ala Arg Glu Phe Tyr Gly Tyr Arg Tyr Phe Asp Val Trp Gly Gln Gly
            100                 105                 110 act gcc gtg aca gta agc agt                                           357
Thr Ala Val Thr Val Ser Ser
        115

<210> SEQ ID NO 42
<211> LENGTH: 119
<212> TYPE: PRT
<213> ORGANISM: Artificial
<220> FEATURE:
<223> OTHER INFORMATION: Synthetic Construct

<400> SEQUENCE: 42

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Ser Phe Thr Ala Tyr
            20                  25                  30

Tyr Met His Trp Val Lys Gln Ser Pro Val Gln Ser Leu Glu Trp Ile
        35                  40                  45

Gly Leu Val Asn Pro Tyr Asn Gly Phe Ser Ser Tyr Asn Gln Lys Phe
    50                  55                  60

Gln Gly Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Gln Gly
            100                 105                 110

Thr Ala Val Thr Val Ser Ser
        115
```

```
<210> SEQ ID NO 43
<211> LENGTH: 119
<212> TYPE: PRT
<213> ORGANISM: Artificial
<220> FEATURE:
<223> OTHER INFORMATION: Humanized antibody

<400> SEQUENCE: 43

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Ala Tyr
                20                  25                  30

Tyr Met His Trp Val Lys Gln Ser Pro Gly Gln Ser Leu Glu Trp Ile
            35                  40                  45

Gly Leu Val Asn Pro Tyr Asn Gly Phe Ser Ser Tyr Asn Gln Lys Phe
    50                  55                  60

Gln Gly Lys Ala Ser Leu Thr Val Asp Lys Ser Ser Ser Thr Ala Tyr
65                  70                  75                  80

Met Glu Leu His Ser Leu Thr Ser Glu Asp Ser Ala Val Tyr Tyr Cys
                85                  90                  95

Ala Arg Glu Phe Tyr Gly Tyr Arg Tyr Phe Asp Val Trp Gly Gln Gly
            100                 105                 110

Thr Ala Val Thr Val Ser Ser
        115

<210> SEQ ID NO 44
<211> LENGTH: 357
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(357)
<220> FEATURE:
<221> NAME/KEY: source
<222> LOCATION: (1)..(90)
<223> OTHER INFORMATION: homo sapiens
<220> FEATURE:
<221> NAME/KEY: source
<222> LOCATION: (91)..(105)
<223> OTHER INFORMATION: Mus sp.
<220> FEATURE:
<221> NAME/KEY: source
<222> LOCATION: (106)..(147)
<223> OTHER INFORMATION: homo sapiens
<220> FEATURE:
<221> NAME/KEY: source
<222> LOCATION: (148)..(195)
<223> OTHER INFORMATION: Mus sp.
<220> FEATURE:
<221> NAME/KEY: source
<222> LOCATION: (196)..(294)
<223> OTHER INFORMATION: homo sapiens
<220> FEATURE:
<221> NAME/KEY: source
<222> LOCATION: (295)..(324)
<223> OTHER INFORMATION: Mus sp.
<220> FEATURE:
<221> NAME/KEY: source
<222> LOCATION: (325)..(357)
<223> OTHER INFORMATION: homo sapiens

<400> SEQUENCE: 44 cag gtt caa ctg gtt cag agt ggg gca gaa gtc gta aag ccc gga gct    48
Gln Val Gln Leu Val Gln Ser Gly Ala Glu Val Val Lys Pro Gly Ala
1               5                   10                  15
```

```
tcc gtt aag att agc tgt aaa gcc tcc ggc tat agc ttt aca gct tac    96
Ser Val Lys Ile Ser Cys Lys Ala Ser Gly Tyr Ser Phe Thr Ala Tyr
         20                  25                  30 tat atg cac tgg gtc aag caa tct cct ggg cag agc ctg gag tgg atc   144
Tyr Met His Trp Val Lys Gln Ser Pro Gly Gln Ser Leu Glu Trp Ile
         35                  40                  45 ggc ctg gtc aat cca tac aat ggc ttc tct agt tac aac caa aaa ttt   192
Gly Leu Val Asn Pro Tyr Asn Gly Phe Ser Ser Tyr Asn Gln Lys Phe
 50                  55                  60 cag gga aaa gcc tcc ctt aca gta gac aag tca tct tcc act gcc tac   240
Gln Gly Lys Ala Ser Leu Thr Val Asp Lys Ser Ser Ser Thr Ala Tyr
 65                  70                  75                  80 atg gaa ctt cac tcc ctt aca agc gag gat agc gcc gtt tat tat tgt   288
Met Glu Leu His Ser Leu Thr Ser Glu Asp Ser Ala Val Tyr Tyr Cys
                 85                  90                  95 gcc aga gaa ttt tac gga tat cgg tat ttc gat gtc tgg ggg cag ggg   336
Ala Arg Glu Phe Tyr Gly Tyr Arg Tyr Phe Asp Val Trp Gly Gln Gly
                100                 105                 110 act gcc gtg acc gtc agt tct                                        357
Thr Ala Val Thr Val Ser Ser
        115
```

<210> SEQ ID NO 45
<211> LENGTH: 119
<212> TYPE: PRT
<213> ORGANISM: Artificial
<220> FEATURE:
<223> OTHER INFORMATION: Synthetic Construct

<400> SEQUENCE: 45

```
Gln Val Gln Leu Val Gln Ser Gly Ala Glu Val Val Lys Pro Gly Ala
 1               5                  10                  15

Ser Val Lys Ile Ser Cys Lys Ala Ser Gly Tyr Ser Phe Thr Ala Tyr
         20                  25                  30

Tyr Met His Trp Val Lys Gln Ser Pro Gly Gln Ser Leu Glu Trp Ile
         35                  40                  45

Gly Leu Val Asn Pro Tyr Asn Gly Phe Ser Ser Tyr Asn Gln Lys Phe
 50                  55                  60

Gln Gly Lys Ala Ser Leu Thr Val Asp Lys Ser Ser Ser Thr Ala Tyr
 65                  70                  75                  80

Met Glu Leu His Ser Leu Thr Ser Glu Asp Ser Ala Val Tyr Tyr Cys
                 85                  90                  95

Ala Arg Glu Phe Tyr Gly Tyr Arg Tyr Phe Asp Val Trp Gly Gln Gly
                100                 105                 110

Thr Ala Val Thr Val Ser Ser
        115
```

<210> SEQ ID NO 46
<211> LENGTH: 330
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(330)
<220> FEATURE:
<221> NAME/KEY: source
<222> LOCATION: (1)..(71)
<223> OTHER INFORMATION: homo sapiens
<220> FEATURE:
<221> NAME/KEY: source
<222> LOCATION: (72)..(105)

```
<223> OTHER INFORMATION: Mus sp.
<220> FEATURE:
<221> NAME/KEY: source
<222> LOCATION: (106)..(150)
<223> OTHER INFORMATION: homo sapiens
<220> FEATURE:
<221> NAME/KEY: source
<222> LOCATION: (151)..(171)
<223> OTHER INFORMATION: Mus sp.
<220> FEATURE:
<221> NAME/KEY: source
<222> LOCATION: (172)..(269)
<223> OTHER INFORMATION: homo sapiens
<220> FEATURE:
<221> NAME/KEY: source
<222> LOCATION: (270)..(299)
<223> OTHER INFORMATION: Mus sp.
<220> FEATURE:
<221> NAME/KEY: source
<222> LOCATION: (300)..(330)
<223> OTHER INFORMATION: homo sapiens

<400> SEQUENCE: 46 gag atc gtt ctc aca cag tca cca gcc acc atg agc gcc tct ccc ggg     48
Glu Ile Val Leu Thr Gln Ser Pro Ala Thr Met Ser Ala Ser Pro Gly
1               5                   10                  15 gaa cga gtg acc atg act tgt aca gta tcc tcc tct gtg aac tct tct     96
Glu Arg Val Thr Met Thr Cys Thr Val Ser Ser Ser Val Asn Ser Ser
            20                  25                  30 tac ctg cat tgg tac cag cag aag cct ggt tcc agc ccc aaa ctc tgg    144
Tyr Leu His Trp Tyr Gln Gln Lys Pro Gly Ser Ser Pro Lys Leu Trp
        35                  40                  45 atc tac agt aca agc aat ctg ccc tca ggc gtt ccc gct agg ttc tcc    192
Ile Tyr Ser Thr Ser Asn Leu Pro Ser Gly Val Pro Ala Arg Phe Ser
    50                  55                  60 ggt tca ggt tct ggc act agt tac tct ctg acc atc agc acc atc gaa    240
Gly Ser Gly Ser Gly Thr Ser Tyr Ser Leu Thr Ile Ser Thr Ile Glu
65                  70                  75                  80 tcc gaa gat gct gca aca tac tac tgt cac cag tat cac agg tcc ccc    288
Ser Glu Asp Ala Ala Thr Tyr Tyr Cys His Gln Tyr His Arg Ser Pro
                85                  90                  95 cag ttt aca ttc ggt ggc ggc acc aaa ctt gag att aag cgt            330
Gln Phe Thr Phe Gly Gly Gly Thr Lys Leu Glu Ile Lys Arg
            100                 105                 110

<210> SEQ ID NO 47
<211> LENGTH: 110
<212> TYPE: PRT
<213> ORGANISM: Artificial
<220> FEATURE:
<223> OTHER INFORMATION: Synthetic Construct

<400> SEQUENCE: 47

Glu Ile Val Leu Thr Gln Ser Pro Ala Thr Met Ser Ala Ser Pro Gly
1               5                   10                  15

Glu Arg Val Thr Met Thr Cys Thr Val Ser Ser Ser Val Asn Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Pro Ser Gly Val Pro Ala Arg Phe Ser
    50                  55                  60

Gly Ser Gly Ser Gly Thr Ser Tyr Ser Leu Thr Ile Ser Thr Ile Glu
65                  70                  75                  80

Ser Glu Asp Ala Ala Thr Tyr Tyr Cys His Gln Tyr His Arg Ser Pro
                85                  90                  95
```

Gln Phe Thr Phe Gly Gly Gly Thr Lys Leu Glu Ile Lys Arg
            100                 105                 110

<210> SEQ ID NO 48
<211> LENGTH: 112
<212> TYPE: PRT
<213> ORGANISM: Artificial
<220> FEATURE:
<223> OTHER INFORMATION: Humanized antibody

<400> SEQUENCE: 48

Asp Ile Val Leu Thr Gln Ser Pro Asp Ser Leu Ala Val Ser Leu Gly
1               5                   10                  15

Glu Arg Ala Thr Ile Ser Cys Arg Ala Ser Glu Ser Val Asp Thr Phe
            20                  25                  30

Gly Tyr Ser Phe Ile Tyr Trp Tyr Gln Gln Lys Pro Gly Gln Pro Pro
        35                  40                  45

Arg Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile Asn
65                  70                  75                  80

Pro Val Glu Ala Glu Asp Val Ala Thr Tyr Tyr Cys Gln Gln Ser Asn
                85                  90                  95

Glu Asp Pro Pro Thr Phe Gly Gly Gly Thr Lys Leu Glu Ile Lys Arg
            100                 105                 110

<210> SEQ ID NO 49
<211> LENGTH: 112
<212> TYPE: PRT
<213> ORGANISM: Artificial
<220> FEATURE:
<223> OTHER INFORMATION: Humanized antibody

<400> SEQUENCE: 49

Asp Ile Val Leu Thr Gln Ser Pro Asp Ser Leu Ala Val Ser Leu Gly
1               5                   10                  15

Glu Arg Ala Thr Ile Ser Cys Arg Ala Ser Glu Ser Val Asp Thr Phe
            20                  25                  30

Gly Tyr Ser Phe Ile Tyr Trp Tyr Gln Gln Lys Pro Gly Gln Pro Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Glu Asp Val Ala Thr Tyr Tyr Cys Gln Gln Ser Asn
                85                  90                  95

Glu Asp Pro Pro Thr Phe Gly Gly Gly Thr Lys Leu Glu Ile Lys Arg
            100                 105                 110

<210> SEQ ID NO 50
<211> LENGTH: 112
<212> TYPE: PRT
<213> ORGANISM: Artificial
<220> FEATURE:
<223> OTHER INFORMATION: Humanized antibody

<400> SEQUENCE: 50

Asp Ile Val Leu Thr Gln Ser Pro Asp Ser Leu Ala Val Ser Leu Gly
1               5                   10                  15

```
Glu Arg Ala Thr Ile Ser Cys Arg Ala Ser Glu Ser Val Asp Thr Phe
             20                  25                  30

Gly Tyr Ser Phe Ile Tyr Trp Tyr Gln Gln Lys Pro Gly Gln Pro Pro
         35                  40                  45

Arg Leu Leu Ile Tyr Arg Ala Ser Asn Leu Glu Ser Gly Ile Pro Asp
     50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                 85                  90                  95

Glu Asp Pro Pro Thr Phe Gly Gly Gly Thr Lys Leu Glu Ile Lys Arg
            100                 105                 110

<210> SEQ ID NO 51
<211> LENGTH: 339
<212> TYPE: DNA
<213> ORGANISM: Artificial
<220> FEATURE:
<223> OTHER INFORMATION: Humanized antibody
<220> FEATURE:
<221> NAME/KEY: CDS
<222> LOCATION: (1)..(339)
<220> FEATURE:
<221> NAME/KEY: source
<222> LOCATION: (1)..(69)
<223> OTHER INFORMATION: homo sapiens
<220> FEATURE:
<221> NAME/KEY: source
<222> LOCATION: (70)..(117)
<223> OTHER INFORMATION: Mus sp.
<220> FEATURE:
<221> NAME/KEY: source
<222> LOCATION: (118)..(162)
<223> OTHER INFORMATION: homo sapiens
<220> FEATURE:
<221> NAME/KEY: source
<222> LOCATION: (163)..(183)
<223> OTHER INFORMATION: Mus sp.
<220> FEATURE:
<221> NAME/KEY: source
<222> LOCATION: (184)..(279)
<223> OTHER INFORMATION: homo sapiens
<220> FEATURE:
<221> NAME/KEY: source
<222> LOCATION: (280)..(306)
<223> OTHER INFORMATION: Mus sp.
<220> FEATURE:
<221> NAME/KEY: source
<222> LOCATION: (307)..(339)
<223> OTHER INFORMATION: homo sapiens

<400> SEQUENCE: 51 gac gtc gtg atg aca caa acc cct ctg tcc ctg agc gtc act ctg gga      48
Asp Val Val Met Thr Gln Thr Pro Leu Ser Leu Ser Val Thr Leu Gly
1               5                  10                  15 caa ccc gct tcc att agc tgc aaa tca tca caa tct ctc atc cac tca      96
Gln Pro Ala Ser Ile Ser Cys Lys Ser Ser Gln Ser Leu Ile His Ser
             20                  25                  30 gac ggc aaa aca tac ctc aat tgg ctg ctg cag aga cca gga cag tcc     144
Asp Gly Lys Thr Tyr Leu Asn Trp Leu Leu Gln Arg Pro Gly Gln Ser
         35                  40                  45 cct aaa agg ctt atc tac ctg gtc tct cgt ttg gac tct ggt gta cca     192
Pro Lys Arg Leu Ile Tyr Leu Val Ser Arg Leu Asp Ser Gly Val Pro
     50                  55                  60 gac cgg ttt act ggt tcc ggg gcc gga acc gat ttc act ctg aag att     240
Asp Arg Phe Thr Gly Ser Gly Ala Gly Thr Asp Phe Thr Leu Lys Ile
65                  70                  75                  80
```

```
tcc agg gtg gaa gct gaa gat ctc gga gtg tat tat tgc tgg cag ggc      288
Ser Arg Val Glu Ala Glu Asp Leu Gly Val Tyr Tyr Cys Trp Gln Gly
                85                  90                  95 agc cat ttc ccc cgt act ttt ggt ggg ggt acc aaa ttg gaa att aag      336
Ser His Phe Pro Arg Thr Phe Gly Gly Gly Thr Lys Leu Glu Ile Lys
            100                 105                 110 cgt                                                                  339
Arg

<210> SEQ ID NO 52
<211> LENGTH: 113
<212> TYPE: PRT
<213> ORGANISM: Artificial
<220> FEATURE:
<223> OTHER INFORMATION: Synthetic Construct

<400> SEQUENCE: 52

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Ile His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Arg Leu Asp Ser Gly Val Pro
    50                  55                  60

Asp Arg Phe Thr Gly Ser Gly Ala Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Arg Thr Phe Gly Gly Gly Thr Lys Leu Glu Ile Lys
            100                 105                 110

Arg

<210> SEQ ID NO 53
<211> LENGTH: 36
<212> TYPE: DNA
<213> ORGANISM: Mus sp.

<400> SEQUENCE: 53
ggaggatcca tagacagatg ggggtgtcgt tttggc                               36

<210> SEQ ID NO 54
<211> LENGTH: 32
<212> TYPE: DNA
<213> ORGANISM: Mus sp.

<400> SEQUENCE: 54
ggaggatccc ttgaccaggc atcctagagt ca                                   32

<210> SEQ ID NO 55
<211> LENGTH: 32
<212> TYPE: DNA
<213> ORGANISM: Mus sp.
<220> FEATURE:
<221> NAME/KEY: misc_feature
<222> LOCATION: (1)..(32)
<223> OTHER INFORMATION: mixed bases are defined as follows: H=A+T+C,
      S=G+C, Y=C+T, K=G+T, M=A+C, R=A+G, W=A+T, V = A+C+G,
      N = A+C+G+T

<400> SEQUENCE: 55
cttccggaat tcsargtnma gctgsagsag tc                                   32
```

```
<210> SEQ ID NO 56
<211> LENGTH: 35
<212> TYPE: DNA
<213> ORGANISM: Mus sp.
<220> FEATURE:
<221> NAME/KEY: misc_feature
<222> LOCATION: (18)..(18)
<223> OTHER INFORMATION: n is a, c, g, or t

<400> SEQUENCE: 56
cttccggaat tcsargtnma gctgsagsag tcwgg                               35

<210> SEQ ID NO 57
<211> LENGTH: 31
<212> TYPE: DNA
<213> ORGANISM: Mus sp.
<220> FEATURE:
<221> NAME/KEY: misc_feature
<222> LOCATION: (1)..(31)
<223> OTHER INFORMATION: mixed bases are defined as follows: H=A+T+C,
      S=G+C,  Y=C+T,   K=G+T,   M=A+C,  R=A+G,  W=A+T,   V = A+C+G,
      N = A+C+G+T

<400> SEQUENCE: 57
ggagctcgay attgtgmtsa cmcarwctmc a                                  31

<210> SEQ ID NO 58
<211> LENGTH: 46
<212> TYPE: DNA
<213> ORGANISM: Mus sp.

<400> SEQUENCE: 58
tatagagctc aagcttggat ggtgggaaga tggatacagt tggtgc                  46

<210> SEQ ID NO 59
<211> LENGTH: 23
<212> TYPE: DNA
<213> ORGANISM: Mus sp.

<400> SEQUENCE: 59
gacagacaca ctcctgctat ggg                                           23

<210> SEQ ID NO 60
<211> LENGTH: 32
<212> TYPE: DNA
<213> ORGANISM: Mus sp.
<220> FEATURE:
<221> NAME/KEY: misc_feature
<222> LOCATION: (1)..(32)
<223> OTHER INFORMATION: mixed bases are defined as follows: H=A+T+C,
      S=G+C,  Y=C+T,   K=G+T,   M=A+C,  R=A+G,  W=A+T,   V = A+C+G,
      N = A+C+G+T

<400> SEQUENCE: 60
gcagaattca tgggatggag cyggatcttt ct                                 32

<210> SEQ ID NO 61
<211> LENGTH: 5
<212> TYPE: PRT
<213> ORGANISM: Mus sp.

<400> SEQUENCE: 61

Glu Tyr Asn Met His
1               5
```

```
<210> SEQ ID NO 62
<211> LENGTH: 17
<212> TYPE: PRT
<213> ORGANISM: Mus sp.

<400> SEQUENCE: 62

Tyr Ile Tyr Pro Tyr Asn Gly Asp Thr Gly Tyr Arg Gln Lys Phe Lys
1               5                   10                  15

Asn

<210> SEQ ID NO 63
<211> LENGTH: 11
<212> TYPE: PRT
<213> ORGANISM: Mus sp.

<400> SEQUENCE: 63

Trp Gly Tyr Gly Ser Gly Gly Gly Phe Thr Tyr
1               5                   10

<210> SEQ ID NO 64
<211> LENGTH: 15
<212> TYPE: PRT
<213> ORGANISM: Mus sp.

<400> SEQUENCE: 64

Arg Ala Ser Glu Ser Val Asp Thr Tyr Gly Asn Ser Phe Met His
1               5                   10                  15

<210> SEQ ID NO 65
<211> LENGTH: 7
<212> TYPE: PRT
<213> ORGANISM: Mus sp.

<400> SEQUENCE: 65

Arg Ala Ser Asn Leu Glu Ser
1               5

<210> SEQ ID NO 66
<211> LENGTH: 9
<212> TYPE: PRT
<213> ORGANISM: Mus sp.

<400> SEQUENCE: 66

Gln Gln Ser Asn Glu Asp Pro Leu Thr
1               5

<210> SEQ ID NO 67
<211> LENGTH: 5
<212> TYPE: PRT
<213> ORGANISM: Mus sp.

<400> SEQUENCE: 67

Asp Tyr Asn Met His
1               5

<210> SEQ ID NO 68
<211> LENGTH: 17
<212> TYPE: PRT
<213> ORGANISM: Mus sp.

<400> SEQUENCE: 68

Phe Ile Tyr Pro Tyr Asn Gly Gly Thr Gly Tyr Asn Gln Arg Phe Lys
1               5                   10                  15

Asn
```

<210> SEQ ID NO 69
<211> LENGTH: 10
<212> TYPE: PRT
<213> ORGANISM: Mus sp.

<400> SEQUENCE: 69

Gly Tyr Tyr Tyr Gly Arg His Phe Asp Tyr
1               5                   10

<210> SEQ ID NO 70
<211> LENGTH: 10
<212> TYPE: PRT
<213> ORGANISM: Mus sp.

<400> SEQUENCE: 70

Ser Ala Ser Ser Val Ser Tyr Met Tyr
1               5                   10

<210> SEQ ID NO 71
<211> LENGTH: 7
<212> TYPE: PRT
<213> ORGANISM: Mus sp.

<400> SEQUENCE: 71

Ile Thr Ser Asn Leu Ala Ser
1               5

<210> SEQ ID NO 72
<211> LENGTH: 9
<212> TYPE: PRT
<213> ORGANISM: Mus sp.

<400> SEQUENCE: 72

Gln Gln Trp Ser Ser Asn Pro Pro Thr
1               5

<210> SEQ ID NO 73
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 73

```
gag gtc cag ctt cag cag tca gga cct gac ctg gtg aaa cct ggg gcc      48
Glu Val Gln Leu Gln Gln Ser Gly Pro Asp Leu Val Lys Pro Gly Ala
1               5                   10                  15 tca gtg aag ata tcc tgc aag gct tct gga tac aga ttc act gaa tac      96
Ser Val Lys Ile Ser Cys Lys Ala Ser Gly Tyr Arg Phe Thr Glu Tyr
            20                  25                  30 aat atg cac tgg atg aag cag agc cat gga gag agc ctt gag tgg att     144
Asn Met His Trp Met Lys Gln Ser His Gly Glu Ser Leu Glu Trp Ile
        35                  40                  45 gga tat att tat cct tac aat ggt gat act ggc tac agg cag aaa ttc     192
Gly Tyr Ile Tyr Pro Tyr Asn Gly Asp Thr Gly Tyr Arg Gln Lys Phe
    50                  55                  60 aag aac atg gcc aca ttg act gca gac att tcc tcc aat aca gcc tac     240
Lys Asn Met Ala Thr Leu Thr Ala Asp Ile Ser Ser Asn Thr Ala Tyr
65                  70                  75                  80 atg gaa ctc cgc agc ctg aca tct gac gac tct gca gtc tat ttc tgt     288
Met Glu Leu Arg Ser Leu Thr Ser Asp Asp Ser Ala Val Tyr Phe Cys
                85                  90                  95
```

```
gca aga tgg ggc tac ggt agt ggc ggg ggg ttt act tac tgg ggc caa        336
Ala Arg Trp Gly Tyr Gly Ser Gly Gly Gly Phe Thr Tyr Trp Gly Gln
            100                 105                 110 ggg act ctg gtc act gtc tct gca                                        360
Gly Thr Leu Val Thr Val Ser Ala
        115                 120

<210> SEQ ID NO 74
<211> LENGTH: 120
<212> TYPE: PRT
<213> ORGANISM: Mus sp.

<400> SEQUENCE: 74

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Arg Phe Thr Glu Tyr
            20                  25                  30

Asn Met His Trp Met Lys Gln Ser His Gly Glu Ser Leu Glu Trp Ile
        35                  40                  45

Gly Tyr Ile Tyr Pro Tyr Asn Gly Asp Thr Gly Tyr Arg Gln Lys Phe
    50                  55                  60

Lys Asn Met Ala Thr Leu Thr Ala Asp Ile Ser Ser Asn Thr Ala Tyr
65                  70                  75                  80

Met Glu Leu Arg Ser Leu Thr Ser Asp Asp Ser Ala Val Tyr Phe Cys
                85                  90                  95

Ala Arg Trp Gly Tyr Gly Ser Gly Gly Gly Phe Thr Tyr Trp Gly Gln
            100                 105                 110

Gly Thr Leu Val Thr Val Ser Ala
        115                 120

<210> SEQ ID NO 75
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 75 gag gtc cag ctt cag cag tca gga cct gag ctg gtg aaa cct ggg gcc        48
Glu Val Gln Leu Gln Gln Ser Gly Pro Glu Leu Val Lys Pro Gly Ala
1               5                   10                  15 tca gtg aag ata tcc tgc aag gct tct gga tac aca ttc act gac tac        96
Ser Val Lys Ile Ser Cys Lys Ala Ser Gly Tyr Thr Phe Thr Asp Tyr
            20                  25                  30 aac atg cac tgg gtg aaa cag agc cat gga aag agc ctt gag tgg att        144
Asn Met His Trp Val Lys Gln Ser His Gly Lys Ser Leu Glu Trp Ile
        35                  40                  45 gga ttt att tat cct tac aat ggt ggt act ggc tac aac cag agg ttc        192
Gly Phe Ile Tyr Pro Tyr Asn Gly Gly Thr Gly Tyr Asn Gln Arg Phe
    50                  55                  60 aag aac aag gcc aca ttg act gta gac act tcc tcc agc aca gcc tac        240
Lys Asn Lys Ala Thr Leu Thr Val Asp Thr Ser Ser Ser Thr Ala Tyr
65                  70                  75                  80 atg gag gtc cgc agc ctg aca tct gag gac tct gca gtc tat ttc tgt        288
Met Glu Val Arg Ser Leu Thr Ser Glu Asp Ser Ala Val Tyr Phe Cys
                85                  90                  95 gca agg gga tat tac tac ggt agg cac ttt gac tac tgg ggc caa ggc        336
Ala Arg Gly Tyr Tyr Tyr Gly Arg His Phe Asp Tyr Trp Gly Gln Gly
            100                 105                 110
```

```
acc act ctc aca gtc tcc tca                                          357
Thr Thr Leu Thr Val Ser Ser
        115

<210> SEQ ID NO 76
<211> LENGTH: 119
<212> TYPE: PRT
<213> ORGANISM: Mus sp.

<400> SEQUENCE: 76

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Phe Ile Tyr Pro Tyr Asn Gly Gly Thr Gly Tyr Asn Gln Arg Phe
    50                  55                  60

Lys Asn Lys Ala Thr Leu Thr Val Asp Thr Ser Ser Ser Thr Ala Tyr
65                  70                  75                  80

Met Glu Val Arg Ser Leu Thr Ser Glu Asp Ser Ala Val Tyr Phe Cys
                85                  90                  95

Ala Arg Gly Tyr Tyr Tyr Gly Arg His Phe Asp Tyr Trp Gly Gln Gly
            100                 105                 110

Thr Thr Leu Thr Val Ser Ser
        115

<210> SEQ ID NO 77
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 77 gac att gtg ctg acc caa tct cca ggt tct ttg gct gtg tct cta ggg    48
Asp Ile Val Leu Thr Gln Ser Pro Gly Ser Leu Ala Val Ser Leu Gly
1               5                   10                  15 cag agg gcc acc ata tcc tgc aga gcc agt gaa agt gtt gac act tat    96
Gln Arg Ala Thr Ile Ser Cys Arg Ala Ser Glu Ser Val Asp Thr Tyr
            20                  25                  30 ggc aat agt ttc atg cac tgg tac cag cag aaa gca gga cag ccg ccc   144
Gly Asn Ser Phe Met His Trp Tyr Gln Gln Lys Ala Gly Gln Pro Pro
        35                  40                  45 aga ctc ctc atc tat cgt gca tcc aac cta gaa tct ggg atc cct gcc   192
Arg Leu Leu Ile Tyr Arg Ala Ser Asn Leu Glu Ser Gly Ile Pro Ala
    50                  55                  60 agg ttc agt ggc agt ggg tct agg aca gac ttc acc ctc acc att aat   240
Arg Phe Ser Gly Ser Gly Ser Arg Thr Asp Phe Thr Leu Thr Ile Asn
65                  70                  75                  80 cct gtg gag gct gat gat gtt gca acc tat tac tgt cag caa agt aat   288
Pro Val Glu Ala Asp Asp Val Ala Thr Tyr Tyr Cys Gln Gln Ser Asn
                85                  90                  95 gag gat cct ctc acg ttc ggt gct ggg acc aag ctg gag ctg aaa cgg   336
Glu Asp Pro Leu Thr Phe Gly Ala Gly Thr Lys Leu Glu Leu Lys Arg
            100                 105                 110

<210> SEQ ID NO 78
<211> LENGTH: 112
```

<210> SEQ ID NO 78
<211> LENGTH: 113 (implied)
<212> TYPE: PRT
<213> ORGANISM: Mus sp.

<400> SEQUENCE: 78

```
Asp Ile Val Leu Thr Gln Ser Pro Gly Ser Leu Ala Val Ser Leu Gly
1               5                   10                  15
Gln Arg Ala Thr Ile Ser Cys Arg Ala Ser Glu Ser Val Asp Thr Tyr
            20                  25                  30
Gly Asn Ser Phe Met His Trp Tyr Gln Gln Lys Ala Gly Gln Pro Pro
        35                  40                  45
Arg Leu Leu Ile Tyr Arg Ala Ser Asn Leu Glu Ser Gly Ile Pro Ala
    50                  55                  60
Arg Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Asn
                85                  90                  95
Glu Asp Pro Leu Thr Phe Gly Ala Gly Thr Lys Leu Glu Leu Lys Arg
            100                 105                 110
```

<210> SEQ ID NO 79
<211> LENGTH: 321
<212> TYPE: DNA
<213> ORGANISM: Mus sp.
<220> FEATURE:
<221> NAME/KEY: CDS
<222> LOCATION: (1)..(321)

<400> SEQUENCE: 79

```
caa att gtt ctc acc cag tct cca gca ctc atg tct gca tct ccc ggg      48
Gln Ile Val Leu Thr Gln Ser Pro Ala Leu Met Ser Ala Ser Pro Gly
1               5                   10                  15 gag aag gtc acc atg acc tgc agt gcc agc tca agt gtg agt tac atg      96
Glu Lys Val Thr Met Thr Cys Ser Ala Ser Ser Ser Val Ser Tyr Met
            20                  25                  30 tac tgg tac cag cag aag cca aga tcc tcc ccc aaa ccc tgg att tat     144
Tyr Trp Tyr Gln Gln Lys Pro Arg Ser Ser Pro Lys Pro Trp Ile Tyr
        35                  40                  45 atc aca tcc aac ctg gct tct gga gtc cct gct cgc ttc agt ggc agt     192
Ile Thr Ser Asn Leu Ala Ser Gly Val Pro Ala Arg Phe Ser Gly Ser
    50                  55                  60 ggg tct ggg acc tct tac tct ctc aca atc agc agc atg gag gct gaa     240
Gly Ser Gly Thr Ser Tyr Ser Leu Thr Ile Ser Ser Met Glu Ala Glu
65                  70                  75                  80 gat gct gcc act tat tac tgc cag cag tgg agt agt aac cca ccc acg     288
Asp Ala Ala Thr Tyr Tyr Cys Gln Gln Trp Ser Ser Asn Pro Pro Thr
                85                  90                  95 ttc gga ggg ggg acc aag ctg gaa ata aaa cgg                         321
Phe Gly Gly Gly Thr Lys Leu Glu Ile Lys Arg
            100                 105
```

<210> SEQ ID NO 80
<211> LENGTH: 107
<212> TYPE: PRT
<213> ORGANISM: Mus sp.

<400> SEQUENCE: 80

```
Gln Ile Val Leu Thr Gln Ser Pro Ala Leu Met Ser Ala Ser Pro Gly
1               5                   10                  15
Glu Lys Val Thr Met Thr Cys Ser Ala Ser Ser Ser Val Ser Tyr Met
            20                  25                  30
```

```
Tyr Trp Tyr Gln Gln Lys Pro Arg Ser Ser Pro Lys Pro Trp Ile Tyr
        35              40              45

Ile Thr Ser Asn Leu Ala Ser Gly Val Pro Ala Arg Phe Ser Gly Ser
    50              55              60

Gly Ser Gly Thr Ser Tyr Ser Leu Thr Ile Ser Ser Met Glu Ala Glu
65              70              75              80

Asp Ala Ala Thr Tyr Tyr Cys Gln Gln Trp Ser Ser Asn Pro Pro Thr
            85              90              95

Phe Gly Gly Gly Thr Lys Leu Glu Ile Lys Arg
            100             105
```

METHODS OF USE FOR ANTIBODIES THAT SPECIFICALLY BIND TO THE EPHA2 RECEPTOR

RELATED APPLICATIONS

This application is a Continuation of U.S. patent application Ser. No. 12/373,574, filed Oct. 2, 2009, which issued as U.S. Pat. No. 8,460,667 on Jun. 11, 2013, which is a 35 U.S.C. §371 filing of International Patent Application No: PCT/IB2007/003074, filed Jul. 13, 2007, which claims priority to European Patent Application No.: 06291160.7, filed Jul. 18, 2006. The entire contents of each of the above documents are incorporated herein by reference.

FIELD OF THE INVENTION

The present invention provides novel murine anti-Eph monoclonal antibodies or fragments thereof, and humanized or resurfaced versions thereof. More specifically, the invention relates to novel monoclonal antibodies or fragments thereof, and humanized or resurfaced versions thereof, which interact with the EphA receptor family and act as antagonists. More particularly, the invention relates to anti-EphA2 receptor antibodies that inhibit the cellular functions of the EphA2 receptor. Still more particularly, the invention relates to anti-EphA2 receptor antibodies that antagonize growth and survival of tumor cells and which are devoid of agonist activity.

The present invention is further directed to cytotoxic conjugates comprising a cell binding agent and a cytotoxic agent, therapeutic compositions comprising the conjugate, methods for using the conjugates in the inhibition of cell growth and the treatment of disease, and a kit comprising the cytotoxic conjugate. In particular, the cell binding agent is a monoclonal antibody, or epitope-binding fragment thereof, and a humanized or resurfaced version thereof that recognizes and binds the EphA family of receptors.

BACKGROUND OF THE INVENTION

Receptor tyrosine kinases play a diverse role in cell growth and differentiation during normal physiologic responses and in oncogenic transformation and tumor progression. Eph receptors are a unique family of receptor tyrosine kinases (RTK), the largest in the genome, consisting of at least 16 receptors that interact with nine membrane-bound ephrin ligands (Pasquale, E. B. et al., 2005, *Nature Reviews Mol. Cell. Biol.*, 6: 462-475). They can be further divided into two groups, class A and B, based on the sequence homology and binding affinity (Pasquale, E. B. et al., 2005, *Nature Reviews Mol. Cell. Biol.*, 6: 462-475). Class A Eph receptors interact with multiple ligands of the ephrin-A family, a group of glycosyl-phosphatidylinositol (GPI)-linked membrane proteins, while class B Eph receptors bind to ephrin-B ligands, a family of transmembrane proteins. Binding of Eph receptors to their ligands induces receptor clustering, activation of kinase activity, and subsequent trans-phosphorylation of the cytoplasmic domains on tyrosine residues, creating docking sites for a number of signaling proteins (Kullander, K. and Klein, R., 2002, *Nature Reviews Mol. Cell. Biol.*, 3: 475-486; Noren, N. K. and Pasquale, E. B., 2004, *Cell signal.*, 16: 655-666).

Cancer is a disease characterized by uncontrolled proliferation, resulting from aberrant signal transduction. The most dangerous forms of cancer are malignant cells which have the ability of these to spread, either by direct growth into adjacent tissue through invasion, or by implantation into distant sites by metastasis. Metastatic cells have acquired the ability to break away from the primary tumor, translocate to distant sites through the bloodstream or lymphatic system, and colonize distant and foreign microenvironments.

It is now clear that the Eph molecules also have a role in disease states such as cancer. In particular, overexpression of the EphA2 receptor has been reported in cancers of the ovary, breast, prostate, lung, colon, oesophagus, renal cell, cervix, and melanoma. EphA2 was suggested to be a positive regulator of cell growth and survival in malignant cells (Landen, C. N. et al., 2005, *Expert. Opin. Ther. Targets*, 9 (6): 1179-1187). A role for EphA2 in metastasis has also been described, since EphA2 overexpression alone is sufficient to transform mammary epithelial cells into a malignant phenotype (Zelinski et al., 2001, *Cancer Res.*, 61: 2301-2306), and increases spontaneous metastasis to distant sites (Landen, C. N. et al., 2005, *Expert. Opin. Ther. Targets*, 9 (6): 1179-1187). Furthermore, increasing evidence suggests that EphA2 is involved in tumor angiogenesis (Ogawa et al., 2000, *Oncogene*, 19: 6043-6052; Cheng et al. 2002, *Mol. Cancer. Res.*, 1: 2-11; Cheng et al., 2003, *Neoplasia*, 5 (5): 445-456; Dobrzanski et al., 2004, *Cancer Res.*, 64: 910-919).

Phosphorylation of EphA2 has been shown to be linked to its abundance. Tyrosine phosphorylated EphA2 is rapidly internalised and fated for degradation, whereas unphosphorylated EphA2 demonstrates reduced turnover and therefore accumulates at the cell surface. It is currently thought that this kind of model might contribute to the high frequency of EphA2 overexpression in cancer (Landen, C. N. et al., 2005, *Expert. Opin. Ther. Targets*, 9 (6): 1179-1187). However, reality may be more complex, since recent data seem to indicate a role for EphA2 kinase-dependent and -independent functions in tumor progression (Fang W. B., 2005, *Oncogene*, 24: 7859-7868).

Agonistic antibodies have been developped which promote EphA2 tyrosine phosphorylation and internalisation, ultimately resulting in inhibition of tumor cell growth (Dodge-Zantek et al., 1999, *Cell Growth & Differ.*, 10: 629-638; WO 01/12172, WO 03/094859, WO 2004/014292, WO 2004/101764, WO 2006/023403, WO 2006/047637, WO 2007/030642). These antibodies are directed against the extracellular domain of EphA2. Since these agonist antibodies do not inhibit but rather stimulate EphA2 receptor phosphorylation and downstream signals, these antibodies might not be effective for tumors which take advantage of the EphA2 kinase activity. On the other hand, the use of antagonistic agents, including antibodies, has been proposed (WO 2004/092343), but no actual antagonistic antibody was disclosed therein. Moreover, such antibodies were proposed to stimulate, rather than inhibit, cell proliferation. Application WO 2006/084226 discloses antibodies which neither increase nor decrease EphA2 kinase activity but are capable of impeding tumor cell proliferation. However, there is no indication therein that these antibodies prevent ephrinA1 binding to the receptor and inhibit ephrinA1-induced EphA2 phosphorylation. Rather, they may affect tumor cell proliferation through a totally different mechanism, e.g. by preventing receptor clustering following ephrinA1 binding. The skilled person would thus not have concluded that these antibodies are antagonists, but, rather, that their mechanism of action is unclear.

Therefore, there is a need for new, antagonistic anti-EphA2 antibodies, which bind to the extracellular domains of EphA2 receptor, inhibit its activation by the ligand ephrin A1 and inhibit EphA2 kinase-dependend tumor cell growth. Such antagonistic antibodies should be useful for the treatment of cancer.

SUMMARY OF THE INVENTION

Accordingly, it is an object of the invention to provide agents that specifically bind to class A Eph receptor family members, such as EphA2, and inhibit the cellular activity of the receptor by antagonizing the receptor. Thus, the present invention includes antibodies or fragments thereof that recognize the EphA2 receptor, preferably human, and function as antagonists of said receptor.

The EphA2 receptor has a role in the development and the growth of tumors, and has also been involved in metastasis. In some embodiments, the antibodies of the invention are capable of inhibiting the growth of a cancer cell. In some other embodiments, the antibodies of the invention are capable of preventing the migration of metastatic cancer cells. In preferred embodiments, the cancer cell is a cell of a cancer selected from the group consisting of a breast cancer, colon cancer, endometrial cancer, ovarian carcinoma, osteosarcoma, cervical cancer, prostate cancer, lung cancer, synovial carcinoma pancreatic cancer, a sarcoma, a glioma, head and neck cancer, gastric cancer, liver cancer, and other carcinomas. In another embodiment, the antibodies of the invention are capable of inhibiting angiogenesis.

Whereas the anti-EphA2 antibodies disclosed in the prior art were mostly agonists (e.g. WO 03/094859, WO 2004/014292, WO 2004/101764, WO 2006/023403, WO 2006/047637, WO 2007/030642), this invention encompasses antibodies recognizing said receptor which have minimal agonistic activity, or, preferentially, which are devoid of any agonist activity towards the receptor. In a preferred embodiment, the antibodies of the invention do not stimulate EphA2 tyrosine phosphorylation.

The antibodies of the invention are capable of inhibiting the binding of a ligand, preferably ephrin A1, to the EphA2 receptor. In some embodiments, they are capable of inhibiting EphA2 tyrosine phosphorylation. In another embodiment, EphA2 tyrosine phosphorylation is inhibited by the antibodies of the invention even in the presence of ephrinA1. In some embodiments, antibodies of the invention can block EphA2-mediated signaling; in particular, they are capable of inhibiting EphA2-dependent phosphorylation of Akt.

This invention also provides antibodies which bind the EphA2 receptor with a $K_D$ of $0.3 \times 10^{-9}$ M or smaller.

Antibodies of the invention can be polyclonal or monoclonal. Epitope-binding fragments such as Fab, Fab', F(ab')$_2$, or Fv fragments are included within the scope of this invention. Preferred are monoclonal anti-EphA2 antibodies. In a more preferred embodiment, there are provided murine antibodies selected from 37.3D7; 37.1F5; 53.2H11; EphA2-N1; and EphA2-N2, which are fully characterized herein with respect to the amino acid sequences of both their light and heavy chain variable regions, the cDNA sequences of the genes for the light and heavy chain variable regions, the identification of their CDRs (complementarity-determining regions), the identification of their surface amino acids, and means for their expression in recombinant form. The hybridoma producing murine anti-EphA2 monoclonal antibodies 37.3D7, 37.1F5, and 53.2H11, and EphA2-N1 and EphA2-N2 have been deposited under the Budapest Treaty on Jun. 16, 2006 and on May 3$^{rd}$, 2007, respectively, at the American Type Culture Collection, 10801 University Boulevard, Manassas, Va. 20110-2209, USA, under the accession numbers PTA-7660, PTA-7661, PTA-7662, PTA-8407, and PTA-8408, respectively.

The present invention includes the murine anti-EphA2 monoclonal antibody selected from 37.3D7, 37.1F5, 53.2H11, EphA2-N1, and EphA2-N2, and resurfaced or humanized versions of the 37.3D7, 37.1F5, 53.2H11, EphA2-N1, and EphA2-N2 antibodies wherein surface-exposed residues of the variable region frameworks of the antibodies, or their epitope-binding fragments, are replaced in both light and heavy chains to more closely resemble known human antibody surfaces. The humanized antibodies and epitope-binding fragments thereof of the present invention have improved properties in that they are less immunogenic (or completely non-immunogenic) than murine versions in human subjects to which they are administered. Thus, the different versions of humanized 37.3D7; 37.1F5; 53.2H11; EphA2-N1; and EphA2-N2 antibodies and epitope-binding fragments thereof of the present invention specifically recognize EphA2 receptor while not being immunogenic to a human.

The humanized versions of the 37.3D7, 37.1F5, 53.2H11, EphA2-N1, and EphA2-N2 antibodies of the present invention are fully characterized herein with respect to their respective amino acid sequences of both light and heavy chain variable regions, the DNA sequences of the genes for the light and heavy chain variable regions, the identification of the complementarity determining regions (CDRs), the identification of their variable region framework surface amino acid residues, and disclosure of a means for their expression in recombinant form.

This invention also contemplates the use of conjugates between cytotoxic conjugates comprising (1) a cell binding agent that recognizes and binds the EphA receptor, such as, EphA2 receptor, and (2) a cytotoxic agent. In the cytotoxic conjugates, the cell binding agent has a high affinity for the EphA receptor (e.g., EphA2 receptor) and the cytotoxic agent has a high degree of cytotoxicity for cells expressing the EphA receptor, such that the cytotoxic conjugates of the present invention form effective killing agents.

In a preferred embodiment, the cell binding agent is an anti-EphA2 antibody (e.g., 37.3D7, 37.1F5, 53.2H11, EphA2-N1, or EphA2-N2) or an epitope-binding fragment thereof, more preferably a humanized anti-EphA2 antibody (e.g., 37.3D7, 37.1F5, 53.2H11, EphA2-N1, or EphA2-N2) or an epitope-binding fragment thereof, wherein a cytotoxic agent is covalently attached, directly or via a cleavable or non-cleavable linker, to the antibody or epitope-binding fragment thereof. In more preferred embodiments, the cell binding agent is the humanized 37.3D7; 37.1F5; 53.2H11; EphA2-N1; and EphA2-N2 antibodies or an epitope-binding fragment thereof, and the cytotoxic agent is a taxol, a maytansinoid, a tomaymycin derivative, a leptomycin derivative, CC-1065 or a CC-1065 analog.

In preferred embodiments of the invention, the cell binding agent is the humanized anti-EphA2 antibody 37.3D7, 37.1F5, 53.2H11, EphA2-N1, or EphA2-N2 and the cytotoxic agent is a maytansine compound, such as DM1 or DM4.

The present invention also encompasses the use of fragments of anti-EphA2 antibodies which retain the ability to bind the EphA2 receptor. In another aspect of the invention, the use of functional equivalents of anti-EphA2 antibodies is contemplated.

The present invention also includes a method for inhibiting the growth of a cell expressing the EphA2 receptor. In preferred embodiments, the method for inhibiting the growth of the cell expressing the EphA2 receptor takes place in vivo and results in the death of the cell, although in vitro and ex vivo applications are also included.

The present invention also provides a therapeutic composition comprising an anti-EphA2 antibody or an anti-EphA2 antibody-cytotoxic agent conjugate, and a pharmaceutically acceptable carrier or excipients. In some embodiments, the therapeutic composition comprises a second therapeutic agent. This second therapeutic agent can be chosen from the group comprising the antagonists of fibroblast-growth factor (FGF), hepatocyte growth factor (HGF), tissue factor (TF), protein C, protein S, platelet-derived growth factor (PDGF), or HER2 receptor.

The present invention further includes a method of treating a subject having cancer using the therapeutic composition. In some embodiments, the cancer is a metastatic cancer. In particular, the cancer cell is a cell of a cancer selected from the group consisting of breast cancer, colon cancer, endometrial cancer, ovarian carcinoma, osteosarcoma, cervical cancer, prostate cancer, lung cancer, synovial carcinoma pancreatic cancer, a sarcoma, a glioma, head and neck cancer, gastric cancer, liver cancer, and other carcinomas. In preferred embodiments, the cytotoxic conjugate comprises an anti-EphA2 antibody and a cytotoxic agent. In more preferred embodiments, the cytotoxic conjugate comprises a humanized 37.3D7, 37.1F5, 53.2H11, EphA2-N1, and EphA2-N2 antibody-DM1 conjugate, humanized 37.3D7, 37.1F5, 53.2H11, EphA2-N1, and EphA2-N2 antibody-DM4, a humanized 37.3D7, 37.1F5, 53.2H11, EphA2-N1, and EphA2-N2 antibody-taxane conjugate, or a humanized 37.3D7, 37.1F5, 53.2H11, EphA2-N1, and EphA2-N2 antibody-tomaymycin derivative conjugate, and the conjugate is administered along with a pharmaceutically acceptable carrier or excipients.

In another aspect of the invention, anti-EphA2 antibodies are used to detect the EphA2 protein in a biological sample. In a preferred embodiment, said antibodies are used to determine EphA2 levels in a tumor tissue.

The present invention also includes a kit comprising an anti-EphA2 antibody or an anti-EphA2 antibody-cytotoxic agent conjugate and instructions for use. In preferred embodiments, the anti-EphA2 antibodies are the humanized 37.3D7, 37.1F5, 53.2H11, EphA2-N1, and EphA2-N2 antibodies, the cytotoxic agent is a maytansine compound, such as DM1 or DM4, a taxane, a leptomycin derivative, or a tomaymycin derivative, and the instructions are for using the conjugates in the treatment of a subject having cancer. The kit may also include components necessary for the preparation of a pharmaceutically acceptable formulation, such as a diluent if the conjugate is in a lyophilized state or concentrated form, and for the administration of the formulation.

Unless otherwise stated, all references and patents cited herein are incorporated by reference.

BRIEF DESCRIPTION OF THE FIGURES

FIG. 3 shows binding curves for the antibodies 37.3D7 (FIG. 3A), 37.1F5 (FIG. 3B), and 53.2H11 (FIG. 3C) established with human EphA2 overexpressing murine 300-19 cells (300-19/hu-EphA2).

FIG. 4 shows the specific binding of purified 37.3D7 and 53.2H11 antibodies to cells overexpressing EphA2. Histograms of FACS analysis are shown.

FIG. 7A shows the inhibition of ephrinA1-stimulated EphA2-phosphorylation in mammary MDA-MB-231 cells by 37.3D7 and 37.1F5 antibodies.

FIG. 7B shows the inhibition of ephrinA1-stimulated EphA2-phosphorylation in mammary MDA-MB-231 cells by 37.3D7 and 53.2H11 antibodies.

FIG. 7C shows the inhibition of ephrinA1-stimulated Akt phosphorylation in pancreatic CFPAC-1 cells by 37.3D7 and 37.1F5 antibodies.

FIGS. 8A and B show the stimulation of EphA2-phosphorylation by ephrinA1 and the absence of stimulation of EphA2-phosphorylation by the antibodies 37.3D7, 37.1F5, and 53.2H11 in mammary MDA-MB-231 cells.

FIGS. 9A-9D show the inhibition of serum-stimulated growth and survival of colon HT-29 cells (9A), colon LoVo cells (9B), pancreatic CFPAC-1 cells (9C) and melanoma UACC-257 cells (9D) by 37.3D7 and 53.2H11 antibodies.

DETAILED DESCRIPTION OF THE INVENTION

Figure 1A:
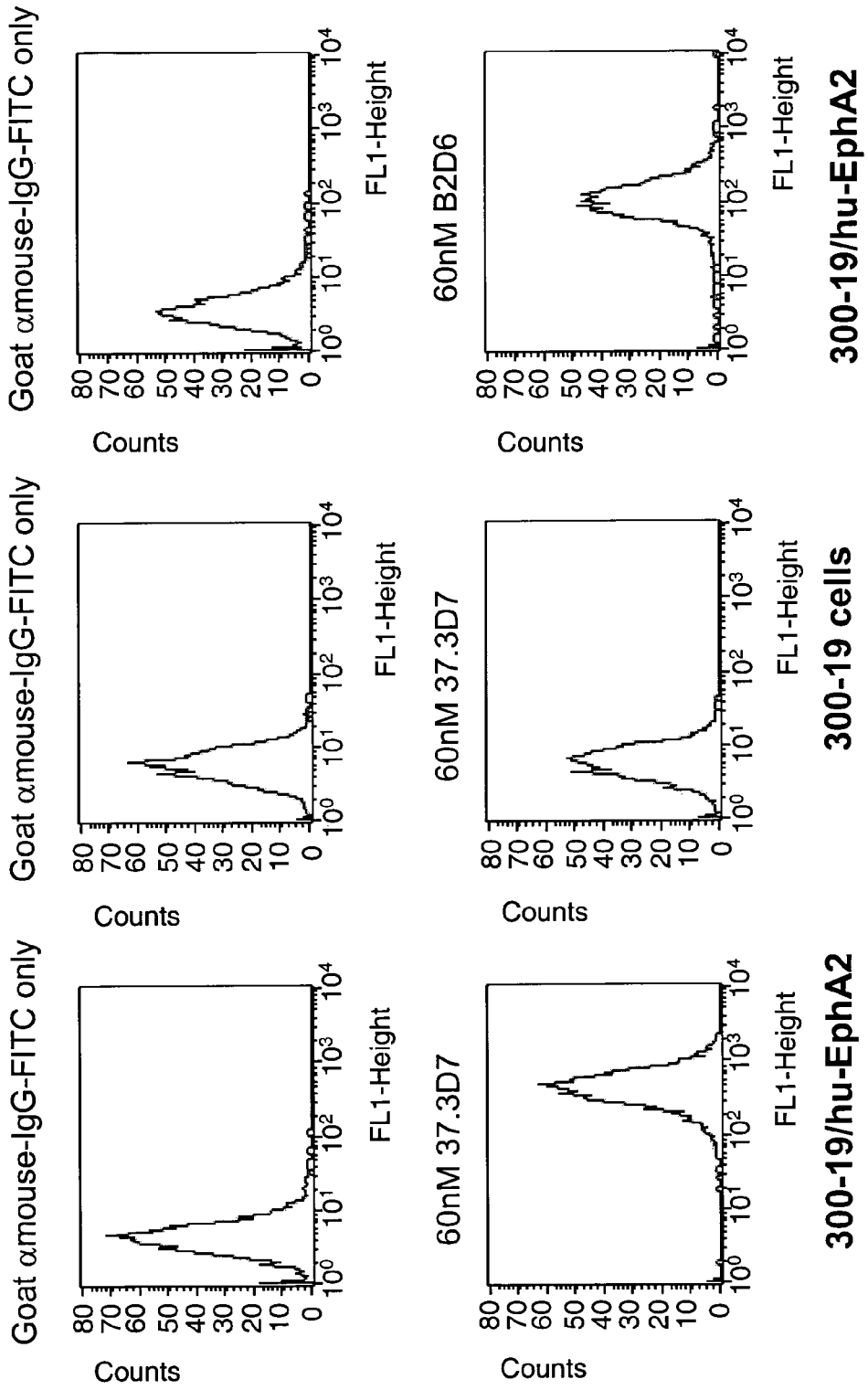
FIG. 1A shows the data for the 37.3D7 antibody, FIG. 1B for the 37.1F5 antibody, and FIG. 1C for the 53.2H11 antibody, respectively.

New agents capable to specifically bind EphA receptors and antagonize said receptors are herein provided. In particular, the present inventors have discovered novel antibodies that specifically bind to EphA receptors on the cell surface. While previously known antibodies which specifically bind the EphA receptor also activate it even in the absence of its ligands, the antibodies or fragments of the present invention are preferentially devoid of any agonist activity. On the other hand, they have the unique ability to inhibit the cellular functions of the receptor even in the presence of its ligands, a characteristic which is totally absent from the previously known EphA2-binding antibodies. Furthermore, the antagonistic antibodies and antibody fragments of the present invention inhibit the growth and/or the migration of human tumor cells, and/or angiogenesis, three properties totally unanticipated in view of the prior art (Landen, C. N. et al., 2005, Expert. Opin. Ther. Targets, 9 (6): 1179-1187; WO 01/12172; WO 2004/014292; WO 2004/092343).

As used herein, the term "Eph receptor" refers to a tyrosine kinase belonging to the Eph receptors family (reviewed in Pasquale, E. B. et al., 2005, Nature Reviews Mol. Cell. Biol., 6, 462-475). "Class A Eph receptor family" or "EphA receptors" as used herein preferentially interact with glycosylphosphatidylinositol (GPI)-linked ligands (of the Ephrin-A subclass, which presently comprises five ligands). Specific EphA receptors include: EphA1 (also called Eph and Esk); EphA2 (also called Eck, mEck, Myk2, Sek2); EphA3 (also termed Hek, Mek4, Tyro4 and Cek4); EphA4 (also known as Hek8, Sek1, Tyro1, and Cek8); EphA5 (also called Hek7, Bsk, Ehk1, Rek7 and Cek7); EphA6 (also called mEhk2 and Ehk2); EphA7 (otherwise named Hek11, Mdk1, Ebk, Ehk3); and EphA8 (also termed Eek and mEek) and naturally occurring variants thereof. The preferred Eph receptor herein is the "EphA2 receptor", comprising, for example, an amino sequence as in Genbank accession Nos NM_004431 (human EphA2), NM_010139 (murine EphA2), or NXM_345596 (rat EphA2). The term "Eph ligand" as used herein refers to a protein that binds to, and optionnally activates (e.g. stimulates the autophosphorylation of), an Eph receptor. A preferred Eph ligand herein is "ephrinA1", which binds to the EphA2 receptor and comprises, for example, an amino sequence as in Genbank accession NM_004428 (human ephrinA1).

The term "antagonist" as used herein refers to a molecule which is capable of inhibiting one or more of the biological activities of a target molecule, such as an EphA receptor. Antagonists may act by interfering with the binding of a receptor to a ligand and vice versa, by decreasing EphA2 phosphorylation, and/or by incapacitating or killing cells which have been activated by a ligand. The antagonist may completely block receptor-ligand interactions or may substantially reduce such interactions. All such points of intervention by an antagonist shall be considered equivalent for purposes of this invention. Thus, included within the scope of the invention are antagonists (e.g. neutralizing antibodies) that bind to EphA receptor, Eph ligand or a complex of an Eph receptor and Eph ligand; amino acid sequence variants or derivatives of an EphA receptor or EphA ligand which antagonize the interaction between an EphA receptor and EphA ligand; soluble EphA receptor or soluble EphA ligand, optionally fused to a heterologous molecule such as an immunoglobulin region (e.g. an immunoadhesin); a complex comprising an EphA receptor in association with EphA ligand; synthetic or native sequence peptides which bind to EphA receptor or EphA ligand.

The term "agonist" as used herein refers to any compound, including a protein, a polypeptide, a peptide, an antibody, an antibody fragment, a conjugate, a large molecule, a small molecule, capable of activating one or more of the biological activities of the target molecule. EphA agonists act by stimulating phosphorylation of the protein, thereby triggering degradation of said protein.

Thus in a preferred embodiment the present invention provides, among other features, anti-EphA monoclonal antibodies, anti-EphA humanized antibodies, and fragments of the anti-EphA antibodies. Each of the antibodies and antibody fragments of the present invention is designed to specifically recognize and bind the EphA2 receptor, and acts as an EphA2 receptor antagonist. Moreover, the antagonistic antibodies and antibody fragments of the invention have the unique properties of being able to inhibit the growth of human tumor cells, and/or the migration of metastatic cancer cells, and/or angiogenesis.

A preferred EphA receptor bound by the antagonistic antibodies and antibody fragments of the invention is the EphA2 receptor. Human EphA2 is a preferred EphA2 receptor.

The EphA2 receptor belongs to a family of receptor whose cytoplasmic tail phosphorylation is increased after ligand binding to interact with a variety of adapter and signalling proteins, leading to the activation of different downstream cellular signalling pathways (Kullander, K. and Klein, R., 2002, Nature Reviews Mol. Cell. Biol., 3: 475-486; Noren, N. K. and Pasquale, E. B., 2004, Cell signal., 16: 655-666). As used herein, the term "EphA2-mediated signaling" refers to all the cellular events which occur in response to ligand binding by EphA2. Whereas antibodies disclosed in the prior art agonize the EphA2 receptor, and, in particular, increase the tyrosine phosphorylation of the EphA2 protein, the antibodies and antibody fragments of the invention are preferentially devoid of any such agonistic properties. In particular, they are unable to stimulate EphA2 phoshorylation by themselves.

On the other hand, this invention provides the first actual antagonistic anti-EphA2 antibodies. In one embodiment, the antibodies and antibody fragments of the invention can inhibit the binding of a ligand to an EphA receptor. In a preferred embodiment, the binding of ephrinA1 to EphA2 is prevented by the antibodies and fragments thereof provided by this invention. Remarkably, in another embodiment, the antibodies and antibody fragments of the invention are capable of inhibiting tyrosine phosphorylation of the EphA2 receptor, even in the presence of ephrinA1. Moreover, said antibodies and fragments thereof are capable of inhibiting EphA2-mediated signaling. In particular, Akt ephrinA1-dependent phosphorylation can be prevented by the antibodies and antibody fragments of the invention.

Antibodies

The term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

As used herein, "$V_H$" or "VH" refers to the variable region of an immunoglobulin heavy chain of an antibody, including the heavy chain of an Fv, scFv, dsFv, Fab, Fab', or F(ab')2 fragment. Reference to "$V_L$" or "VL" refers to the variable region of the immunoglobulin light chain of an antibody, including the light chain of an Fv, scFv, dsFv, Fab, Fab', or F(ab')2 fragment.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

An "epitope" is the site on the antigen to which an antibody binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

As used herein, the term "$K_D$" refers to the dissociation constant of a particular antibody/antigen interaction.

The present invention proceeds from murine anti-EphA2 antibodies, herein 37.3D7; 37.1F5; 53.2H11; EphA2-N1; and EphA2-N2 which are fully characterized with respect to the amino acid sequences of both light and heavy chains, the identification of the CDRs, the identification of surface amino acids, and means for their expression in recombinant form. The primary amino acid and DNA sequences of antibodies 37.3D7; 37.1F5; 53.2H11; EphA2-N1; and EphA2-N2 light and heavy chains, and of humanized versions, are disclosed herein.

Antibodies 37.3D7, 37.1F5, 53.2H11, EphA2-N1, and EphA2-N2 are produced by hybridomas respectively designated 37.3D7, 37.1F5, 53.2H11, EphA2-N1, and EphA2-N2, and deposited under the Budapest Treaty on Jun. 16, 2006 and May 3$^{rd}$, 2007, respectively, at the American Type Culture Collection, 10801 University Boulevard, Manassas, Va. 20110-2209, USA, under the accession numbers PTA-7660, PTA-7661 PTA-7662, PTA-8407 and PTA-8408, respectively.

The scope of the present invention is not limited to antibodies and fragments comprising these sequences. Instead, all antibodies and fragments that specifically bind to EphA2 receptor and antagonize the biological activity of the receptor, but which are devoid of agonist activity, fall within the scope of the present invention. Thus, antibodies and antibody fragments may differ from antibody 37.3D7; 37.1F5; 53.2H11; EphA2-N1; and EphA2-N2 or the humanized derivatives in the amino acid sequences of their scaffold, CDRs, light chain and heavy chain, and still fall within the scope of the present invention.

In one embodiment, this invention provides antibodies or epitope-binding fragment thereof comprisings one or more CDRs having an amino acid sequence selected from the group consisting of SEQ ID NOS: 1, 2, 3, 4, 5, 6, 7, 8, 9, 10, 11, 12, 13, 14, 15, 16, 17, 18, 61, 62, 63, 64, 65, 66, 67, 68, 69, 70, 71, and 72.

In a preferred embodiment, the antibodies of the invention comprise at least one heavy chain and at least one light chain, and said heavy chain comprises three sequential CDRs having amino acid sequences selected from the group consisting of SEQ ID NOS: 1, 2, 3, 7, 8, 9, 13, 14, 15, 61, 62, 63, 67, 68, and 69, and said light chain comprises three sequential CDRs having amino acid sequences selected from the group consisting of SEQ ID NOS: 4, 5, 6, 10, 11, 12, 16, 17, 18, 64, 65, 66, 70, 71, and 72.

In a more preferred embodiment, the antibodies of the invention comprise three CDRS having amino acid sequences selected from the group of SEQ ID NOS: 1, 2, 3, 4, 5, and 6. In a further more preferred embodiment, there is provided a 37.3D7 antibody, which comprises at least one heavy chain and at least one light chain, and said heavy chain comprises three sequential CDRs having amino acid sequences consisting of SEQ ID NOS: 1, 2, and 3, and said light chain comprises three sequential CDRs having amino acid sequences consisting of SEQ ID NOS: 4, 5, and 6.

In another more preferred embodiment, the antibodies of the invention comprise three CDRS having amino acid sequences selected from the group of SEQ ID NOS: 7, 8, 9, 10, 11, and 12. In further more preferred embodiment, there is provided a 37.1F5 antibody, which comprises at least one heavy chain and at least one light chain, and said heavy chain comprises three sequential CDRs having amino acid sequences consisting of SEQ ID NOS: 7, 8, and 9, and said light chain comprises three sequential CDRs having amino acid sequences consisting of SEQ ID NOS: 10, 11, and 12.

In another more preferred embodiment, the antibodies of the invention comprise three CDRS having amino acid sequences selected from the group of SEQ ID NOS: 13, 14, 15, 16, 17, and 18. In a further more preferred embodiment, there is provided a 53.2H11, which comprises at least one heavy chain and at least one light chain, and said heavy chain comprises three sequential CDRs having amino acid sequences consisting of SEQ ID NOS: 13, 14, and 15, and said light chain comprises three sequential CDRs having amino acid sequences consisting of SEQ ID NOS: 16, 17, and 18.

In another more preferred embodiment, the antibodies of the invention comprise three CDRS having amino acid sequences selected from the group of SEQ ID NOS: 61, 62, 63, 64, 65, and 66. In a further more preferred embodiment, there is provided a EphA2-N1 antibody, which comprises at least one heavy chain and at least one light chain, and said heavy chain comprises three sequential CDRs having amino acid sequences consisting of SEQ ID NOS: 61, 62, and 63, and said light chain comprises three sequential CDRs having amino acid sequences consisting of SEQ ID NOS: 64, 65, and 66.

In another more preferred embodiment, the antibodies of the invention comprise three CDRS having amino acid sequences selected from the group of SEQ ID NOS: 67, 68, 69, 70, 71, and 72. In a further more preferred embodiment, there is provided a EphA2-N2 antibody, which comprises at least one heavy chain and at least one light chain, and said heavy chain comprises three sequential CDRs having amino acid sequences consisting of SEQ ID NOS: 67, 68, and 69, and said light chain comprises three sequential CDRs having amino acid sequences consisting of SEQ ID NOS: 70, 71, and 72.

In another embodiment, the antibodies of the invention comprises a $V_H$ having an amino acid sequence selected from the group consisting of SEQ ID NOS: 20, 22, 24, 74 and 76. In a preferred embodiment, there is provided a 37.3D7 antibody comprising a $V_H$ having an amino acid sequence consisting of SEQ ID NO 20. In another preferred embodiment, there is provided a 37.1F5 antibody comprising a $V_H$ having an amino acid sequence consisting of SEQ ID NO 22. In another preferred embodiment, there is provided a 53.2H11 antibody comprising a $V_H$ having an amino acid sequence consisting of SEQ ID NO 24. In another preferred embodiment, there is provided a EphA2-N1 antibody comprising a $V_H$ having an amino acid sequence consisting of SEQ ID NO 74. In another preferred embodiment, there is provided a EphA2-N2 antibody comprising a $V_H$ having an amino acid sequence consisting of SEQ ID NO 76.

In another preferred embodiment, the antibodies of the invention comprise a $V_L$ having an amino acid sequence selected from the group consisting of SEQ ID NOS: 26, 28, 30, 78 and 80. In a preferred embodiment, there is provided a 37.3D7 antibody comprising a $V_L$ having an amino acid sequence consisting of SEQ ID NO 26. In another preferred embodiment, there is provided a 37.1F5 antibody comprising a $V_L$ having an amino acid sequence consisting of SEQ ID NO 28. In another preferred embodiment, there is provided a 53.2H11 antibody comprising a $V_L$ having an amino acid sequence consisting of SEQ ID NO 30. In another preferred embodiment, there is provided a EphA2-N1 antibody comprising a $V_L$ having an amino acid sequence consisting of SEQ ID NO 78. In another preferred embodiment, there is provided a EphA2-N2 antibody comprising a $V_L$ having an amino acid sequence consisting of SEQ ID NO 80.

Humanized or Resurfaced 37.3D7; 37.1F5; 53.2H11; EphA2-N1; and EphA2-N2 Antibodies As used herein, the term "humanized antibody" refers to a chimeric antibody which contain minimal sequence derived from non-human immunoglobulin. A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to to an antibody in which the variable region, or a portion thereof, is altered, replaced, or exchanged, so that the constant region is linked to a variable region of a different species, or belonging to another antibody class or subclass.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, *Molecular Immunology* 28(4/5): 489-498; Studnicka G. M. et al., 1994, *Protein Engineering* 7(6): 805-814; Roguska M. A. et al., 1994, *Proc. Natl. Acad. Sci. U.S.A.*, 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814, 318; and international patent application publication numbers WO 98/46645, WO 98/50433, WO 98/24893, WO 98/16654, WO 96/34096, WO 96/33735, and WO 91/10741 (said references incorporated by reference in their entireties).

The present invention provides humanized antibodies or fragments thereof, which recognizes EphA2 receptor and acts as antagonists. In another embodiment, the humanized antibodies or epitope-binding fragments thereof have the additional ability to inhibit growth of a cancer cell expressing the EphA2 receptor. In a further embodiment, the humanized antibody or epitope-binding thereof have the additional ability to inhibit the migration of a metastatic cancer cell expressing the EphA2 receptor.

A preferred embodiment of such a humanized antibody is a humanized 37.3D7; 37.1F5; 53.2H11; EphA2-N1 or EphA2-N2 antibody, or an epitope-binding fragment thereof.

In more preferred embodiments, there are provided resurfaced or humanized versions of the 37.3D7; 37.1F5; 53.2H11; EphA2-N1 and EphA2-N2 antibodies wherein surface-exposed residues of the antibody or its fragments are replaced in both light and heavy chains to more closely resemble known human antibody surfaces. The humanized 37.3D7, 37.1F5; 53.2H11; EphA2-N1 and EphA2-N2 antibodies or epitope-binding fragments thereof of the present invention have improved properties. For example, humanized 37.3D7, 37.1F5; and 53.2H11 antibodies or epitope-binding fragments thereof specifically recognize EphA2 receptor. More preferably, the humanized 37.3D7, 37.1F5, 53.2H11, EphA2-N1, and EphA2-N2 antibodies or epitope-binding fragments thereof have the additional ability to inhibit growth of a cell expressing the EphA2 receptor.

The humanized versions of the 37.3D7, 37.1F5, 53.2H11, EphA2-N1, and EphA2-N2 antibodies are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form. However, the scope of the present invention is not limited to antibodies and fragments comprising these sequences. Instead, all antibodies and fragments that specifically bind to EphA2 receptor are included in the present invention. Preferably, the antibodies and fragments that specifically bind to EphA2 receptor antagonize the biological activity of the receptor. More preferably, such antibodies further are substantially devoid of agonist activity. Thus, antibodies and epitope-binding antibody fragments of the present invention may differ from the 37.3D7, 37.1F5, 53.2H11, EphA2-N1 or EphA2-N2 antibody or the humanized derivatives thereof, in the amino acid sequences of their scaffold, CDRs, and/or light chain and heavy chain, and still fall within the scope of the present invention.

The CDRs of the 37.3D7, 37.1F5, 53.2H11, EphA2-N1 or EphA2-N2 antibodies are identified by modeling and their molecular structures have been predicted. Again, while the CDRs are important for epitope recognition, they are not essential to the antibodies and fragments of the invention. Accordingly, antibodies and fragments are provided that have improved properties produced by, for example, affinity maturation of an antibody of the present invention.

The mouse light chain IgVκ and Jκ germline genes and heavy chain IgVh and Jh germline genes from which 37.3D7, 37.1F5, 53.2H11, EphA2-N1, and EphA2-N2 were likely derived have been identified, as disclosed in the experimental Examples section. Such germline gene sequences are useful to identify somatic mutations in the antibodies, including in the CDRs.

The sequences of the heavy chain and light chain variable regions of the 37.3D7, 37.1F5, 53.2H11, EphA2-N1, and EphA2-N2 antibodies, and the sequences of their CDRs were not previously known and are set forth in this application. Such information can be used to produce humanized versions of the 37.3D7, 37.1F5, 53.2H11, EphA2-N1, and EphA2-N2 antibodies. These humanized anti-EphA antibodies or their derivatives may also be used as the cell binding agent of the present invention.

Thus, in one embodiment, this invention provides humanized antibodies or epitope-binding fragment thereof comprisings one or more CDRs having an amino acid sequence selected from the group consisting of SEQ ID NOS: 1, 2, 3, 4, 5, 6, 7, 8, 9, 10, 11, 12, 13, 14, 15, 16, 17, 18, 61, 62, 63, 64, 65, 66, 67, 68, 69, 70, 71, and 72. In a preferred embodiment, the humanized antibodies of the invention comprise at least one heavy chain and at least one light chain, and said heavy chain comprises three sequential CDRs having amino acid sequences selected from the group consisting of SEQ ID NOS: 1, 2, 3, 7, 8, 9, 13, 14, 15, 61, 62, 63, 67, 68, and 69, and said light chain comprises three sequential CDRs having amino acid sequences selected from the group consisting of SEQ ID NOS: 4, 5, 6, 10, 11, 12, 16, 17, 18, 64, 65, 66, 70, 71, and 72. In a further preferred embodiment, the humanized antibodies of the invention comprise at least one heavy chain and at least one light chain, wherein said heavy chain comprises three sequential CDRs having amino acid sequences represented by SEQ ID NOS: 1, 2, and 3, and wherein said light chain comprises three sequential CDRs having amino acid sequences represented by SEQ ID NOS: 4, 5, and 6. In another further preferred embodiment, the humanized antibodies of the invention comprise at least one heavy chain and at least one light chain, wherein said heavy chain comprises three sequential CDRs having amino acid sequences represented by SEQ ID NOS: 7, 8, and 9, and wherein said light chain comprises three sequential CDRs having amino acid sequences represented by SEQ ID NOS: 10, 11, and 12. In another further preferred embodiment, the humanized antibodies of the invention comprise at least one heavy chain and at least one light chain, wherein said heavy chain comprises three sequential CDRs having amino acid sequences represented by SEQ ID NOS: 13, 14, and 15, and wherein said light chain comprises three sequential CDRs having amino acid sequences represented by SEQ ID NOS: 16, 17, and 18. In another more preferred embodiment, the humanized antibodies of the invention comprise at least one heavy chain and at least one light chain, wherein said heavy chain comprises three sequential CDRs having amino acid sequences consisting of SEQ ID NOS: 61, 62, and 63, and wherein said light chain comprises three sequential CDRs having amino acid sequences consisting of SEQ ID NOS: 64, 65, and 66. In another more preferred embodiment, the humanized antibodies of the invention comprise at least one heavy chain and at least one light chain, wherein said heavy chain comprises three sequential CDRs having amino acid sequences consisting of SEQ ID NOS: 67, 68, and 69, and wherein said light chain comprises three sequential CDRs having amino acid sequences consisting of SEQ ID NOS: 70, 71, and 72.

In one embodiment, this invention provides humanized antibodies or fragments thereof which comprise a $V_H$ having an amino acid sequence chosen from the group consisting of SEQ ID NOS: 32, 34, 36, 37, 38, 40, 42, 43, and 45. In a preferred embodiment, a humanized 37.1D7 antibody is provided which comprises a $V_H$ having an amino acid sequence chosen from the group consisting of SEQ ID NOS: 32, 34, and 36. In another preferred embodiment, a humanized 37.1F5 antibody is provided which comprises a $V_H$ having an amino acid sequence chosen from the group consisting of SEQ ID NOS: 37 and 38. In another preferred embodiment, a humanized 53.2H11 antibody is provided which comprises a $V_H$ having an amino acid sequence chosen from the group consisting of SEQ ID NOS: 40, 42, 43, and 45.

In another embodiment, this invention provides humanized antibodies or fragments thereof which comprise a $V_L$ having an amino acid sequence chosen from the group consisting of SEQ ID NOS: 47, 48, 49, 50, and 52. In a preferred embodiment, a humanized 37.1D7 antibody is provided which comprises a $V_L$ having an amino acid sequence consisting of SEQ ID NO 47. In another preferred embodiment, a humanized 37.1F5 antibody is provided which comprises a $V_L$ having an amino acid sequence chosen from the group consisting of SEQ ID NOS: 48, 49, and 50. In another preferred embodiment, a humanized 53.2H11 antibody is provided which comprises a $V_L$ having an amino acid sequence consisting of SEQ ID NO 52.

The humanized 37.3D7 antibodies and epitope-binding fragments thereof of the present invention can also include substitution in light and/or heavy chain amino acid residues at one or more positions defined by the grey residues in Table 1A and 1B which represent the murine surface framework residues that have been changed from the original murine residue to the corresponding framework surface residue in the human antibody, 28E4. The starred (*) residues in Table 1B correspond to the murine back mutations in the humanized 37.3D7 heavy chain variants (SEQ ID NO: 34 and SEQ ID NO:36). The residues for back mutations are proximal to CDR's and were chosen as described in U.S. Pat. No. 5,639,641 or in analogy to the selection of residues that had in previous humanization efforts resulted in a decrease in antigen binding affinity (Roguska et al., 1996, *Protein Eng.;* 9(10): 895-904; U.S. patent application publications 2003/0235582 and 2005/0118183).

Likewise, the humanized 37.1F5; 53.2H11; EphA2-N1; and EphA2-N2 antibodies and epitope-binding fragments thereof of the present invention can also include substitution in light and/or heavy chain amino acid residues.

Polynucleotides, Vectors, and Host Cells

Nucleic acids encoding anti-EphA2 antibodies of the invention are provided. In one embodiment, the nucleic acid molecule encodes a heavy and/or a light chain of an anti-EphA2 immunoglobulin. In a preferred embodiment, a single nucleic acid encodes a heavy chain of an anti-EphA2 immunoglobulin and another nucleic acid molecule encodes the light chain of an anti-EphA2 immunoglobulin.

In another aspect of this invention, there are provided polynucleotides encoding polypeptides having an amino acid sequence selected from the group of SEQ ID NOS: 1, 2, 3, 4, 5, 6, 7, 8, 9, 10, 11, 12, 13, 14, 15, 16, 17, 18, 20, 22, 24, 26, 28, 30, 32, 34, 36, 37, 38, 40, 42, 43, 45, 47, 48, 49, 50, 52, 61, 62, 63, 64, 65, 66, 67, 68, 69, 70, 71, 72, 74, 76, 78 and 80. In a preferred embodiment, the polynucleotide of the invention is selected from the group consisting of SEQ ID NOs: 19, 21, 23, 25, 27, 29, 31, 33, 35, 39, 41, 44, 46, 51, 73, 75, 77, and 79. The invention is not limited to said polynucleotides per se but also includes all polynucleotides displaying at least 80% identity with said polynucleotides.

The invention provides vectors comprising the polynucleotides of the invention. In one embodiment, the vector contains a polynucleotide encoding a heavy chain of an anti-EphA2 immunoglobulin. In another embodiment, said polynucleotide encodes the light chain of an anti-EphA2 immunoglobulin. The invention also provides vectors comprising polynucleotide molecules encoding fusion proteins, modified antibodies, antibody fragments, and probes thereof.

In order to express the heavy and/or light chain of the anti-EphA2 antibodies of the invention, the polynucleotides encoding said heavy and/or light chains are inserted into expression vectors such that the genes are operatively linked to transcriptional and translational sequences. Expression vectors include plasmids, YACs, cosmids, retrovirus, EBV-derived episomes, and all the other vectors that the skilled man will know to be convenient for ensuring the expression of said heavy and/or light chains. The skilled man will realize that the polynucleotides encoding the heavy and the light chains can be cloned into different vectors or in the same vector. In a preferred embodiment, said polynucleotides are cloned in the same vector.

Polynucleotides of the invention and vectors comprising these molecules can be used for the transformation of a suitable mammalian host cell, or any other type of host cell known to the skilled person. Transformation can be by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

Antibody Fragments

The antibodies of the present invention include both the full length antibodies discussed above, as well as epitope-binding fragments. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')$_2$, Fd, single-chain Fvs (scFv), single-chain antibodies, disulfide-linked Fvs (dsFv) and fragments comprising either a $V_L$ or $V_H$ region. Epitope-binding fragments, including single-chain antibodies, may comprise the variable region(s) alone or in combination with the entirety or a portion of the following: hinge region, $C_H1$, $C_H2$, and $C_H3$ domains.

Such fragments may contain one or both Fab fragments or the F(ab')$_2$ fragment. Preferably, the antibody fragments contain all six CDRs of the whole antibody, although fragments containing fewer than all of such regions, such as three, four or five CDRs, are also functional. Further, the fragments may be or may combine members of any one of the following immunoglobulin classes: IgG, IgM, IgA, IgD, or IgE, and the subclasses thereof.

Fab and F(ab')$_2$ fragments may be produced by proteolytic cleavage, using enzymes such as papain (Fab fragments) or pepsin (F(ab')$_2$ fragments).

The "single-chain FVs" ("scFvs") fragments are epitope-binding fragments that contain at least one fragment of an antibody heavy chain variable region ($V_H$) linked to at least one fragment of an antibody light chain variable region ($V_L$). The linker may be a short, flexible peptide selected to ensure that the proper three-dimensional folding of the ($V_L$) and ($V_H$) regions occurs once they are linked so as to maintain the target molecule binding-specificity of the whole antibody from which the single-chain antibody fragment is derived. The carboxyl terminus of the ($V_L$) or ($V_H$) sequence may be covalently linked by a linker to the amino acid terminus of a complementary ($V_L$) or ($V_H$) sequence.

Single-chain antibody fragments of the present invention contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, *J. Immunol. Methods*, 182: 41-50; Ames et al., 1995, *J. Immunol. Methods*, 184: 177-186; Kettleborough et al., 1994, *Eur. J. Immunol.*, 24:952-958; Persic et al., 1997, *Gene* 187: 9-18; Burton et al., 1994, *Advances in Immunology*, 57: 191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')$_2$ fragments can also be employed using methods known in the art such as those disclosed in PCT publication WO 92/22324; Mullinax et al., 1992, *BioTechniques*, 12(6): 864-869; Sawai et al., 1995, *AJR*1, 34: 26-34; and Better et al., 1988, *Science*, 240: 1041-1043; said references incorporated by reference in their entireties. Examples of techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. U.S.A.*, 90: 7995-7999; Skerra et al., 1988, *Science*, 240: 1038-1040.

Functional Equivalents

Also included within the scope of the invention are functional equivalents of the anti-EphA antibody and the humanized anti-EphA2 receptor antibody. The term "functional equivalents" includes antibodies with homologous sequences, chimeric antibodies, artificial antibodies and modified antibodies, for example, wherein each functional equivalent is defined by its ability to bind to EphA2 receptor. The skilled artisan will understand that there is an overlap in the group of molecules termed "antibody fragments" and the group termed "functional equivalents." Methods of producing functional equivalents are known to the person skilled in the art and are disclosed, for example, in PCT Application WO 93/21319, European Patent No. EP 0239400; PCT Application WO 89/09622; European Patent No. EP 0338745; and European Patent Application EP 0332424, which are incorporated in their respective entireties by reference.

Antibodies with homologous sequences are those antibodies with amino acid sequences that have sequence homology with amino acid sequence of an anti-EphA antibody and a humanized anti-EphA antibody of the present invention. Preferably homology is with the amino acid sequence of the variable regions of the anti-EphA antibody and humanized anti-EphA antibody of the present invention. "Sequence homology" as applied to an amino acid sequence herein is defined as a sequence with at least about 90%, 91%, 92%, 93%, or 94% sequence homology, and more preferably at least about 95%, 96%, 97%, 98%, or 99% sequence homology to another amino acid sequence, as determined, for example, by the FASTA search method in accordance with Pearson and Lipman, 1988, *Proc. Natl. Acad. Sci. U.S.A.*, 85: 2444-2448.

A chimeric antibody is one in which different portions of an antibody are derived from different animal species. For example, an antibody having a variable region derived from a murine monoclonal antibody paired with a human immunoglobulin constant region. Methods for producing chimeric antibodies are known in the art. See, e.g., Morrison, 1985, *Science*, 229: 1202; Oi et al., 1986, *Bio Techniques*, 4: 214; Gillies et al., 1989, *J. Immunol. Methods*, 125: 191-202; U.S. Pat. Nos. 5,807,715; 4,816,567; and 4,816,397, which are incorporated herein by reference in their entireties.

Humanized forms of chimeric antibodies are made by substituting the complementarity determining regions of, for example, a mouse antibody, into a human framework domain, e.g., see PCT Pub. No. WO92/22653. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Artificial antibodies include scFv fragments, diabodies, triabodies, tetrabodies and mru (see reviews by Winter, G. and Milstein, C., 1991, Nature, 349: 293-299; Hudson, P. J., 1999, *Current Opinion in Immunology*, 11: 548-557), each of which has antigen-binding ability. In the single chain Fv fragment (scFv), the $V_H$ and $V_L$ domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art.

The antibody fragments and functional equivalents of the present invention encompass those molecules with a detectable degree of binding to EphA, when compared to the 37.3D7, 37.1F5, 53.2H11, EphA2-N1 or EphA2-N2 antibody. A detectable degree of binding includes all values in the range of at least 10-100%, preferably at least 50%, 60% or 70%, more preferably at least 75%, 80%, 85%, 90%, 95% or 99% the binding ability of the murine 37.3D7, 37.1F5, 53.2H11, EphA2-N1 or EphA2-N2 antibody to EphA.

Improved Antibodies

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Thus, also included in the scope of the present invention are improved versions of both the murine and humanized antibodies, which also specifically recognize and bind EphA, preferably with increased affinity.

Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254: 392-403; Rader, C. et al., 1998, *Proc. Natl. Acad. Sci. U.S.A.*, 95: 8910-8915; Vaughan, T. J. et al., 1998, *Nature Biotechnology*, 16: 535-539).

In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16: 535-539; Adey, N. B. et al., 1996, Chapter 16, pp. 277-291, in "*Phage Display of Peptides and Proteins*", Eds. Kay, B. K. et al., Academic Press). These methods of changing the sequence of the primary antibody have resulted in improved affinities of the secondary antibodies (Gram, H. et al., 1992, *Proc. Natl. Acad. Sci. U.S.A.*, 89: 3576-3580; Boder, E. T. et al., 2000, *Proc. Natl. Acad. Sci. U.S.A.*, 97: 10701-10705; Davies, J. and Riechmann, L., 1996, *Immunotechnolgy*, 2: 169-179; Thompson, J. et al., 1996, *J. Mol. Biol.*, 256: 77-88; Short, M. K. et al., 2002, *J. Biol. Chem.*, 277: 16365-16370; Furukawa, K. et al., 2001, *J. Biol. Chem.*, 276: 27622-27628).

By a similar directed strategy of changing one or more amino acid residues of the antibody, the antibody sequences described in this invention can be used to develop anti-EphA antibodies with improved functions, including improved affinity for EphA.

Preferred amino acid substitutions are those which: (1) reduce susceptibility to proteolysis, (2) reduce susceptibility to oxidation, (3) alter binding affinity for forming protein complexes, and (4) confer or modify other physico-chemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al., 1991, *Nature*, 354: 105, which are each incorporated herein by reference.

Improved antibodies also include those antibodies having improved characteristics that are prepared by the standard techniques of animal immunization, hybridoma formation and selection for antibodies with specific characteristics.

The present invention also includes cytotoxic conjugates. These cytotoxic conjugates comprise two primary components, a cell-binding agent and a cytotoxic agent.

As used herein, the term "cell binding agent" refers to an agent that specifically recognizes and binds the EphA receptors on the cell surface. In one embodiment, the cell binding agent specifically recognizes the EphA receptor such that it allows the conjugates to act in a targeted fashion with little side-effects resulting from non-specific binding.

In another embodiment, the cell binding agent of the present invention also specifically recognizes the EphA receptor so that the conjugates will be in contact with the target cell for a sufficient period of time to allow the cytotoxic drug portion of the conjugate to act on the cell, and/or to allow the conjugates sufficient time in which to be internalized by the cell.

In a preferred embodiment, the cytotoxic conjugates comprise an anti-EphA antibody as the cell binding agent, more preferably the murine 37.3D7, 37.1F5, 53.2H11, EphA2-N1 or EphA2-N2 anti-EphA monoclonal antibody. In a more preferred embodiment, the cytotoxic conjugate comprises a humanized 37.3D7, 37.1F5, 53.2H11, EphA2-N1 or EphA2-N2 antibody or an epitope-binding fragment thereof. The 37.3D7, 37.1F5, 53.2H11, EphA2-N1 or EphA2-N2 antibody is able to specifically recognize an EphA receptor, such as EphA2, and directs the cytotoxic agent to an abnormal cell or a tissue, such as cancer cells, in a targeted fashion.

The second component of the cytotoxic conjugates of the present invention is a cytotoxic agent. The term "cytotoxic agent" as used herein refers to a substance that reduces or blocks the function, or growth, of cells and/or causes destruction of cells.

In preferred embodiments, the cytotoxic agent is a taxoid, a maytansinoid such as DM1 or DM4, a small drug, a tomaymycin derivative, a leptomycin derivative, a prodrug, CC-1065 or a CC-1065 analog. In preferred embodiments, the cell binding agents of the present invention are covalently attached, directly or via a cleavable or non-cleavable linker, to the cytotoxic agent.

The cell binding agents, cytotoxic agents, and linkers are discussed in more detail below.

Cell Binding Agents

The effectiveness of the compounds of the present invention as therapeutic agents depends on the careful selection of an appropriate cell binding agent. Cell binding agents may be of any kind presently known, or that become known, and includes peptides and non-peptides. The cell binding agent may be any compound that can bind a cell, either in a specific or non-specific manner. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:

polyclonal antibodies;

monoclonal antibodies;

fragments of antibodies such as Fab, Fab', and $F(ab')_2$, Fv (Parham, 1983, *J. Immunol.*, 131:2895-2902; Spring et al., 1974, *J. Immunol.*, 113: 470-478; Nisonoff et al., 1960, *Arch. Biochem. Biophys.*, 89: 230-244).

Preferably, a humanized anti-EphA antibody is used as the cell binding agent of the present invention. More preferably the humanized anti-EphA antibody is selected from humanized or resurfaced 37.3D7, 37.1F5; 53.2H11; EphA2-N1 and EphA2-N2 antibodies.

Cytotoxic Agents

In another embodiment, the humanized antibody or an epitope-binding fragment thereof can be conjugated to a drug, such as a maytansinoid or a tomaymycin derivative, to form a prodrug having specific cytotoxicity towards antigen-expressing cells by targeting the drug to the EphA2 receptor. Cytotoxic conjugates comprising such antibodies and a small, highly toxic drug (e.g., maytansinoids, taxanes, tomaymycin derivatives, a leptomycin derivative, CC-1065, and CC-1065 analogs) can be used as a therapeutic for treatment of tumors, such as breast and ovarian tumors.

The cytotoxic agent used in the cytotoxic conjugate of the present invention may be any compound that results in the death of a cell, or induces cell death, or in some manner decreases cell viability. Preferred cytotoxic agents include, for example, maytansinoids and maytansinoid analogs, a prodrug, tomaymycin derivatives, taxoids, a leptomycin derivative, CC-1065 and CC-1065 analogs, defined below. These cytotoxic agents are conjugated to the antibodies, antibodies fragments, functional equivalents, improved antibodies and their analogs as disclosed herein.

The cytotoxic conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the drug or prodrug.

Maytansinoids

Among the cytotoxic agents that may be used in the present invention to form a cytotoxic conjugate, are maytansinoids and maytansinoid analogs. Examples of suitable maytansinoids include maytansinol and maytansinol analogs. Maytansinoids are drugs that inhibit microtubule formation and that are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:
(1) C-19-dechloro (U.S. Pat. No. 4,256,746) (prepared by LAH reduction of ansamytocin P2);
(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:
(1) C-9-SH (U.S. Pat. No. 4,424,219) (prepared by the reaction of maytansinol with $H_2S$ or $P_2S_5$),
(2) C-14-alkoxymethyl (demethoxy/$CH_2OR$) (U.S. Pat. No. 4,331,598);
(3) C-14-hydroxymethyl or acyloxymethyl ($CH_2OH$ or $CH_2OAc$) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia nudiflora*);
(6) C-18-N-demethyl (U.S. Pat. Nos. 4,362,663 and 4,322,348) (prepared by the demethylation of maytansinol by *Streptomyces*); and
(7) 4,5-deoxy (U.S. Pat. No. 4,371,533) (prepared by the titanium trichloride/LAH reduction of maytansinol).

In a preferred embodiment, the cytotoxic conjugates of the present invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

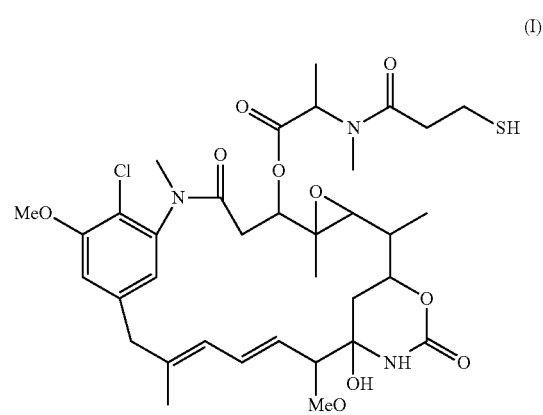 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

(I)

In another preferred embodiment, the cytotoxic conjugates of the present invention utilize the thiol-containing maytansinoid $N^{2'}$-deacetyl-$N^{-2'}$(4-methyl-4-mercapto-1-oxopentyl)-maytansine as the cytotoxic agent. DM4 is represented by the following structural formula (II):

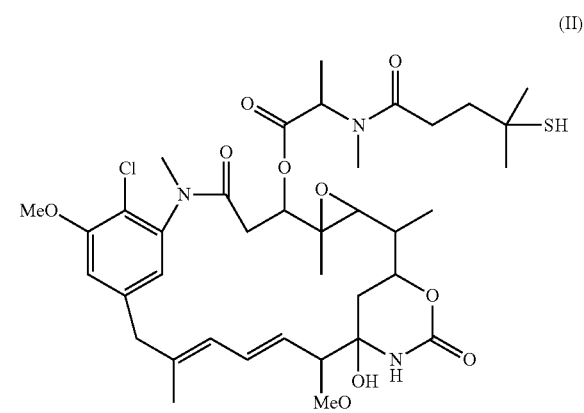 [SMILES: COc1cc2cc(c1Cl)N(C)C(=O)CC(OC(=O)C(C)N(C)C(=O)CCC(C)(C)S)C1(C)OC1C(C)C1CC(O)(NC(=O)O1)C(OC)/C=C/C=C(\C)C2]

(II)

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Such additional maytansines include compounds represented by formula (III):

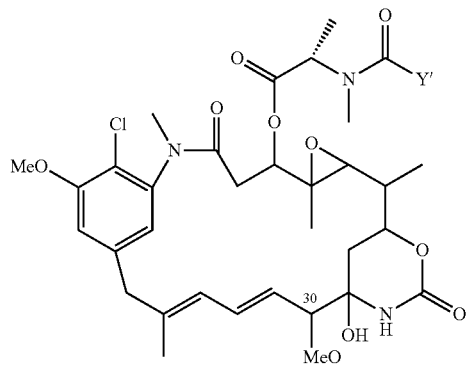

(III)

wherein:

Y' represents
$(CR_7R_8)_l(CR_9=CR_{10})_p(C\equiv C)_qA_r(CR_5R_6)_mD_u$
$(CR_{11}=CR_{12})_r(C\equiv C)_sB_t(CR_3R_4)_nCR_1R_2SZ$,
wherein:

- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- A, B, D are cycloalkyl or cycloalkenyl having 3-10 carbon atoms, simple or substituted aryl or heterocyclic aromatic or heterocycloalkyl radical;
- $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
- l, m, n, o, p, q, r, s, and t are each independently 0 or an integer of from 1 to 5, provided that at least two of l, m, n, o, p, q, r, s and t are not zero at any one time; and
- Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (III) include compounds of formula (III) wherein:

- $R_1$ is methyl, $R_2$ is H and Z is H.
- $R_1$ and $R_2$ are methyl and Z is H.
- $R_1$ is methyl, $R_2$ is H, and Z is —$SCH_3$.
- $R_1$ and $R_2$ are methyl, and Z is —$SCH_3$.

Such additional maytansines also include compounds represented by formula (IV-L), (IV-D), or (IV-D,L):

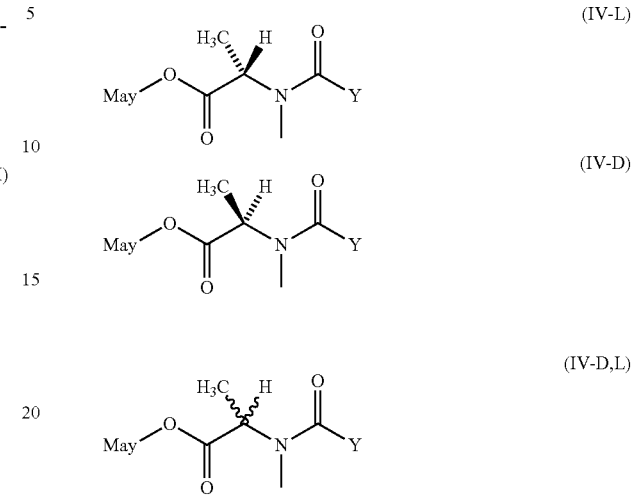

wherein:

Y represents $(CR_7R_8)_l(CR_5R_6)_m(CR_3R_4)_nCR_1R_2SZ$, wherein:

- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;
- l, m and n are each independently an integer of from 1 to 5, and in addition n can be 0;
- Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical; and
- May represents a maytansinoid which bears the side chain at C-3, C-14 hydroxymethyl, C-15 hydroxy or C-20 desmethyl.

Preferred embodiments of formulas (IV-L), (IV-D) and (IV-D,L) include compounds of formulas (IV-L), (IV-D) and (IV-D,L) wherein:

- $R_1$ is methyl, $R_2$ is H, $R_3$, $R_6$, $R_7$, and $R_8$ are each H, l and m are each 1, n is 0, and Z is H.
- $R_1$ and $R_2$ are methyl, $R_5$, $R_6$, $R_7$, $R_8$ are each H, l and m are 1, n is 0, and Z is H.
- $R_1$ is methyl, $R_2$ is H, $R_5$, $R_6$, $R_7$, and $R_8$ are each H, l and m are each 1, n is 0, and Z is —$SCH_3$.
- $R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Such additional maytansines also include compounds represented by formula (V):

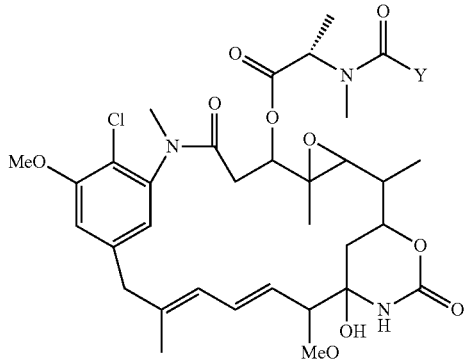

(V)

wherein:
Y represents $(CR_7R_8)_l(CR_5R_6)_m(CR_3R_4)_nCR_1R_2SZ$,
wherein:
- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;
- l, m and n are each independently an integer of from 1 to 5, and in addition n can be 0; and
- Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein:
- $R_1$ is methyl, $R_2$ is H, R5, R6, R7, and R8 are each H; l and m are each 1; n is 0; and Z is H.
- $R_1$ and $R_2$ are methyl; $R_5$, $R_6$, $R_7$, $R_8$ are each H, l and m are 1; n is 0; and Z is H.
- $R_1$ is methyl, $R_2$ is H, $R_8$, $R_6$, $R_7$, and $R_8$ are each H, l and m are each 1, n is 0, and Z is —$SCH_3$.
- $R_1$ and $R_2$ are methyl, $R_5$, $R_6$, $R_7$, $R_8$ are each H, l and m are 1, n is 0, and Z is —$SCH_3$.

Such additional maytansines further include compounds represented by formula (VI-L), (VI-D), or (VI-D,L):

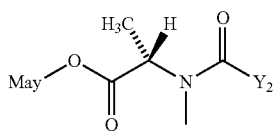

(VI-L)

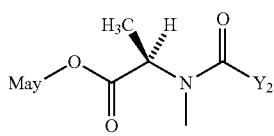

(VI-D)

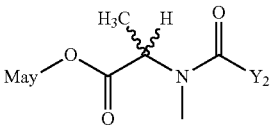

(VI-D,L)

wherein:
$Y_2$ represents $(CR_7R_8)_l(CR_5R_6)_m(CR_3R_4)_nCR_1R_2SZ_2$,
wherein:
- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
- l, m and n are each independently an integer of from 1 to 5, and in addition n can be 0;
- $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical; and
- May is a maytansinoid.

Such additional maytansines also include compounds represented by formula (VII):

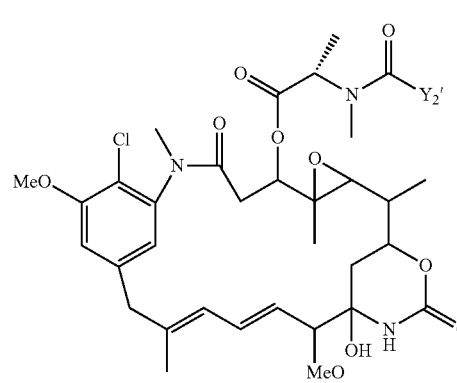

(VII)

wherein:
$Y_2'$ represents
$(CR_7R_8)_l(CR_9=CR_{10})_p(C\equiv C)_qA_r(CR_5R_6)_mD_u$
$(CR_{11}=CR_{12})_r(C\equiv C)_sB_t(CR_3R_4)_nCR_1R_2SZ_2$,
wherein:
- $R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H;
- A, B, and D each independently is cycloalkyl or cycloalkenyl having 3 to 10 carbon atoms, simple or substituted aryl, or heterocyclic aromatic or heterocycloalkyl radical;
- $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m, n, o, p, q, r, s, and t are each independently 0 or an integer of from 1 to 5, provided that at least two of l, m, n, o, p, q, r, s and t are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocycloalkyl radical.

Preferred embodiments of formula (VII) include compounds of formula (VII) wherein: $R_1$ is methyl, $R_2$ is H.

The above-mentioned maytansinoids can be conjugated to anti-EphA antibody 37.3D7, 37.1F5, 53.2H11, EphA2-N1 or EphA2-N2 or a homologue or fragment thereof, wherein the antibody is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition one of the substituents can be H, and wherein the acyl group has a linear chain length of at least three carbon atoms between the carbonyl functionality and the sulfur atom.

A preferred conjugate of the present invention is the one that comprises the anti-EphA antibody 37.3D7, 37.1F5, 53.2H11, EphA2-N1 or EphA2-N2 or a homologue or fragment thereof, conjugated to a maytansinoid of formula (VIII):

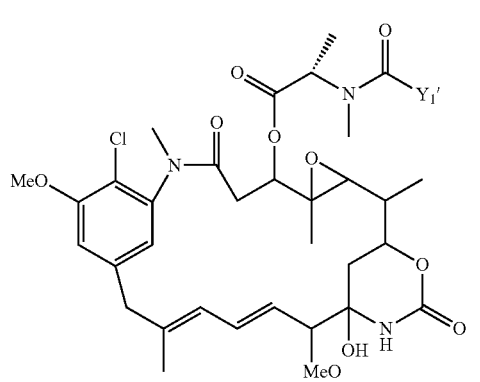

(VIII)

wherein:
$Y_1'$ represents
$(CR_7R_8)_l(CR_9=CR_{10})_p(C\equiv C)_qA_r(CR_5R_6)_mD_u$
$(CR_{11}=CR_{12})_r(C\equiv C)_sB_t(CR_3R_4)_nCR_1R_2S—$,
wherein:
  A, B, and D, each independently is cycloalkyl or cycloalkenyl having 3-10 carbon atoms, simple or substituted aryl, or heterocyclic aromatic or heterocycloalkyl radical;
  $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical; and l, m, n, o, p, q, r, s, and t are each independently 0 or an integer of from 1 to 5, provided that at least two of l, m, n, o, p, q, r, s and t are non-not zero at any one time.

Preferably, $R_1$ is methyl, $R_2$ is H, or $R_1$ and $R_2$ are methyl.

An even more preferred conjugate of the present invention is the one that comprises the anti-EphA antibody 37.3D7, 37.1F5, 53.2H11, EphA2-N1 or EphA2-N2 or a homologue or fragment thereof, conjugated to a maytansinoid of formula (IX-L), (IX-D), or (IX-D,L):

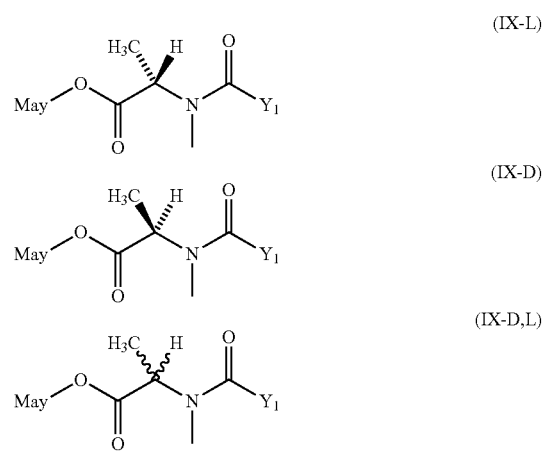

wherein:
$Y_1$ represents $(CR_7R_8)_l(CR_5R_6)_m(CR_3R_4)_nCR_1R_2S—$,
wherein:
  $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, heterocyclic aromatic or heterocycloalkyl radical, and in addition $R_2$ can be H;
  $R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
  l, m and n are each independently an integer of from 1 to 5, and in addition n can be 0; and
  May represents a maytansinol which bears the side chain at C-3, C-14 hydroxymethyl, C-15 hydroxy or C-20 desmethyl.

Preferred embodiments of formulas (IX-L), (IX-D) and (IX-D,L) include compounds of formulas (IX-L), (IX-D) and (IX-D,L) wherein:
  $R_1$ is methyl, $R_2$ is H, or $R_1$ and $R_2$ are methyl,
  $R_1$ is methyl, $R_2$ is H, $R_5$, $R_6$, $R_7$ and $R_8$ are each H; l and m are each 1; n is 0,
  $R_1$ and $R_2$ are methyl; $R_5$, $R_6$, $R_7$ and $R_8$ are each H; l and m are 1; n is 0.

Preferably the cytotoxic agent is represented by formula (IX-L).

A further preferred conjugate of the present invention is the one that comprises the anti-EphA antibody 37.3D7, 37.1F5, 53.2H11, EphA2-N1 or EphA2-N2 or a homologue or fragment thereof, conjugated to a maytansinoid of formula (X):

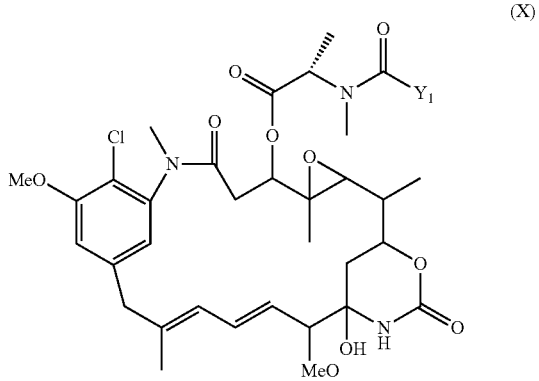

(X)

wherein the substituents are as defined for formula (IX) above.

Especially preferred are any of the above-described compounds, wherein $R_1$ is H, $R_2$ is methyl, $R_5$, $R_6$, $R_7$ and $R_8$ are each H, l and m are each 1, and n is 0.

Further especially preferred are any of the above-described compounds, wherein $R_1$ and $R_2$ are methyl, $R_5$, $R_6$, $R_7$, $R_8$ are each H, l and m are 1, and n is 0

Further, the L-aminoacyl stereoisomer is preferred.

Each of the maytansinoids taught in pending U.S. patent application Ser. No. 10/849,136, filed May 20, 2004, may also be used in the cytotoxic conjugate of the present invention. The entire disclosure of U.S. patent application Ser. No. 10/849,136 is incorporated herein by reference.

Disulfide-Containing Linking Groups

In order to link the maytansinoid to a cell binding agent, such as the 37.3D7, 37.1F5, 53.2H11, EphA2-N1 or EphA2-N2 antibody, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

The linking moiety also comprises a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

While the synthesis of esters of maytansinol having a linking moiety is described in terms of disulfide bond-containing linking moieties, one of skill in the art will understand that linking moieties with other chemical bonds (as described above) can also be used with the present invention, as can other maytansinoids. Specific examples of other chemical bonds include acid labile bonds, photolabile bonds, peptidase labile bonds and esterase labile bonds. The disclosure of U.S. Pat. No. 5,208,020, incorporated herein, teaches the production of maytansinoids bearing such bonds.

The synthesis of maytansinoids and maytansinoid derivatives having a disulfide moiety that bears a reactive group is described in U.S. Pat. Nos. 6,441,163 and 6,333,410, and U.S. application Ser. No. 10/161,651, each of which is herein incorporated by reference.

The reactive group-containing maytansinoids, such as DM1, are reacted with an antibody, such as the 37.3D7, 37.1F5, 53.2H11, EphA2-N1 or EphA2-N2 antibody, to produce cytotoxic conjugates. These conjugates may be purified by HPLC or by gel-filtration.

Several excellent schemes for producing such antibody-maytansinoid conjugates are provided in U.S. Pat. No. 6,333,410, and U.S. application Ser. Nos. 09/867,598, 10/161,651 and 10/024,290, each of which is incorporated herein in its entirety.

In general, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel-filtration.

The number of maytansinoid molecules bound per antibody molecule can be determined by measuring spectrophotometrically the ratio of the absorbance at 252 nm and 280 nm. An average of 1-10 maytansinoid molecules/antibody molecule is preferred.

Conjugates of antibodies with maytansinoid drugs can be evaluated for their ability to suppress proliferation of various unwanted cell lines in vitro. For example, cell lines such as the human epidermoid carcinoma line A-431, the human small cell lung cancer cell line SW2, the human breast tumor line SKBR3 and the Burkitt's lymphoma cell line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

PEG-Containing Linking Groups

Maytansinoids may also be linked to cell binding agents using PEG linking groups, as set forth in U.S. application Ser. No. 10/024,290. These PEG linking groups are soluble both in water and in non-aqueous solvents, and can be used to join one or more cytotoxic agents to a cell binding agent. Exemplary PEG linking groups include hetero-bifunctional PEG linkers that bind to cytotoxic agents and cell binding agents at opposite ends of the linkers through a functional sulfhydryl or disulfide group at one end, and an active ester at the other end.

As a general example of the synthesis of a cytotoxic conjugate using a PEG linking group, reference is again made to U.S. application Ser. No. 10/024,290 for specific details. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, such as the 37.3D7, 37.1F5, 53.2H11, EphA2-N1 or EphA2-N2 antibody, to yield a cytotoxic conjugate comprising one or more cytotoxic agents covalently bonded to a cell binding agent through a PEG linking group.

Taxanes

The cytotoxic agent used in the cytotoxic conjugates according to the present invention may also be a taxane or derivative thereof.

Taxanes are a family of compounds that includes paclitaxel (taxol), a cytotoxic natural product, and docetaxel (Taxotere), a semi-synthetic derivative, two compounds that are widely used in the treatment of cancer. Taxanes are mitotic-spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell binding agents.

A preferred taxane for use in the preparation of cytotoxic conjugates is the taxane of formula (XI):

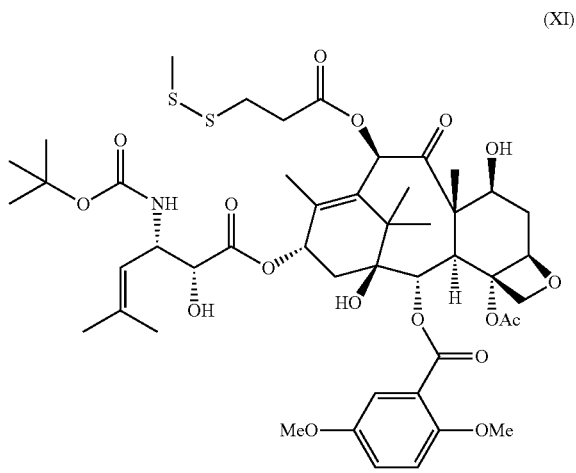 [SMILES: COc1ccc(OC)c(C(=O)O[C@H]2[C@@H]3[C@]4(OC(C)=O)CO[C@@H]4C[C@H](O)[C@@]3(C)C(=O)[C@H](OC(=O)CCSSC)C3=C(C)[C@@H](OC(=O)[C@H](O)[C@H](C=C(C)C)NC(=O)OC(C)(C)C)C[C@]2(O)C3(C)C)c1]

(XI)

Methods for synthesizing taxanes that may be used in the cytotoxic conjugates of the present invention, along with methods for conjugating the taxanes to a cell binding agent, such as the 37.3D7, 37.1F5, 53.2H11, EphA2-N1 or EphA2-N2 antibody, are described in detail in U.S. Pat. Nos. 5,416,064, 5,475,092, 6,340,701, 6,372,738 and 6,436,931, and in U.S. application Ser. Nos. 10/024,290, 10/144,042, 10/207,814, 10/210,112 and 10/369,563.

Tomaymycin Derivatives

The cytotoxic according to the present invention may also a tomaymycin derivative. Tomaymycin derivatives are pyrrolo[1,4]benzodiazepines (PBDs), a known class of compounds exerting their biological properties by covalently binding to the N2 of guanine in the minor groove of DNA. PBDs include a number of minor groove binders such as anthramycin, neothramycin and DC-81.

Novel tomaymycin derivatives that retain high cytotoxicity and that can be effectively linked to cell binding agents are described in the International Application No. PCT/IB2007/000142, whose content is herein incorporated by reference. The cell binding agent-tomaymycin derivative complexes permit the full measure of the cytotoxic action of the tomaymycin derivatives to be applied in a targeted fashion against unwanted cells only, therefore avoiding side effects due to damage to non-targeted healthy cells.

The cytotoxic agent according to the present invention comprises one or more tomaymycin derivatives, linked to a cell binding agent, such as the 37.3D7, 37.1F5, 53.2H11, EphA2-N1 or EphA2-N2 antibody, via a linking group. The linking group is part of a chemical moiety that is covalently bound to a tomaymycin derivative through conventional methods. In a preferred embodiment, the chemical moiety can be covalently bound to the tomaymycin derivative via a disulfide bond.

The tomaymycin derivatives useful in the present invention have the formula (XII) shown below:

wherein
- - - represents an optional single bond;
═ represents either a single bond or a double bond;
provided that when ═ represents a single bond, U and U', the same or different, independently represent H, and W and W', the same or different, are independently selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO3-, a sulfonamide such as —NRSOOR, an amine such as —NRR', optionally cyclic amine such that N10 and C11 are a part of the cycle, a hydroxylamine derivative such as —NROR', an amide such as —NRCOR, an azido such as —N3, a cyano, a halo, a trialkyl or triarylphosphonium, an aminoacid-derived group; Preferably W and W' are the same or different and are OH, Ome, Oet, NHCONH$_2$, SMe;

and when ═ represents a double bond, U and U' are absent and W and W' represent H;

R1, R2, R1', R2' are the same or different and independently chosen from Halide or Alkyl optionally substituted by one or more Hal, CN, NRR', CF$_3$, OR, Aryl, Het, S(O)$_q$R, or R1 and R2 and R1' and R2' form together a double bond containing group ═B and ═B' respectively.

Preferably, R1 and R2 and R1' and R2' form together a double bond containing group ═B and ═B' respectively.

B and B' are the same or different and independently chosen from Alkenyl being optionally substituted by one or more Hal, CN, NRR', CF$_3$, OR, Aryl, Het, S(O)$_q$R or B and B' represent an oxygen atom.

Preferably, B═B'.

More preferably, B═B'══CH$_2$ or ═CH—CH$_3$,

X, X' are the same or different and independently chosen from one or more —O—, —NR—, —(C═O)—, —S(O)$_q$—.

Preferably, X═X'.

More preferably, X═X'═O.

A, A' are the same or different and independently chosen from Alkyl or Alkenyl optionally containing an oxygen, a nitrogen or a sulfur atom, each being optionally substituted by one or more Hal, CN, NRR', CF$_3$, OR, S(O)$_q$R, Aryl, Het, Alkyl, Alkenyl.

Preferably, A═A'.

More preferably, A═A'═linear unsubstituted alkyl.

Y, Y' are the same or different and independently chosen from H, OR;

Preferably, Y═Y'.

More preferably, Y═Y'═OAlkyl, more preferably OMethyl.

T is —NR—, —O—, —S(O)$_q$—, or a 4 to 10-membered aryl, cycloalkyl, heterocyclic or heteroaryl, each being

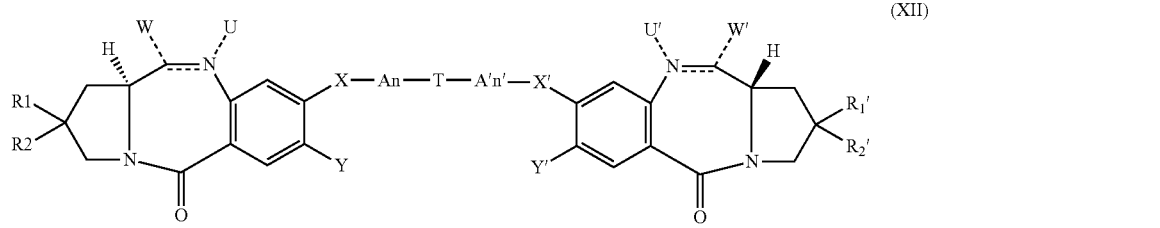

(XII)

optionally substituted by one or more Hal, CN, NRR', CF₃, R, OR, S(O)$_q$R, and/or linker(s), or a branched Alkyl, optionally substituted by one or more Hal, CN, NRR', CF₃, OR, S(O)$_q$R and/or linker(s), or a linear Alkyl substituted by one or more Hal, CN, NRR', CF₃, OR, S(O)$_q$R and/or linker(s).

Preferably, T is a 4 to 10-membered aryl or heteroaryl, more preferably phenyl or pyridyl, optionally substituted by one or more linker(s).

Said linker comprises a linking group. Suitable linking groups are well known in the art and include thiol, sulfide, disulfide groups, thioether groups, acid labile groups, photolabile groups, peptidase labile groups and esterase labile groups. Preferred are disulfide groups and thioether groups.

When the linking group is a thiol-, sulfide (or so-called thioether —S—) or disulfide (—S—S—)-containing group, the side chain carrying the thiol, the sulfide or disulfide group can be linear or branched, aromatic or heterocyclic. One of ordinary skill in the art can readily identify suitable side chains.

Preferably, said linker is of formula:

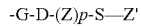
-G-D-(Z)p-S—Z' where
G is a single or double bond, —O—, —S— or —NR—;
D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;
where E and F are the same or different and are independently chosen from linear or branched —(OCH2CH2)iAlkyl (OCH2CH2)j-, -Alkyl(OCH2CH2)i-Alkyl-, —(OCH2CH2)i-, (OCH2CH2)iCycloalkyl(OCH2CH2)j-, —(OCH2CH2)iHeterocyclic(OCH2CH2)j-, (OCH2CH2)iAryl(OCH2CH2)j-, —(OCH2CH2)iHeteroaryl(OCH2CH2)j-, -Alkyl-(OCH2CH2)iAlkyl(OCH2CH2)j-, -Alkyl-(OCH2CH2)i-, -Alkyl-(OCH2CH2)iCycloalkyl(OCH2CH2)j-, -Alkyl (OCH2CH2)iHeterocyclic(OCH2CH2)j-, -Alkyl-(OCH2CH2)iAryl(OCH2CH2)j-, -Alkyl(OCH2CH2)iHeteroaryl(OCH2CH2)j-, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
where i and j, identical or different are integers and independently chosen from 0, 1 to 2000;
Z is linear or branched -Alkyl-;
p is 0 or 1;
Z' represents H, a thiol protecting group such as COR, R20 or SR20, wherein R20 represents H, methyl, Alkyl, optionally substituted Cycloalkyl, aryl, heteroaryl or heterocyclic, provided that when Z' is H, said compound is in equilibrium with the corresponding compound formed by intramolecular cyclisation resulting from addition of the thiol group —SH on the imine bond —NH= of one of the PBD moieties.

n, n', equal or different are 0 or 1.
q is 0, 1 or 2.
R, R' are equal or different and independently chosen from H, Alkyl, Aryl, each being optionally substituted by Hal, CN, NRR', CF3, R, OR, S(O)qR, Aryl, Het;

or their pharmaceutically acceptable salts, hydrates, or hydrated salts, or the polymorphic crystalline structures of these compounds or their optical isomers, racemates, diastereomers or enantiomers.

The compounds of the general formula (XII) having geometrical and stereoisomers are also a part of the invention.

The N-10, C-11 double bond of tomaymycin derivatives of formula (XII) is known to be readily convertible in a reversible manner to corresponding imine adducts in the presence of water, an alcohol, a thiol, a primary or secondary amine, urea and other nucleophiles. This process is reversible and can easily regenerate the corresponding tomaymycin derivatives in the presence of a dehydrating agent, in a non-protic organic solvent, in vacuum or at high temperatures (Z. Tozuka, 1983, *J. Antibiotics*, 36: 276).

Thus, reversible derivatives of tomaymycin derivatives of general formula (XIII) can also be used in the present invention:

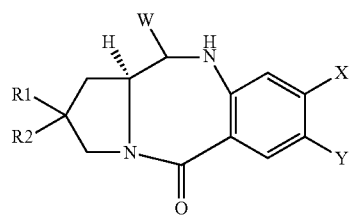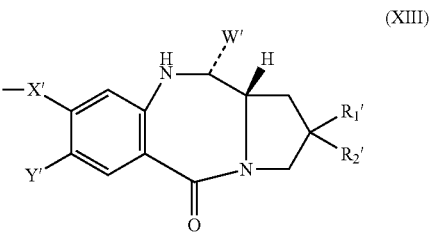

(XIII)

where A, X, Y, n, T, A', X', Y', n', R1, R2, R1', R2' are defined as in formula (XII) and W, W' are the same or different and are selected from the group consisting of OH, an ether such as —OR, an ester (e.g. an acetate), such as —OCOR, —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO3-, a sulfonamide such as —NRSOOR, an amine such as —NRR', optionally cyclic amine such that N10 and C11 are a part of the cycle, a hydroxylamine derivative such as —NROR', an amide such as —NRCOR, —NRCONRR', an azido such as —N3, a cyano, a halo, a trialkyl or triarylphosphonium, an aminoacid-derived group. Preferably, W and W' are the same or different and are OH, Ome, Oet, NHCONH2, SMe.

Compounds of formula (XIII) may thus be considered as solvates, including water when the solvent is water; these solvates can be particularly useful.

In a preferred embodiment, the tomaymycin derivatives of the invention are selected from the group consisting in:
8,8'-[1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]
8,8'-[5-methoxy-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]
8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis-(methyleneoxy)]bis[(S)-2-eth-(E)-ylidene-7-methoxy-1,2,3,11a-tetrahydro-5H-pyrrolo[2,1-c][1,4]benzodiazepin-5-one]

8,8'-[4-(3-aminopropyloxy)-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(N-methyl-3-tert-butoxycarbonylaminopropyl)-1,3-benzenediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyldisulfanyl-pentanoylamino)propyloxy]-1,3-benzenediylbis(methyleneoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methyleneoxy)]-bis[(S)-2-methylene-7-methoxy-1,2,3,11a-tetrahydro-5H-pyrrolo[2,1-c][1,4]benzodiazepin-5-one]

bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[(4-(2-(4-mercapto-4-methyl-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl)-pentanamidopropoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamido-butoxy)-pyridin-2,6-dimethyl)-dioxy]bis[(S)-2-eth-(E)-ylidene-7-dimethoxy-1,2,3,11a-tetrahydro-pyrrolo[2,1-c][1,4]benzodiazepin-5-one]

8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

as well as the corresponding mercapto derivatives, or their pharmaceutically acceptable salts, hydrates, or hydrated salts, or the polymorphic crystalline structures of these compounds or their optical isomers, racemates, diastereomers or enantiomers.

Preferred compounds are those of formula:

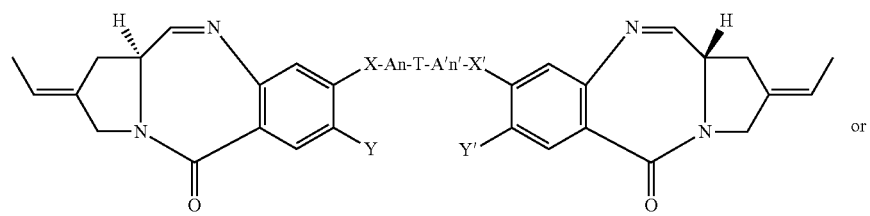

or

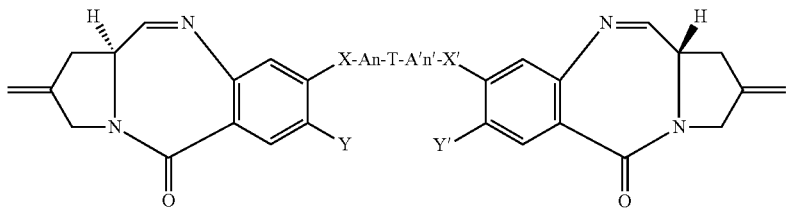

where X, X', A, A', Y, Y', T, n, n' are defined as above.

The compounds of formula (XII) may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

Methods for synthesizing the tomaymycin derivatives which may be used in the invention are described in the International Application No. PCT/IB2007/000142. Compounds of the present invention may be prepared by a variety of synthetic routes. The reagents and starting materials are commercially available, or readily synthesized by well-known techniques by one of ordinary skill in the arts (see, for example, WO 00/12508, WO 00/12507, WO 2005/040170, WO 2005/085260, FR1516743, M. Mori et al., 1986, *Tetrahedron*, 42: 3793-3806).

The conjugate molecules of the invention may be formed using any techniques. The tomaymycin derivatives of the invention may be linked to an antibody or other cell binding agent via an acid labile linker, or by a photolabile linker. The derivatives can be condensed with a peptide having a suitable sequence and subsequently linked to a cell binding agent to produce a peptidase labile linker. The conjugates can be prepared to contain a primary hydroxyl group, which can be succinylated and linked to a cell binding agent to produce a conjugate that can be cleaved by intracellular esterases to liberate free derivative. Preferably, the derivatives are synthesized to contain a free or protected thiol group, and then one or more disulfide or thiol-containing derivatives are each covalently linked to the cell binding agent via a disulfide bond or a thioether link.

Numerous methods of conjugation are taught in U.S. Pat. No. 5,416,064 and U.S. Pat. No. 5,475,092. The tomaymycin derivatives can be modified to yield a free amino group and then linked to an antibody or other cell binding agent via an acid labile linker or a photolabile linker. The tomaymycin derivatives with a free amino or carboxyl group can be condensed with a peptide and subsequently linked to a cell binding agent to produce a peptidase labile linker. The tomaymycin derivatives with a free hydroxyl group on the linker can be succinylated and linked to a cell binding agent to produce a conjugate that can be cleaved by intracellular esterases to liberate free drug. Most preferably, the tomaymycin derivatives are treated to create a free or protected thiol group, and then the disulfide- or thiol containing tomaymycin dimers are linked to the cell binding agent via disulfide bonds.

Preferably, monoclonal antibody- or cell binding agent-tomaymycin derivative conjugates are those that are joined via a disulfide bond, as discussed above, that are capable of delivering tomaymycin derivatives. Such cell binding conjugates are prepared by known methods such as by modifying monoclonal antibodies with succinimidyl pyridyl-dithiopropionate (SPDP) (Carlsson et al., 1978, *Biochem. J.*, 173: 723-737). The resulting thiopyridyl group is then displaced by treatment with thiol-containing tomaymycin derivatives to produce disulfide linked conjugates. Alternatively, in the case of the aryldithio-tomaymycin derivatives, the formation of the cell binding conjugate is effected by direct displacement of the aryl-thiol of the tomaymycin derivative by sulfhydryl groups previously introduced into antibody molecules. Conjugates containing 1 to 10 tomaymycin derivative drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing tomaymycin derivative (1.3 molar eq./dithiopyridyl group). The release of thio-nitropyridine from the modified antibody is monitored spectrophotometrically at 325 nm and is complete in about 16 hours. The antibody-tomaymycin derivative conjugate is purified and freed of unreacted drug and other low molecular weight material by gel filtration through a column of Sephadex G-25 or Sephacryl S300. The number of tomaymycin derivative moieties bound per antibody molecule can be determined by measuring the ratio of the absorbance at 230 nm and 275 nm. An average of 1-10 tomaymycin derivative molecules/antibody molecule can be linked via disulfide bonds by this method.

The effect of conjugation on binding affinity towards the antigen-expressing cells can be determined using the methods previously described by Liu et al., 1996, *Proc. Natl. Acad. Sci. U.S.A.*, 93: 8618-8623. Cytotoxicity of the tomaymycin derivatives and their antibody conjugates to cell lines can be measured by back-extrapolation of cell proliferation curves as described in Goldmacher et al., 1985, *J. Immunol.*, 135: 3648-3651. Cytotoxicity of these compounds to adherent cell lines can be determined by clonogenic assays as described in Goldmacher et al., 1986, *J. Cell Biol.*, 102: 1312-1319.

Leptomycin Derivatives

The cytotoxic according to the present invention may also a leptomycin derivative. According to the present invention, "leptomycin derivatives" refer to members of the leptomycin family as defined in Kalesse et al. (2002, *Synthesis* 8: 981-1003), and includes: leptomycins, such as leptomycin A and leptomycin B, callystatins, ratjadones such as ratjadone A and ratjadone B, anguinomycins such as anguinomycin A, B, C, D, kasusamycins, leptolstatin, leptofuranins, such as leptofuranin A, B, C, D. Derivatives of leptomycin A and B are preferred.

More specifically, the derivatives of the invention are of formula (I):

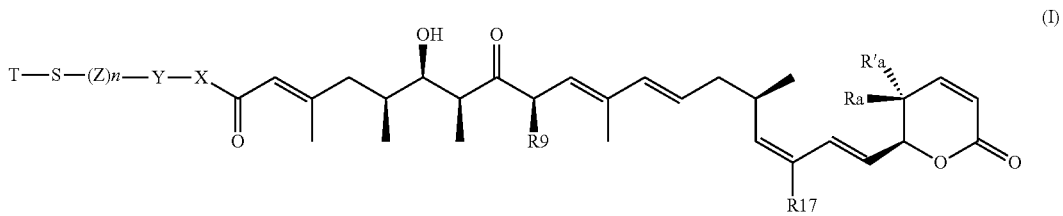

wherein
Ra and Ra' are H or -Alk; preferably Ra is -Alk, preferably methyl and Ra' is H;

R17 is alkyl optionally substituted by OR, CN, NRR', perfluoroalkyl; preferably, R17 is alkyl, more preferably methyl or ethyl;

R9 is alkyl optionally substituted by OR, CN, NRR', perfluoroalkyl; preferably, R9 is alkyl, more preferably methyl;

X is —O— or —NR—; preferably, X is —NR—;

Y is —U—, —NR—U—, —O—U—, —NR—CO—U—, —U—NR—CO—, —U—CO—, —CO—U—;

preferably, when X is —O—, Y is —U—, —NR—U—, —U—NR—CO—;

where U is chosen from linear or branched -Alk-, -Alk($OCH_2CH_2$)$_m$—, —($OCH_2CH_2$)$_m$-Alk-, -Alk($OCH_2CH_2$)$_m$-Alk-, —($OCH_2CH_2$)$_m$—, -Cycloalkyl-, -Heterocyclic-, -Cycloalkyl-Alk-, -Alk-Cycloalkyl-, -Heterocyclic-Alk-, -Alk-Heterocyclic-;

where m is an integer chosen from 1 to 2000;
preferably, U is linear or branched -Alk-,
Z is -Alk-;
n is 0 or 1; preferably n is 0;
T represents H, a thiol protecting group such as Ac, $R_1$, or $SR_1$, wherein $R_1$ represents H, methyl, Alk, Cycloalkyl, optionally substituted aryl or heterocyclic, or T represents

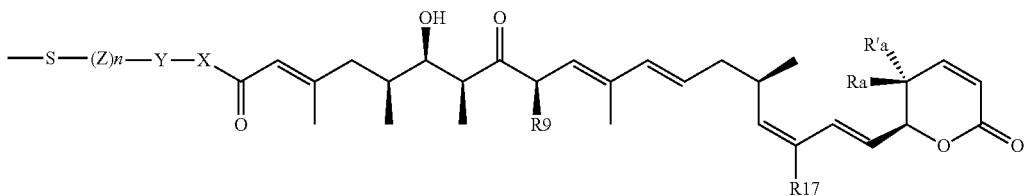

where:
Ra, Ra', R17, R9, X, Y, Z, n are defined as above;
preferably, T is H or $SR_1$, wherein $R_1$ represents Alk, more preferably methyl;

R, R' identical or different are H or alkyl;

Alk represents a linear or branched alkyl; preferably Alk represents (—($CH_{2-q}$, ($CH_3$)$_q$)$_p$— where p represents an integer from 1 to 10; and q represents an integer from 0 to 2; preferably, Alk represents —($CH_2$)— ou —$C(CH_3)_2$—.

or their pharmaceutically acceptable salts, hydrates, or hydrated salts, or the polymorphic crystalline structures of these compounds or their optical isomers, racemates, diastereomers or enantiomers.

Preferred compounds may be chosen from:
(2-Methylsulfanyl-ethyl)-amid of (2E,10E,12E,16Z,18E)-(R)-6-Hydroxy-3,5, 7,9,11,15,17-heptamethyl-19-((2S, 3S)-3-methyl-6-oxo-3,6-dihydro-2H-pyran-2-yl)-8-oxo-nonadeca-2,10,12,16,18-pentaenoic acid Bis-[(2-mercaptoethyl)-amid of (2E,10E,12E,16Z,18E)-(R)-6-hydroxy-3,5, 7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid]

(2-Mercapto-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Methyldisulfanyl-ethyl)-amid of (2E,10E,12E,16Z,18E)-(R)-6-hydroxy-3,5, 7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Methyl-2-methyldisulfanyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Mercapto-2-methyl-propyl)-amid of (2E,10E,12E,16Z, 18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid or their pharmaceutically acceptable salts, hydrates, or hydrated salts, or the polymorphic crystalline structures of these compounds or their optical isomers, racemates, diastereomers or enantiomers.

In order to link the derivative to a cell-binding agent, the derivative must include a moiety (linking group) that allows the derivatives to be linked to a cell binding agent via a linkage such as a disulfide bond, a sulfide (or called herein thioether) bond, an acid-labile group, a photo-labile group, a peptidase-labile group, or an esterase-labile group. The derivatives are prepared so that they contain a moiety necessary to link the leptomycin derivative to a cell binding agent via, for example, a disulfide bond, a thioether bond, an acid-labile group, a photo-labile group, a peptidase-labile group, or an esterase-labile group. In order to further enhance solubility in aqueous solutions, the linking group can contain a polyethylene glycol spacer. Preferably, a sulfide or disulfide linkage is used because the reducing environment of the targeted cell results in cleavage of the sulfide or disulfide and release of the derivatives with an associated increase in cytotoxicity.

Compounds of the present invention may be prepared by a variety of synthetic routes. The reagents and starting materials are commercially available, or readily synthesized by well-known techniques by one of ordinary skill in the art. Methods for synthesizing leptomycin derivatives that may be used in the cytotoxic conjugates of the present invention, along with methods for conjugating said leptomycin derivatives to cell binding agents such as antibodies, are described in detail in in European Patent Application No. 06290948.6, whose content is incorporated herein by reference.

CC-1065 Analogues

The cytotoxic agent used in the cytotoxic conjugates according to the present invention may also be CC-1065 or a derivative thereof.

CC-1065 is a potent anti-tumor antibiotic isolated from the culture broth of *Streptomyces zelensis*. CC-1065 is about 1000-fold more potent in vitro than are commonly used anticancer drugs, such as doxorubicin, methotrexate and vincristine (B. K. Bhuyan et al., 1982, *Cancer Res.*, 42, 3532-3537). CC-1065 and its analogs are disclosed in U.S. Pat. Nos. 6,372,738, 6,340,701, 5,846,545 and 5,585,499.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits.

Although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 µg/kg (V. L. Reynolds et al., 1986, *J. Antibiotics*, XXIX: 319-334). This has spurred efforts to develop analogs that do not cause delayed toxicity, and the synthesis of simpler analogs modeled on CC-1065 has been described (M. A. Warpehoski et al., 1988, *J. Med. Chem.*, 31: 590-603).

In another series of analogs, the CPI moiety was replaced by a cyclopropabenzindole (CBI) moiety (D. L. Boger et al., 1990, *J. Org. Chem.*, 55: 5823-5833; D. L. Boger et al., 1991, *BioOrg. Med. Chem. Lett.*, 1: 115-120). These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results (B. F. Foster et al., 1996, *Investigational New Drugs*, 13: 321-326; I. Wolff et al., 1996, *Clin. Cancer Res.*, 2: 1717-1723). These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described (U.S. Pat. Nos. 5,475,092; 5,585,499; 5,846,545). These conjugates typically display high target-specific cytotoxicity in vitro, and exceptional anti-tumor activity in human tumor xenograft models in mice (R. V. J. Chari et al., 1995, *Cancer Res.*, 55: 4079-4084).

Recently, prodrugs of CC-1065 analogs with enhanced solubility in aqueous medium have been described (European Patent Application No. 06290379.4). In these prodrugs, the phenolic group of the alkylating portion of the molecule is protected with a functionality that renders the drug stable upon storage in acidic aqueous solution, and confers increased water solubility to the drug compared to an unprotected analog. The protecting group is readily cleaved in vivo at physiological pH to give the corresponding active drug. In the prodrugs described in EP 06290379.4, the phenolic substituent is protected as a sulfonic acid containing phenyl carbamate which possesses a charge at physiological pH, and thus has enhanced water solubility. In order to further enhance water solubility, an optional polyethylene glycol spacer can be introduced into the linker between the indolyl subunit and the cleavable linkage such as a disulfide group. The introduction of this spacer does not alter the potency of the drug.

Methods for synthesizing CC-1065 analogs that may be used in the cytotoxic conjugates of the present invention, along with methods for conjugating the analogs to cell binding agents such as antibodies, are described in detail in EP 06290379.4 (whose content is incorporated herein by reference) and U.S. Pat. Nos. 5,475,092, 5,846,545, 5,585,499, 6,534,660 and 6,586,618 and in U.S. application Ser. Nos. 10/116,053 and 10/265,452.

Other Drugs

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs are also suitable for the preparation of conjugates of the present invention. The drug molecules can also be linked to the antibody molecules through an intermediary carrier molecule such as serum albumin. Doxarubicin and Danorubicin compounds, as described, for example, in U.S. Pat. No. 6,630,579, may also be useful cytotoxic agents.

Therapeutic Composition

The invention also relates to a therapeutic composition for the treatment of a hyperproliferative disorder in a mammal which comprises a therapeutically effective amount of a compound of the invention and a pharmaceutically acceptable carrier. In one embodiment said pharmaceutical composition is for the treatment of cancer, including (but not limited to) the following: carcinoma, including that of the bladder, breast, colon, kidney, liver, lung, ovary, pancreas, stomach, cervix, thyroid and skin; including squamous cell carcinoma ; hematopoietic tumors of lymphoid lineage, including leukemia, acute lymphocytic leukemia, acute lymphoblastic leukemia, B-cell lymphoma, T-cell lymphoma, Burkitt's lymphoma ; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma, and other cancers yet to be determined in which EphA is expressed predominantly. In a preferred embodiment, the pharmaceutical compositions of the invention are used for treatment of cancer of the lung, breast, colon, prostate, kidney, pancreas, ovary, cervix and lymphatic organs, osteosarcoma, synovial carcinoma, a sarcoma, head and neck, a glioma, gastric, liver or other carcinomas in which EphA is expressed. In particular, the cancer is a metastatic cancer. In another embodiment, said pharmaceutical composition relates to other disorders such as, for example, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

The instant invention provides pharmaceutical compositions comprising:
an effective amount of an antibody, antibody fragment or antibody conjugate of the present invention, and
a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The compositions herein may also contain a further therapeutic agent, as necessary for the particular disorder being treated. Preferably, the antibody, antibody fragment or antibody conjugate of the present invention, and the supplementary active compound will have complementary activities, that do not adversely affect each other. In a preferred embodiment, the further therapeutic agent is an antagonist of fibroblast-growth factor (FGF), hepatocyte growth factor (HGF), tissue factor (TF), protein C, protein S, platelet-derived growth factor (PDGF), or HER2 receptor.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as a combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The antibody, antibody fragment or antibody conjugate of the present invention may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Therapeutic Methods of Use

In another embodiment, the present invention provides a method for inhibiting the EphA2 receptor activity by administering an antibody which antagonizes said EphA2 receptor, to a patient in need thereof. Any of the type of antibodies, antibody fragments, or cytotoxic conjugates of the invention, may be used therapeutically. The invention thus includes the use of antagonistic anti-EphA2 antibodies, fragments thereof, or cytotoxic conjugates thereof as medicaments.

In a preferred embodiment, antibodies, antibody fragments, or cytotoxic conjugates of the invention are used for the treatment of a hyperproliferative disorder in a mammal. In a more preferred embodiment, one of the pharmaceutical compositions disclosed above, and which contains an antibody, antibody fragment, or cytotoxic conjugate of the invention, is used for the treatment of a hyperproliferative disorder in a mammal. In one embodiment, the disorder is a cancer. In particular, the cancer is a metastatic cancer. The antibodies, antibody fragments, and cytotoxic conjugates of the invention can also be used to treat the neovascularization of said cancer tumor.

Accordingly, the pharmaceutical compositions of the invention are useful in the treatment or prevention of a variety of cancers, including (but not limited to) the following: carcinoma, including that of the bladder, breast, colon, kidney, liver, lung, ovary, pancreas, stomach, cervix, thyroid and skin; including squamous cell carcinoma ; hematopoietic tumors of lymphoid lineage, including leukemia, acute lymphocytic leukemia, acute lymphoblastic leukemia, B-cell lymphoma, T-cell lymphoma, Burkitt's lymphoma ; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma, and other cancers yet to be determined in which EphA is expressed predominantly. In a preferred embodiment, the cancer is a cancer of the lung, breast, colon, prostate, kidney, pancreas, uterus, ovary, cervix and lymphatic organs, osteosarcoma, synovial carcinoma, a sarcoma, head and neck, a glioma, gastric, liver or other carcinomas in which EphA is expressed. In another embodiment, said pharmaceutical composition relates to other disorders such as, for example, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

Similarly, the present invention provides a method for inhibiting the growth of selected cell populations comprising contacting target cells, or tissue containing target cells, with an effective amount of an antibody, antibody fragment or antibody conjugate of the present invention, or an antibody, antibody fragment or a therapeutic agent comprising a cytotoxic conjugate, either alone or in combination with other cytotoxic or therapeutic agents.

The method for inhibiting the growth of selected cell populations can be practiced in vitro, in vivo, or ex vivo. As used herein, "inhibiting growth" means slowing the growth of a cell, decreasing cell viability, causing the death of a cell, lysing a cell and inducing cell death, whether over a short or long period of time.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent graft versus host disease (GVHD). Treatment can be carried out as follows. Bone marrow is harvested from the patient or other individual and then incubated in medium containing serum to which is added the cytotoxic agent of the invention. Concentrations range from about 10 µM to 1 µM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the antibody, the epitope-binding antibody fragment, or the cytotoxic conjugate of the invention will be supplied as solutions that are tested for sterility and for endotoxin levels. Examples of suitable protocols of cytotoxic conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 µg to 100 mg per administration, i.v. (range of 100 ng to 1 mg/kg per day). More preferably, dosages will range from 50 µg to 30 mg. Most preferably, dosages will range from 1 mg to 20 mg. After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Diagnostic

The antibodies or antibody fragments of the invention can also be used to detect EphA2 in a biological sample in vitro or in vivo. In one embodiment, the anti-EphA2 of the invention are used to determine the level of EphA2 in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of EphA2 in the tissue or biopsy can then be determined in an immunoassay with the antibodies or antibody fragments of the invention. The tissue or biopsy thereof can be frozen or fixed. The same method can be used to determine other properties of the EphA2 protein, such as its level of tyrosine phosphorylation, cell surface levels, or cellular localization.

The above-described method can be used to diagnose a cancer in a subject known to or suspected to have a cancer, wherein the level of EphA2 measured in said patient is compared with that of a normal reference subject or standard. Said method can then be used to determine whether a tumor expresses EphA2, which may suggest that the tumor will respond well to treatment with the antibodies, antibody fragments or antibody conjugates of the present invention. Preferrably, the tumor is a cancer of the lung, breast, colon, prostate, kidney, pancreas, uterus, ovary, cervix and lymphatic organs, osteosarcoma, synovial carcinoma, a sarcoma, a glioma, gastric, liver, head and neck or other carcinomas in which EphA2 is expressed, and other cancers yet to be determined in which EphA2 is expressed predominantly.

The present invention further provides for monoclonal antibodies, humanized antibodies and epitope-binding fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, and the distribution of the label within the body of the subject is measured or monitored.

Kit

The present invention also includes kits, e.g., comprising a described cytotoxic conjugate and instructions for the use of the cytotoxic conjugate for killing of particular cell types. The instructions may include directions for using the cytotoxic conjugates in vitro, in vivo or ex vivo.

Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

EXAMPLES

Example 1

Generation of Anti-EphA2 Monoclonal Antibody Hybridomas

Four BALB/c VAF mice were immunized with human EphA2-transfected 300-19 cells, a pre-B cell line derived from a BALB/c mouse. The stably transfected cells overexpressing the antigen were generated by transfection of 300-19 cells with the full-length human EphA2 cDNA and selected for the high expression clones by flow cytometry. Clone 4-6, a clone that highly expresses the human EphA2 receptor on the cell surface, was selected as immunogen for immunization of mice and for antibody screening of hybridomas. The EphA2-transfected cells were maintained in the selection medium containing G418 at a final concentration of 1 mg/mL and were tested for the EphA2 expression regularly using a commercially available antibody.

The Balb/c mice were subcutaneously injected with approximately $5 \times 10^6$ EphA2-transfected 300-19 cells in 200 µL of phosphate buffered saline (PBS) per mouse. The injections are performed every 2-3 weeks by standard immunization protocols used at ImmunoGen, Inc. Three days before cell fusion, the mice were intraperitoneally boosted one more time with the same dose of antigen, and sacrificed for the preparation of spleen cells according to the standard protocols for animal use procedures on the day of cell fusion.

The spleen was collected from the immunized mouse under sterilized surgical conditions and was ground between two sterile and frosted microscopic slides to obtain single cell suspension in RPMI-1640 medium. The splenocytes were pelleted and washed twice with RPMI-1640 medium before cell fusion. The spleen cells were mixed and fused with murine myeloma P3X63Ag8.653 cells (Kearney, J. F. et al., 1979. *J. Immunol.*, 123: 1548-1550) using polyethylene glycol-1500 as fusogen (Roche 783 641). After cell fusion and centrifugation, the cells were suspended in complete RPMI-1640 medium (200 mL) containing hypoxanthine-aminopterin-thymidine (HAT) supplement (Sigma H-0262), and were plated into ten 96-well flat-bottomed plates (Corning-Costar 3596, 200 µL of cell suspension per well). Following incubation at 37° C., 5% $CO_2$ for 5 days, 100 µL of culture supernatant were removed from each well of the plates and replaced with an equal volume of complete RPMI-1640 medium containing hypoxanthine-thymidine (HT) supplement (Sigma H-0137). The incubation (in an atmosphere of 5% $CO_2$ at 37° C.) was continued until hybridoma clones had grown large enough colonies for antibody screening.

On day 10 post-fusion when hybridoma cells had grown to half confluence in the wells and the supernatant had changed to an orange color, hybridoma supernatants were sampled from the fusion plates for antibody screening by immunoassays. For preliminary screening, hybridoma supernatants were tested on EphA2-transfected cells vs. the parental 300-19 cells by flow cytometry. Cells were stained with 50 µL of hybridoma supernatant, followed by incubation with fluorescein-goat anti-mouse IgG (H+L) conjugate, and analyzed by flow cytometry with Becton Dickinson FACSCalibur or FACSArray machine. Hybridoma clones that analyzed positive for EphA2-transfected cells but negative for 300-19 cells were selected, expanded, frozen for storage, or subcloned by limiting dilutions to attain a monoclonal population. The specific antibodies secreted by hybridoma cells were isotyped using commercially available isotyping reagents (Roche 1493027).

Based on flow cytometric data, 29 hybridoma clones, which were specifically reactive with human EphA2-transfected cells but not with the parental 300-19 cells, were identified and selected from the immunization of mice with human EphA2 antigens.

Example 2

Binding Characterization of Anti-EphA2 Antibodies, 37.3D7, 37.1F5, 53.2H11, EphA2-N1 and EphA2-N2

The specific binding of each of the purified anti-EphA2 antibodies, 37.3D7, 37.1F5 and 53.2H11 was demonstrated by fluorescence activated cell sorting (FACS) using cells overexpressing human EphA2 and by using cells that do not express EphA2 (FIGS. 1A, B, and C). Incubation of 37.3D7 antibody, or 37.1F5 antibody or 53.2H11 antibody (60 nM) in 100 µl cold FACS buffer (1 mg/mL BSA in Dulbecco's MEM medium) was performed using cells overexpressing EphA2 and cells that do not express EphA2 in a round-bottom 96-well plate on ice. After 1 h, the cells were pelleted by centrifugation and washed with cold FACS buffer and then incubated with goat-anti-mouse IgG-antibody-FITC conjugate (100 µL, 6 µg/ml in FACS buffer) on ice for 1 h. The cells were then pelleted, washed, and resuspended in 200 µL of 1% formaldehyde solution in PBS. The cell samples were then analyzed using a FACSCalibur reader (BD Biosciences).

Figure 1B:
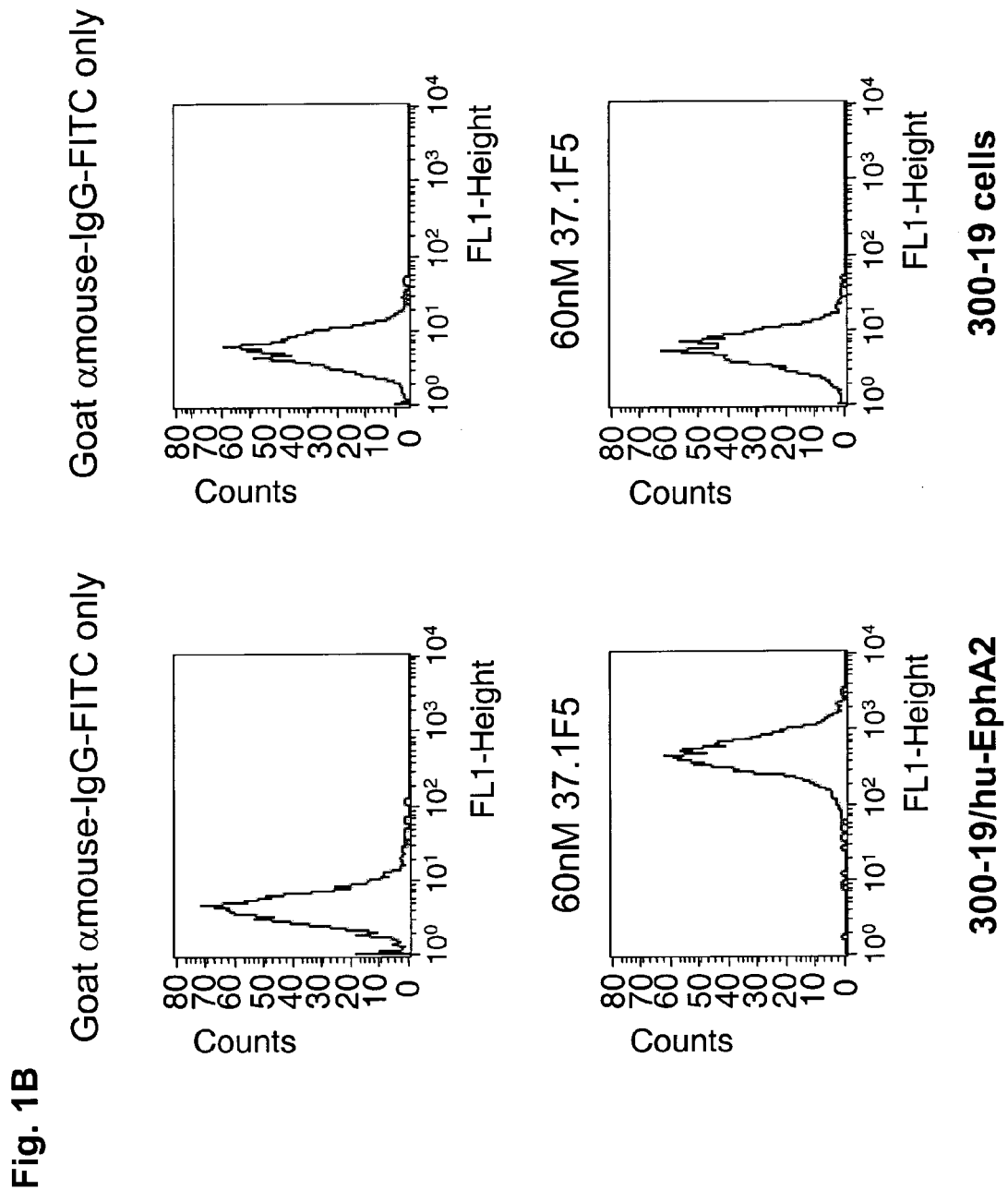
FIG. 1 shows the analysis of the specific binding of anti-EphA2 antibodies to cells overexpressing human EphA2 (300-19/hu-EphA2 cells) by FACS analysis.
Figure 1C:
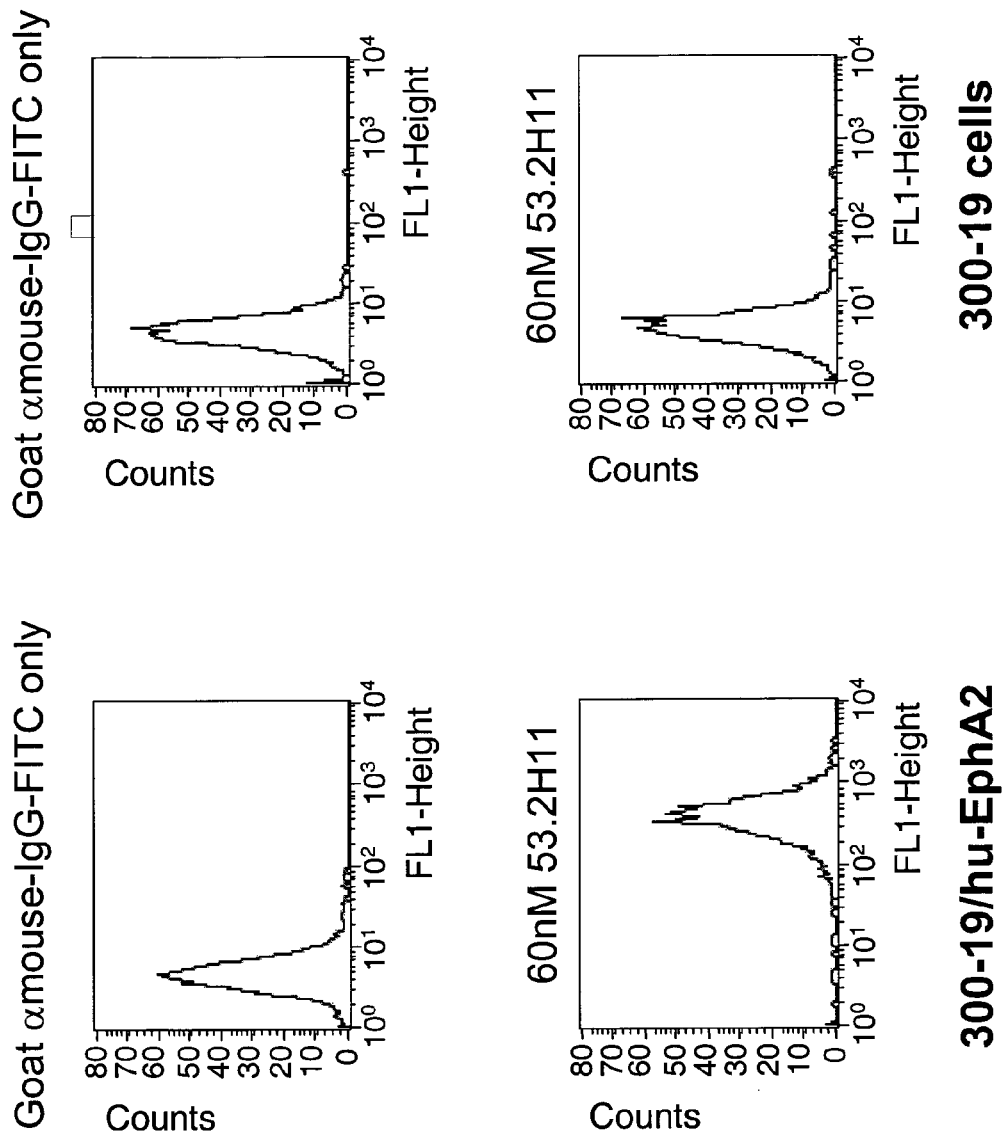
Figure 2:
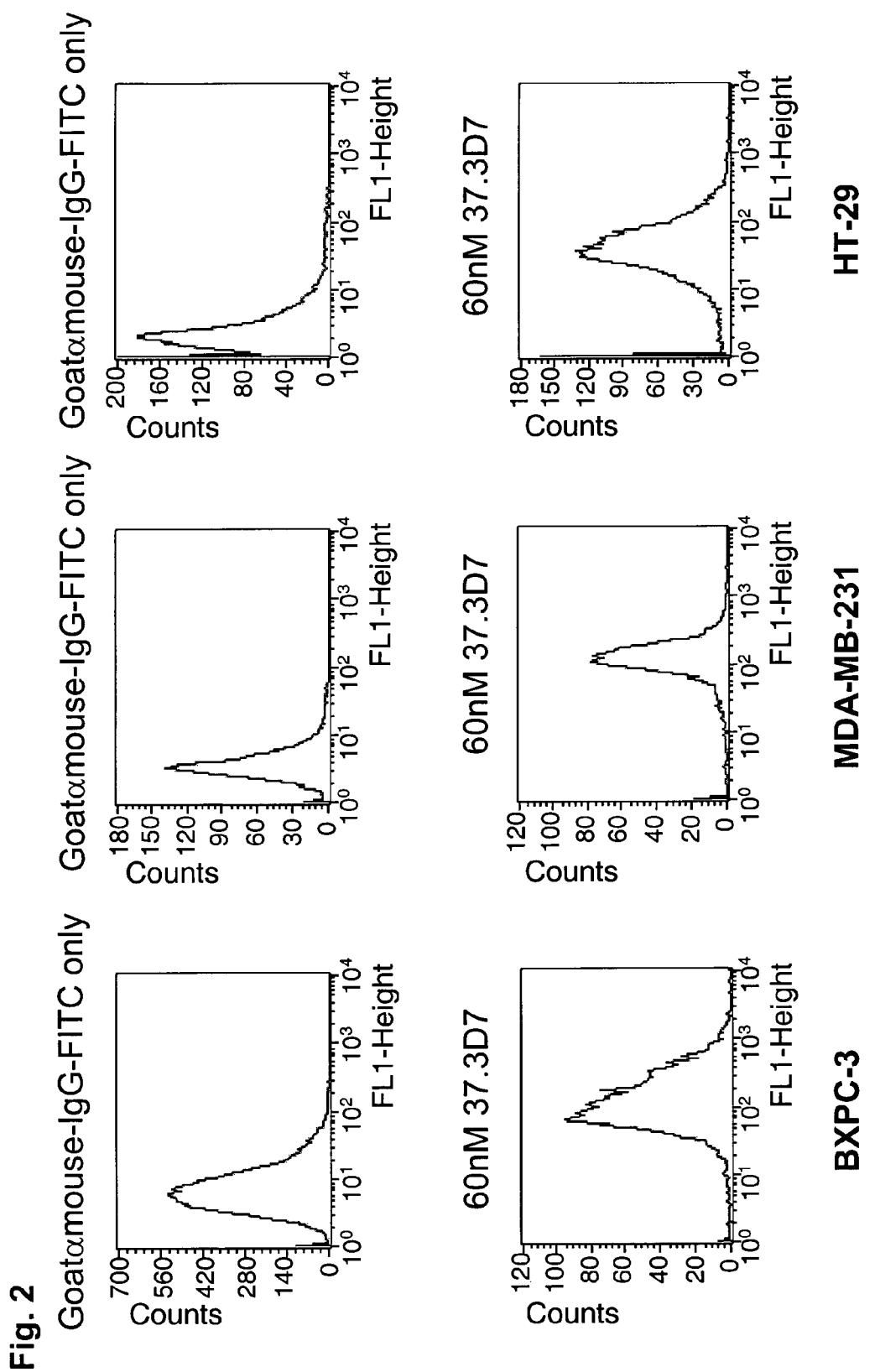
FIG. 2 shows the specific binding of purified 37.3D7 antibody to BxPC3 human pancreatic cancer cells, MDA-MB-231 human breast cancer cells, and HT-29 human colon cancer cells. Histograms of FACS analysis are shown.

A strong fluorescence shift was obtained upon incubation of human EphA2-overexpressing cells with 37.3D7, 37.1F5, or 53.2H11 antibody, in contrast to an insignificant shift upon incubation of cells that do not express human EphA2 with 37.3D7, 37.1F5, or 53.2H11 antibody (FIGS. 1A, 1B, and 1C), which demonstrates that the 37.3D7, 37.1F5 and 53.2H11 antibodies were selectively binding to human EphA2. The positive control anti-EphA2 antibody, B2D6 (Upstate), showed a similar fluorescence shift upon incubations with cells that over-expressed human EphA2 (FIG. 1A). A strong fluorescence shift was also observed by FACS assay using 37.3D7 and human cancer cells, such as human breast cancer MDA-MB-231 cells, human colon cancer HT-29 cells, human pancreatic cancer BxPC3 cells, which shows that 37.3D7 antibody binds to human EphA2 on the surface of human tumor cells (FIG. 2). Similar data were also obtained using 37.1F5 and 53.2H11 antibodies with human tumor cell lines.

The apparent dissociation constants ($K_D$) for the binding of 37.3D7, 37.1F5 and 53.2H11 antibodies with human EphA2 on the surface of cells was determined by FACS assays of the binding of antibody at several concentrations to cells over expressing human EphA2 and human breast cancer MDA-MB-231 cells (FIG. 3). The values of $K_D$ were estimated by non-liner regression for one-site binding. The binding curves yielded the apparent $K_D$ values of 0.3 nM for 37.3D7 antibody, 0.07 nM for 37.1F5 antibody, and 0.14 nM for 53.2H11 antibody (FIGS. 3A, 3C, and 3E).

Using the same experimental protocol, apparent kD values of 0.18 nM and 0.05 nM were determined for EphA2-N1 and EphA2-N2, respectively.

Figure 4A:
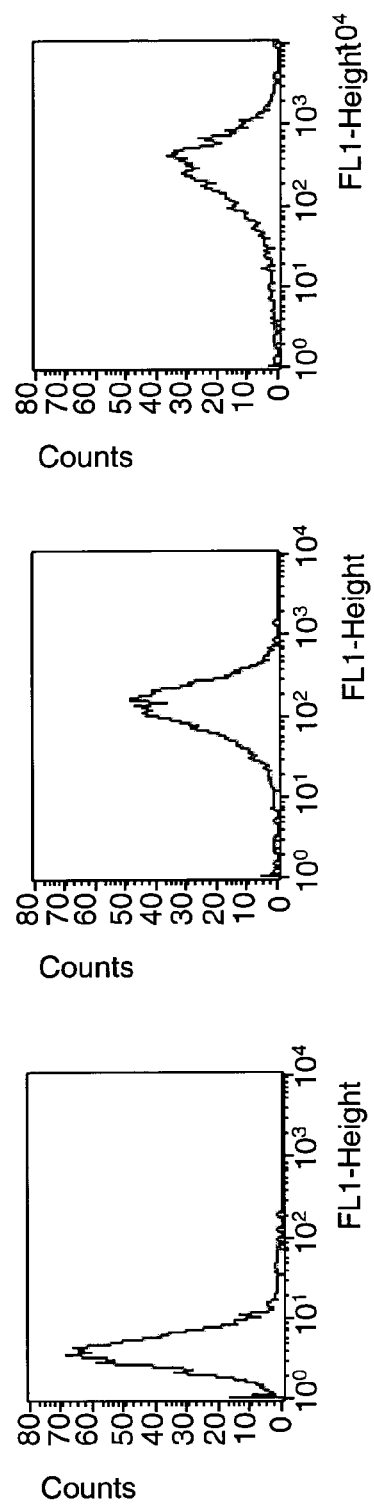
FIG. 4A shows the data for cells overexpressing murine EphA2 (300-19/mu-EphA2) and FIG. 4B shows the data for cells overexpressing rat EphA2 (300-19/rat-EphA2).
Figure 4B:
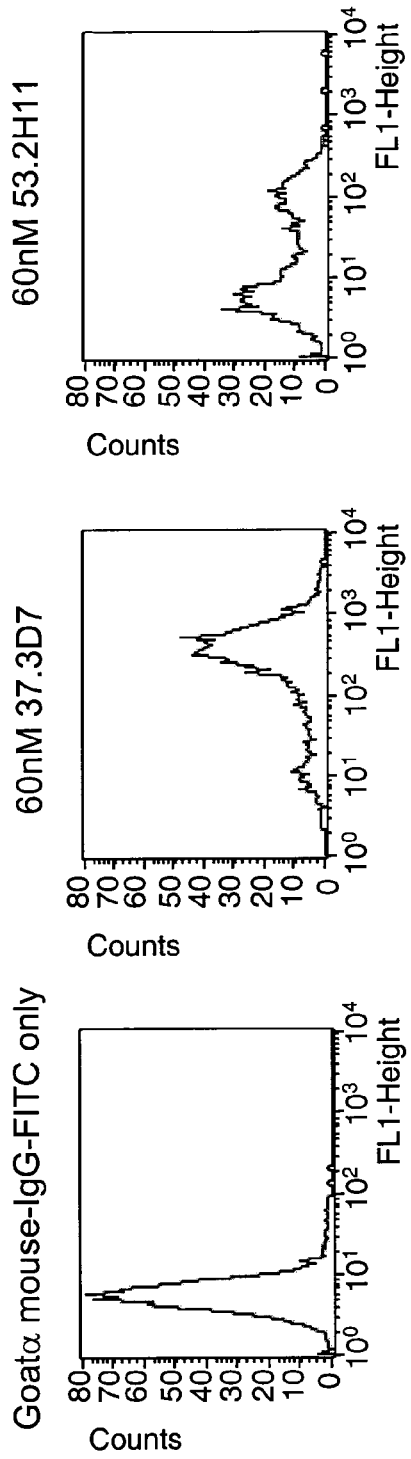
Figure 5:
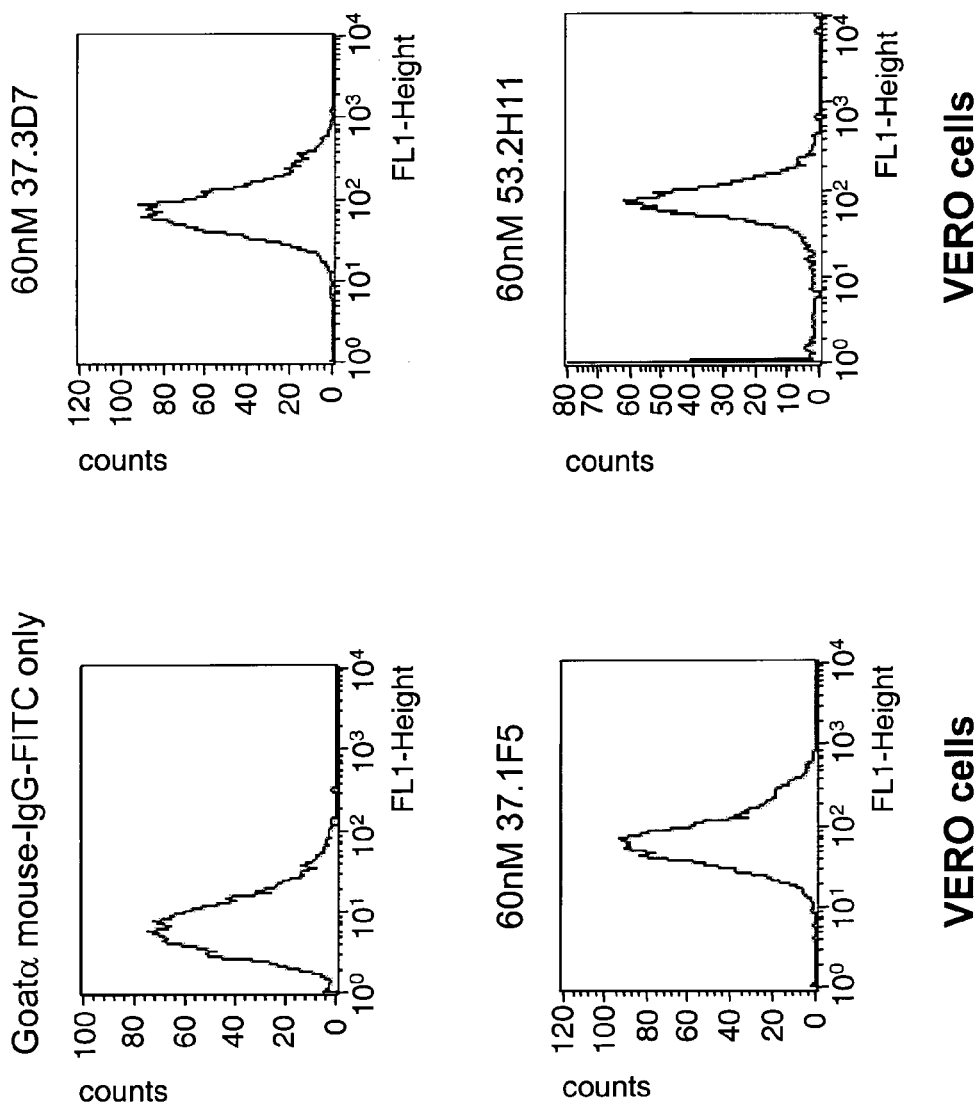
FIG. 5A shows the specific binding of purified 37.3D7, 37.1F5, and 53.2H11 antibodies to VERO monkey kidney epithelial cells. Histograms of FACS analysis are shown.
FIG. 5B shows the binding curves for the antibodies 37.3D7, 37.1F5, and 53.2H11 established with VERO monkey kidney epithelial cells.
Figure 5:
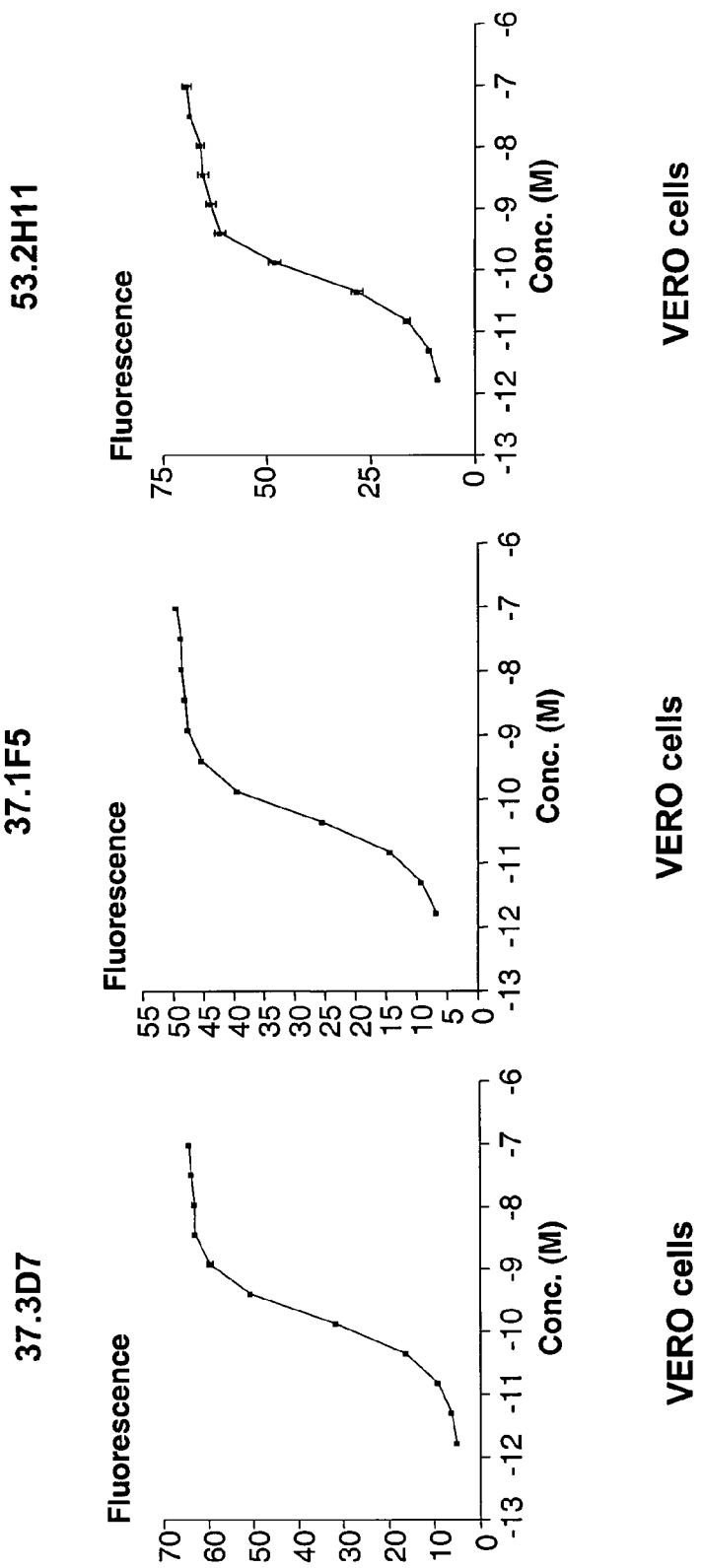

A strong fluorescence shift was obtained upon incubation of cells that over-express murine EphA2 or rat EphA2 with 37.3D7 antibody or 53.2H11 antibody, in contrast to an insignificant shift upon incubation of cells that do not express murine EphA2 or rat EphA2 with 37.3D7 antibody or 53.2H11 antibody (FIG. 4), which demonstrates that the 37.3D7 and 53.2H11 antibodies bind also to murine EphA2 and rat EphA2. A strong fluorescence shift was also observed by FACS assay using 37.3D7 or 37.1F5 or 53.2H11 antibody with monkey (Cercopithecus aethiops) epithelial VERO cells (FIG. 5A), which shows that 37.3D7, 37.1F5 and 53.2H11 bind to monkey EphA2 as well. The apparent values of $K_D$ were estimated by non-liner regression for one-site binding. The binding curves by FACS assay yielded $K_D$ values of 0.15 nM for 37.3D7, 0.05 nM for 37.1F5, and 0.07 nM for 53.2H11 on monkey cells (FIGS. 5B, 5D and 5F).

Example 3

Figure 6:
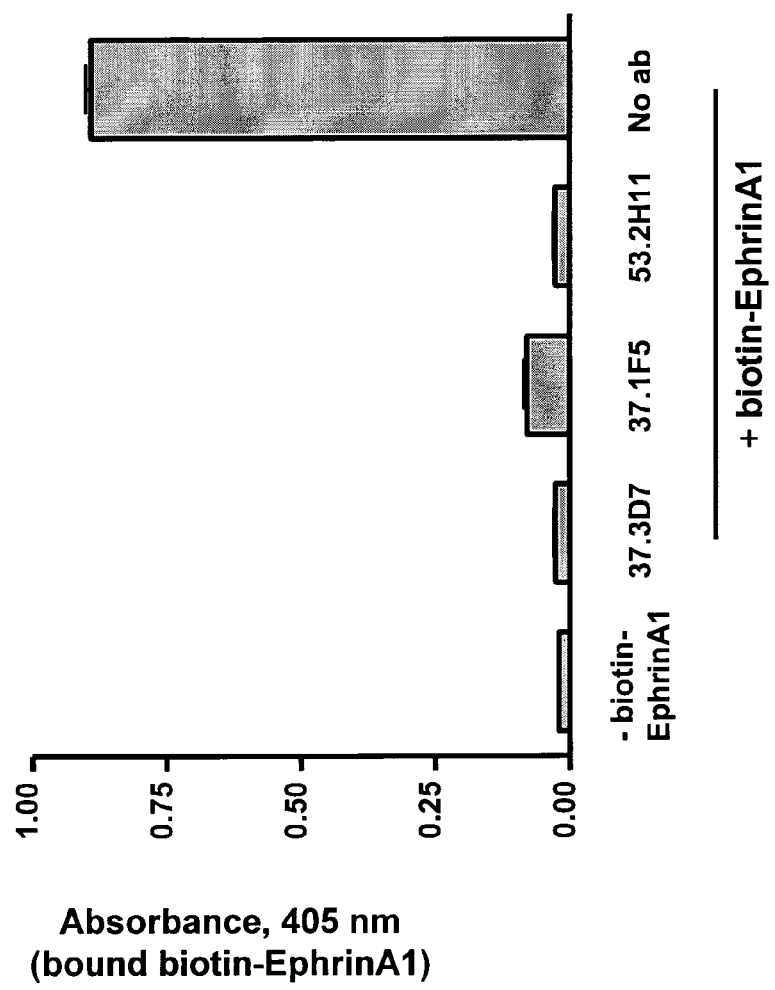
FIG. 6 shows the inhibition of the binding of biotinylated ephrinA1 to mammary MDA-MB-231 human breast cancer cells by 37.3D7, 37.1F5, and 53.2H11 antibodies.

Inhibition of Binding of EphrinA1 to MDA-MB-231 cells by 37.3D7, 37.1F5, 53.2H11, EphA2-N1 and EphA2-N2 Antibodies The binding of ephrinA1 to MDA-MB-231 human breast cancer cells was inhibited by 37.3D7, 37.1F5 and 53.2H11 antibodies (FIG. 6). MDA-MB-231 cells were incubated with or without 5 μg/mL 37.3D7, 37.1F5, or 53.2H11 antibody for 2 h, followed by incubation with 100 ng/mL biotinylated ephrinA1 for 30 min at 4° C. The cells were then washed twice with serum-free medium to remove unbound biotin-ephrinA1, and were then lysed in 50 mM HEPES buffer, pH 7.4, containing 1% NP-40 and protease inhibitors. An Immulon-2HB ELISA plates were coated with a mouse monoclonal anti-EphA2 antibody (D7, Upstate) and were used to capture the EphA2 and bound biotin-ephrinA1 from the lysate. The binding of the coated antibody to the cytoplasmic C-terminal domain of the EphA2 did not interfere with the binding of biotin-ephrinA1 to the extracellular domain of EphA2. The wells were washed, incubated with streptavidin-horseradish peroxidase conjugate, washed again, and then developed with ABTS/$H_2O_2$ substrate. The inhibition of ephrinA1 binding to MDA-MB-231 cells by 5 μg/mL 37.3D7, 37.1F5, or 53.2H1 antibody was essentially quantitative; the signal was almost equivalent to that of the ELISA background signal obtained using a control lacking biotin-ephrinA1 (FIGS. 6A, 6B and 6C).

Both EphA2-N1 and Epha2-N2 were capable of inhibiting binding of human ephrinA1 to MDA-MB-231 cells to the same extent as 37.3D7.

Example 4

Inhibition of EphA2 Mediated Cell Signaling by 37.3D7, 37.1F5, 53.2H11, EphA2-N1 and EphA2-N2 Antibodies Treatment of MDA-MB-231 human breast cancer cells with 37.3D7, or 37.1F5 antibody completely inhibited intracellular EphA2 receptor signaling as shown by the inhibition of EphA2 receptor autophosphorylation (FIG. 7A) and by the inhibition of phosphorylation of its downstream effectors such as Akt (FIG. 7B). Treatment of pancreatic cancer CFPAC-1 cells with 37.3D7 antibody or 53.2H11 antibody completely inhibited intracellular EphA2 receptor signaling as shown by the inhibition of EphA2 receptor autophosphorylation (FIG. 7C).

In FIGS. 7A and 7C, the mammary MDA-MB-231 cells or the pancreatic CFPAC-1 cells were grown in regular medium (as suggested from ATCC for each cell line) with serum for 3 days, then cultured in serum-free medium for 12-14 h. Serum-starved cells were treated with 15 μg/mL 37.3D7, 37.1F5, or 53.2H11 antibody or control $IgG_1$ for 2 h, followed by stimulation with 1 μg/mL ephrin A1-Fc (R&D) for 10 min at 37° C. The cells were then lysed in ice-cold lysis buffer containing protease and phosphatase inhibitors (50 mM HEPES buffer, pH 7.4, 1% NP-40, 1 mM sodium orthovanadate, 100 mM sodium fluoride, 10 mM sodium pyrophosphate, 2.5 mM EDTA, 10 μM leupeptin, 5 μM pepstatin, 1 mM PMSF, 5 mM benzamidine, and 5 μg/mL aprotinin). The lysates were immunoprecipitated with anti-EphA2 antibody D7 (Upstate) coupled to protein A/G beads. The immunoprecipitated EphA2 was resolved on an SDS-polyacrylamide gel and Western blotted with phosphotyrosine specific monoclonal antibody, 4G10 (Cell Signaling Technology). To evaluate the EphA2 protein level in each immunoprecipated sample, the same membrane was re-blotted with anti-EphA2 antibody, D7 (Upstate). Use of a control antibody showed no inhibition of the ephrin A1-stimulated autophosphorylation of EphA2 receptor (FIG. 7C). In contrast, a complete inhibition of the ephrinA1-stimulated autophosphorylation of EphA2 receptor was obtained upon treatment with 37.3D7, 37.1F5, or 53.2H11 antibody (FIGS. 7A and 7C). The ephrin A1-stimulated activation of the downstream effectors, such as Akt, was also inhibited in MDA-MB-231 cells by 37.3D7 or 37.1F5 antibody, as shown using Western blots of lysates and rabbit polyclonal anti-phospho-$Ser^{473}$ Akt antibody (Cell Signaling Technology) (FIG. 7B).

The 37.3D7 and 53.2H11 antibodies by themselves did not stimulate EphA2 autophosphorylation in human breast cancer MDA-MB-231 cells, in contrast to the stimulatory effect of ephrinA1 on EphA2 autophosphorylation in MDA-MB-231 cells (FIGS. 8A and 8B). Similar data were obtained for the 37.1F5 antibody using MDA-MB-231 cells. In FIG. 8, the MDA-MB-231 cells were grown in regular medium with serum for 3 days, then cultured in serum-free medium for 12-14 h. Serum-starved cells were treated with 1 μg/mL ephrinA1-Fc or 15 μg/mL 37.3D7 or 53.2H11 antibody for 10 min. The cell lysates were subjected to immunoprecipitation with anti-EphA2 antibody, D7 (Upstate). After separation on a SDS-polyacrylamide gel, the blot was probed with anti-phosphotyrosine antibody, 4G10 (Cell Signaling Technology) and anti-EphA2 antibody D7 (Upstate). Similar results were obtained with both EphA2-N1 and EphA2-N2 in human breast cancer MDA-MB-231 cells, as neither antibody stimulates EphA2 autophosphorylation by itself, whereas each of them prevents ephrinA1-dependent phosphorylation of the EphA2 receptor.

The 37.3D7, 37.1F5, 53.2H11, EphA2-N1, and EphA2-N2 antibodies are therefore unique among all known anti-EphA2 antibodies in their effectiveness to inhibit ephrinA1-stimulated EphA2 intracellular signaling.

Example 5

Inhibition of Serum-Stimulated Growth and Survival of Human Tumor Cells by 37.3D7 and 53.2H11 Antibodies Several human tumor cell lines were tested in serum-free conditions for their growth and survival response to serum in the presence of 37.3D7 or 53.2H11 antibody. Approximately 3000 cells/well were plated in a 96-well plate in regular medium (as suggested from ATCC for each cell line) with serum, which was replaced with serum-free medium the following day.

After one day of growth in serum-free medium, the cells were incubated with 15 μg/mL 37.3D7 antibody or 53.2H11 antibody or control $IgG_1$ followed by the addition of serum to obtain a final concentration of 1% or 1.5% serum. The cells were then allowed to grow for another 3 days. A solution of MTT [3-(4, 5)-dimethylthiazol-2-yl-2,3-diphenyltetrazolium bromide; 25 μL of a 5 mg/mL solution in PBS] was then added and the cells were returned to the incubator for 2-3 h. The medium was then removed and replaced by 100 μL DMSO, mixed, and the absorbance of the plate was measured at 545 nm. Several human tumor cell lines showed a growth and survival response upon addition of serum that was significantly inhibited by 37.3D7 or 53.2H11 antibody. As examples, the findings with the colon tumor cell lines, HT-29, LoVo; the pancreatic tumor cell line, CFPAC-2, BxPC3; and melanoma UACC-257 are shown.

Figure 9C:
Figure 9D:
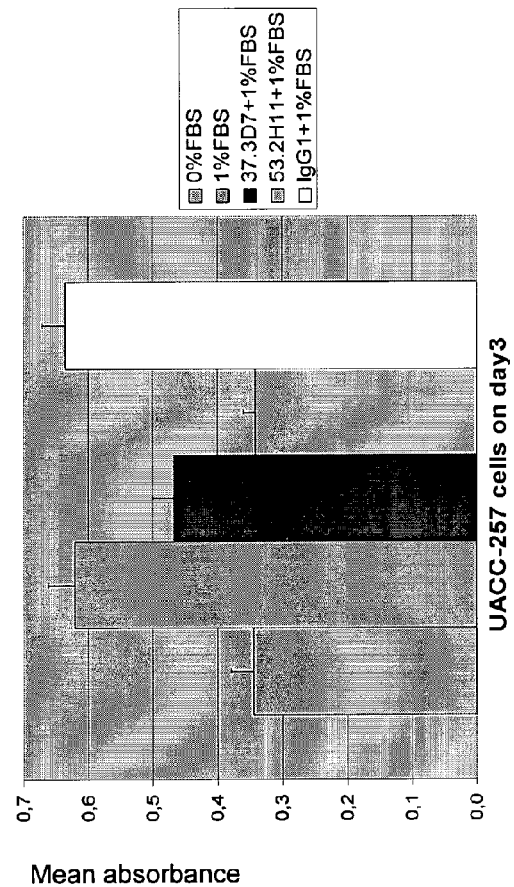
Figure 10A:
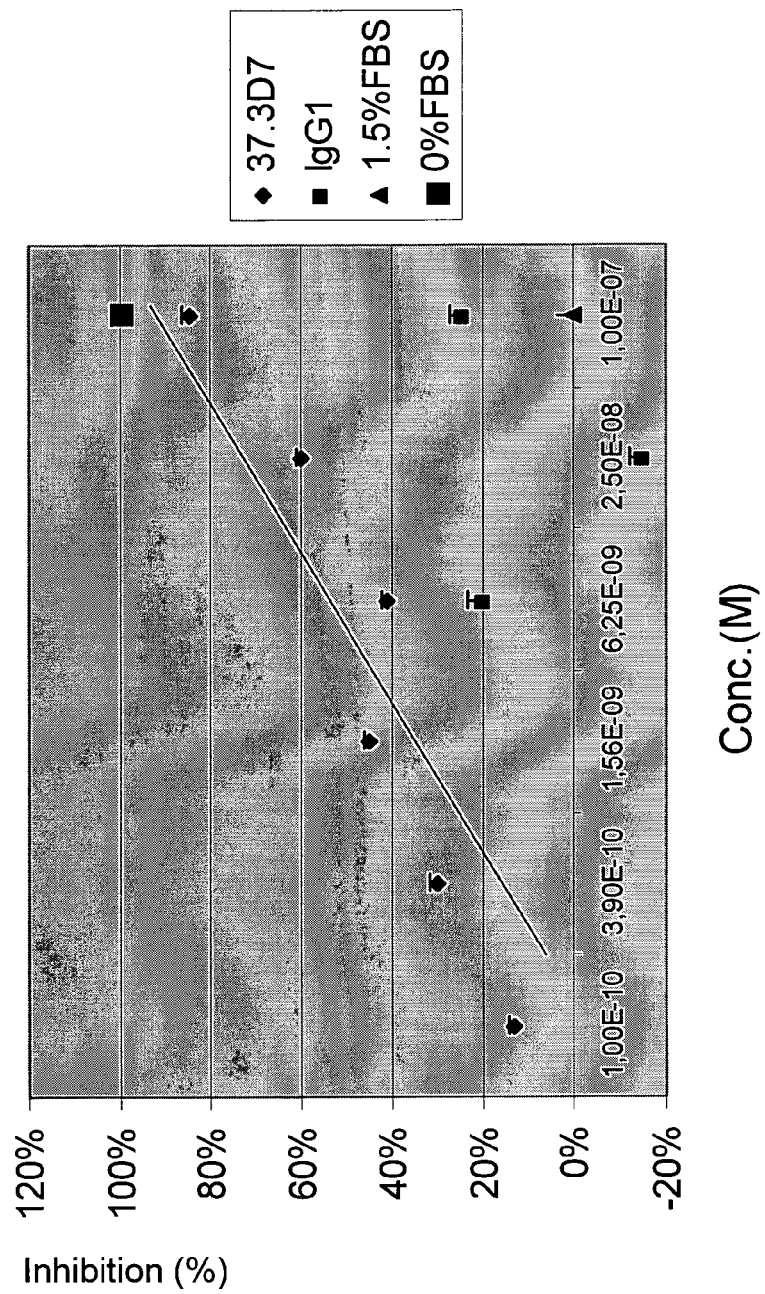
FIG. 10A shows the dose-dependent inhibition of serum-stimulated growth of pancreatic BxPC3 cells by 37.3D7 antibody.
Figure 10B:
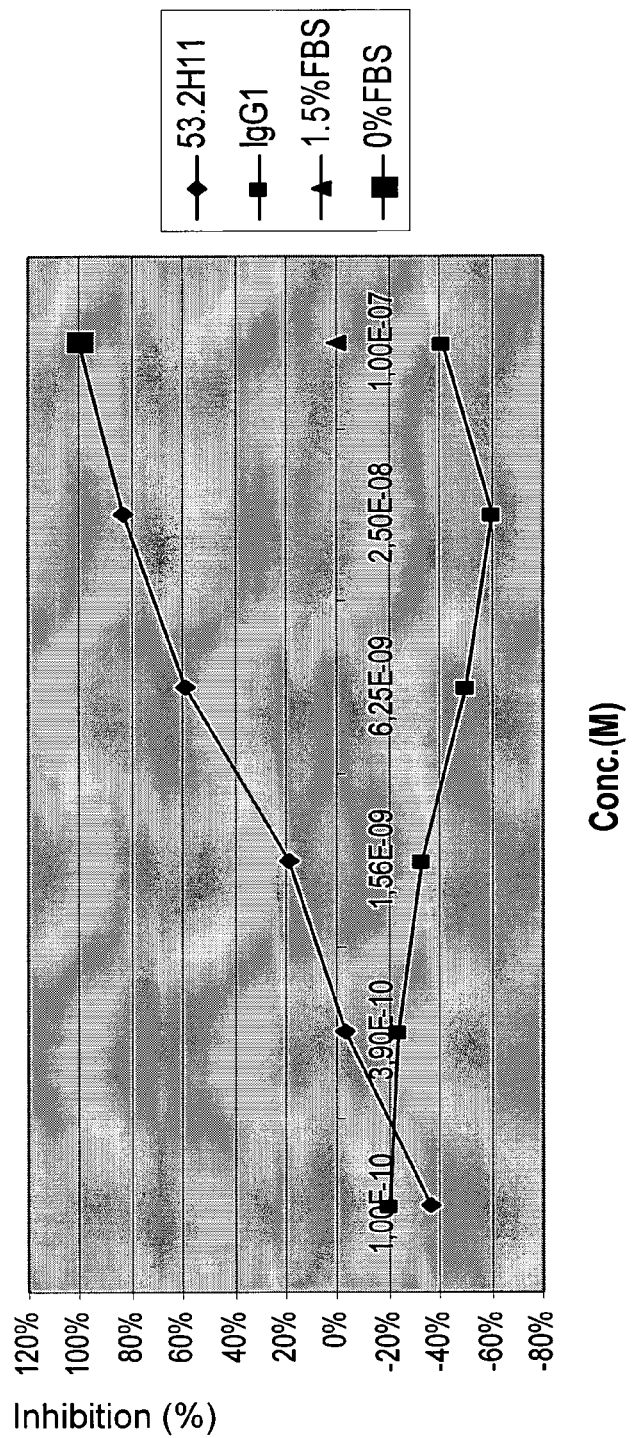
FIG. 10B shows the dose-dependent inhibition of serum-stimulated growth of colon LoVo cells by the 53.2H11 antibody.
Figure 10C:
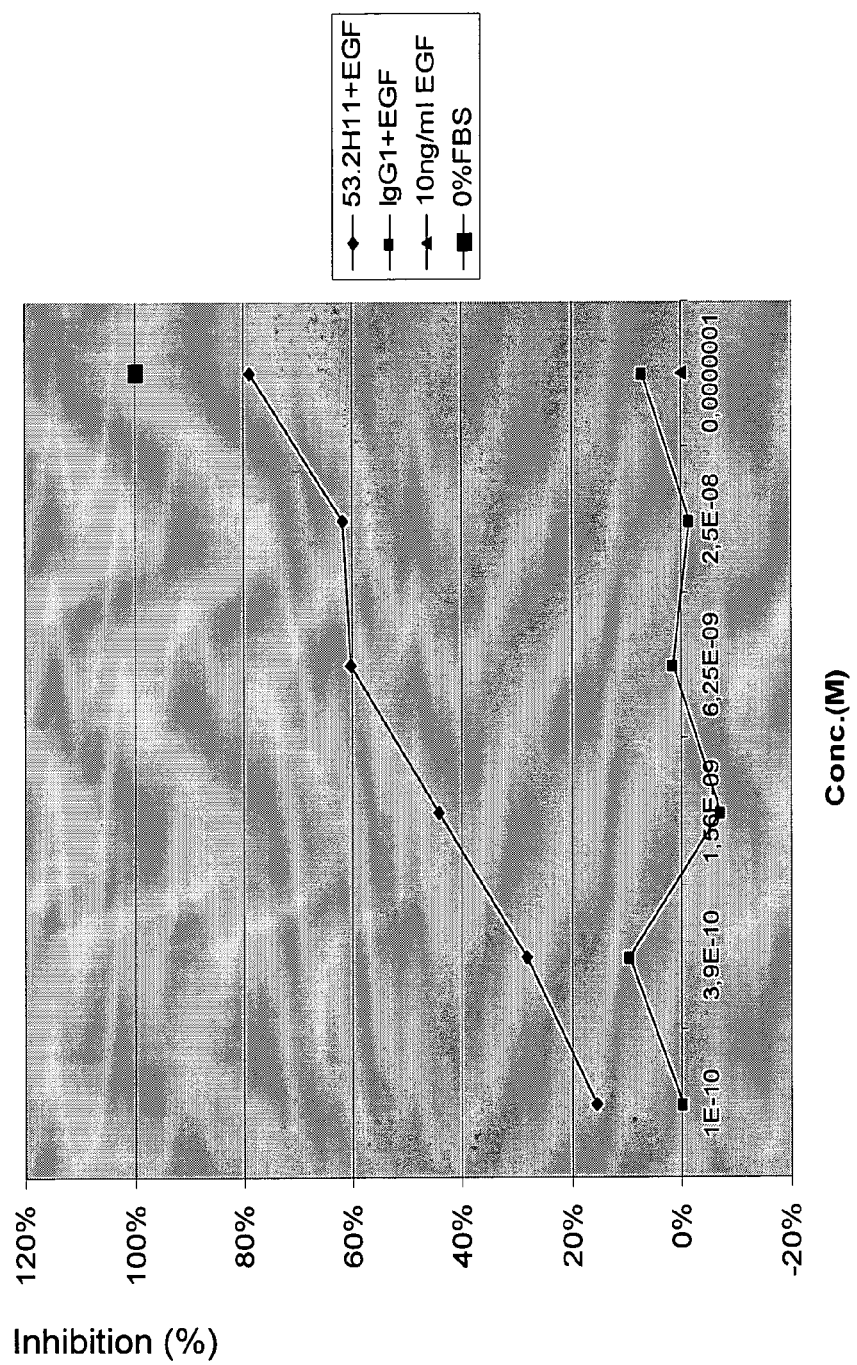
FIG. 10C shows the dose-dependent inhibition of EGF-stimulated growth of colon LoVo cells by 53.2H11 antibody.

The 37.3D7 antibody strongly inhibited serum-stimulated growth and survival of human colon cancer HT-29 cells (FIG. 9A). In another experiment, the 37.3D7 antibody strongly inhibited serum-stimulated growth and survival of BxPC3 human pancreatic cancer cells in a dose-dependent manner with an $IC_{50}$ value of 4 nM (FIG. 10A). In addition, the 37.3D7 or 53.2H11 antibody strongly inhibited serum-stimulated growth and survival of LoVo human colon cancer cells (FIG. 9B), CFPAC-1 human pancreatic cancer cells (FIG. 9C) and UACC-257 melanoma cancer cells (FIG. 9D) and the 53.2H11 antibody inhibited serum or EGF-stimulated growth and survival of LoVo cells in a dose-dependent manner with an $IC_{50}$ value of 2 nM (FIGS. 10B and 10C). In FIG. 10, $OD_{545}$ values for 0% serum-treated samples were set to 100% inhibition and 0% inhibition was set using samples treated with 1.5% serum or 10 ng/ml EGF. None of the previous reported anti-EphA2 antibodies have inhibitory activities on the anchorage-dependent (monolayer) growth of human tumor cells. Therefore, 37.3D7 and 53.2H11 antibodies are unique in their ability to inhibit anchorage-dependent growth (monolayer growth) of human tumor cells.

Example 6

Figure 11A:
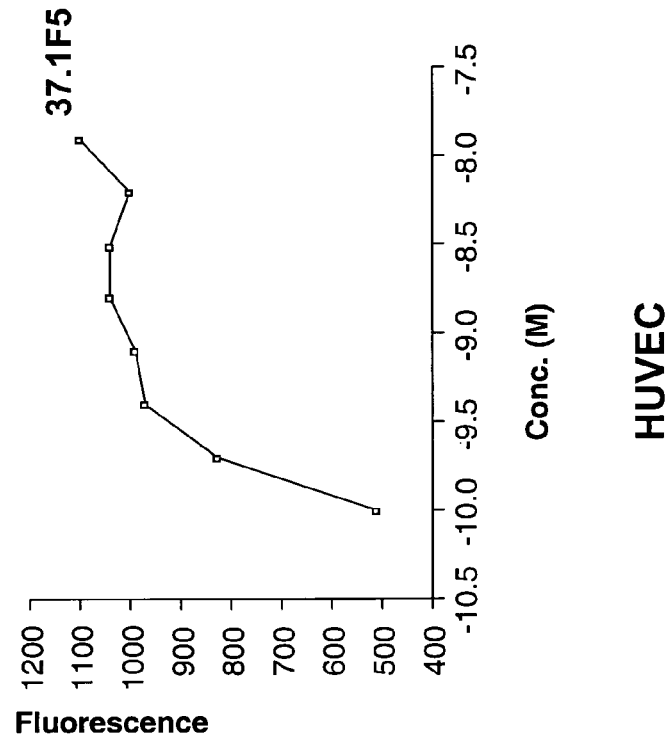
FIG. 11A shows the binding curve of 37.3D7 antibody to HUVEC cells.
Figure 11B:
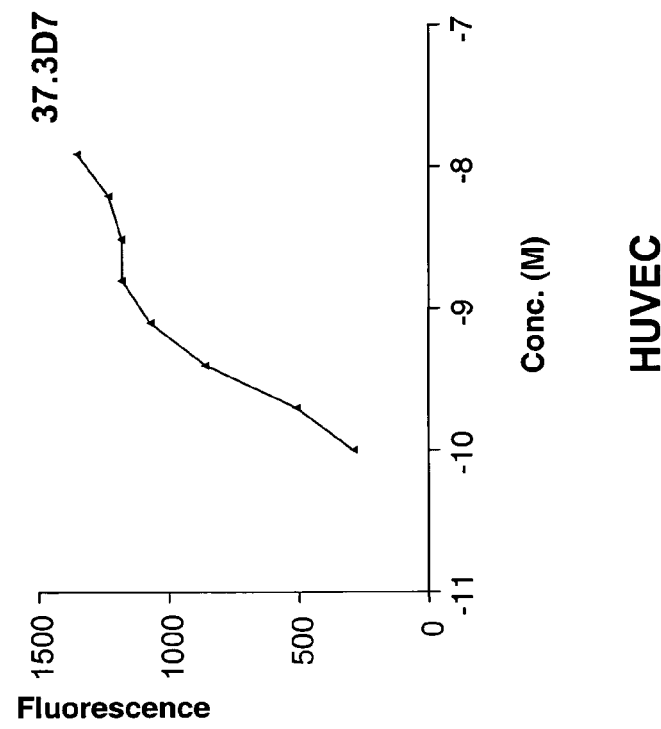
FIG. 11B shows the binding curve of 37.1F5 antibody to HUVEC cells.

Inhibition of VEGF-Mediated Cell Signaling and VEGF-Stimulated Growth and Survival of Human Umbilical Vein Endothelial Cells (HUVECs) by 37.3D7, 37.1F5, and 53.2H11 Antibody A strong fluorescence shift was obtained upon incubation of HUVEC cells with 37.3D7, 37.1F5, or 53.2H11 antibody by FACS analysis, indicating that 37.3D7, 37.1F5 and 53.2H11 antibodies bind to EphA2 receptors expressed on HUVEC cells. The apparent dissociation constants ($K_D$) for the binding of 37.3D7, 37.1F5, and 53.2H11 antibodies with EphA2 on the surface of the cells were determined from the binding curves established with FACS binding assays performed at several concentrations and shown in FIG. 11. A value of $K_D$=0.3 nM for the 37.3D7 antibody was estimated by non-liner regression for one-site binding (FIG. 11), which is similar to the $K_D$ value of the binding of 37.3D7 antibody to human cancer cells. A value of $K_D$=0.01 nM for the 37.1F5 antibody and a value of $K_D$=0.06 nM for the 53.2H11 antibody were similarly obtained. This indicates that 37.3D7, 37.1F5 and 53.2H11 antibodies specifically bind to HUVEC cells through the EphA2 receptor.

Figure 12:
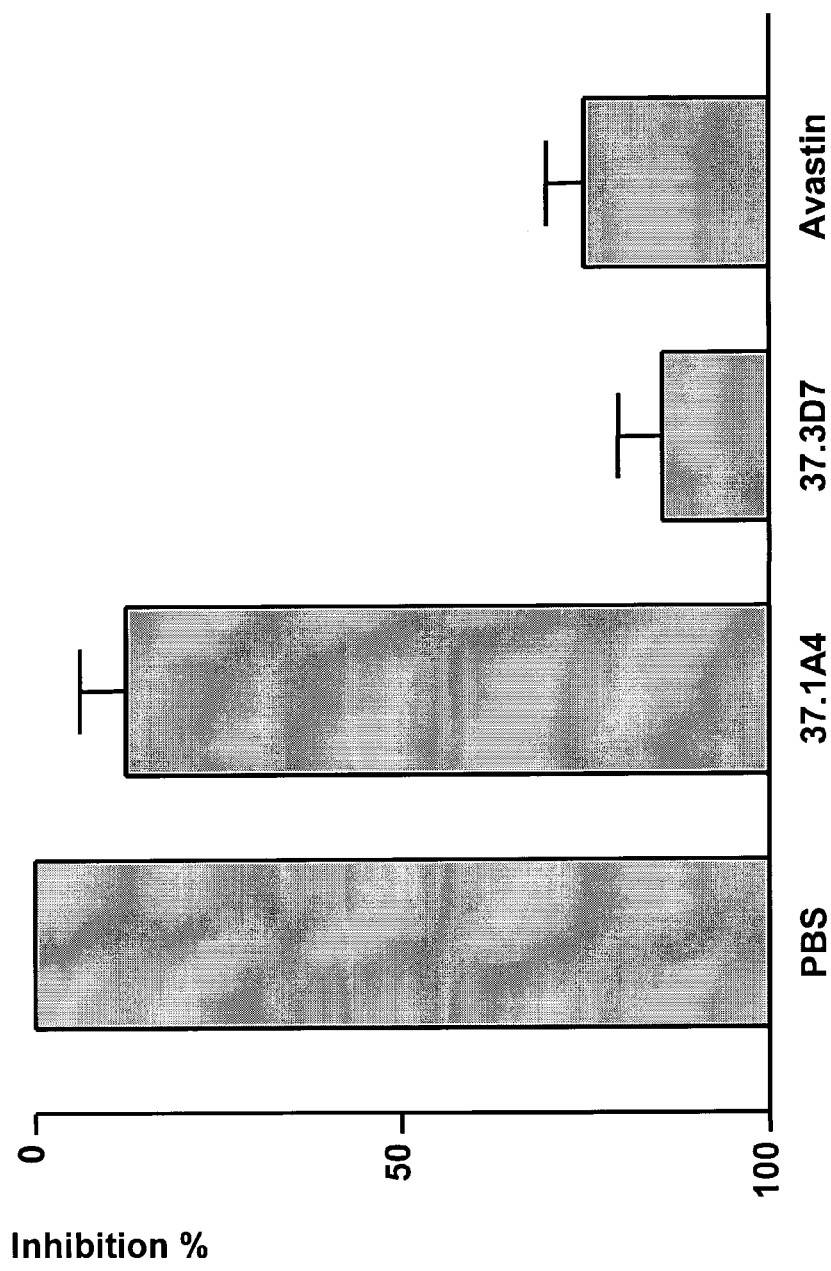
FIG. 12 shows the inhibition of VEGF-stimulated HUVEC cell growth and survival by 37.3D7 antibody.

The 37.3D7 antibody strongly inhibited VEGF-induced HUVEC growth and survival. The activity is similar or better than that of Avastin®, an anti-VEGF blocking antibody (Genentech) (FIG. 12). An agonistic anti-EphA2 antibody did not inhibit VEGF-induced HUVEC growth and survival (FIG. 12). In FIG. 12, HUVEC cells were grown in EBM-2 medium with serum and endothelial cell (EC) supplements (Clonetics) for 3 days. Cells were cultured in serum-free medium plus EC growth supplements lacking VEGF for 12-14 h. Following serum starvation, cells were stimulated with 5 ng/mL VEGF plus 0.4% serum with or without indicated antibodies (100 µg/mL). The effects of the antibodies on VEGF-induced HUVEC cell growth and survival was determined 3 days after addition of antibodies and VEGF using the MTT assay as described in Example 5. The percent inhibition of VEGF-mediated growth and survival by antibodies is shown in FIG. 12. $OD_{545}$ values for vehicle-treated samples were set to 0% inhibition and 100% inhibition was set using samples lacking VEGF.

That treatment of HUVEC cells with 37.3D7 antibody inhibits intracellular EphA2 receptor signaling was shown by measuring the inhibition of phosphorylation of its downstream effectors such as Akt.

Figure 13:
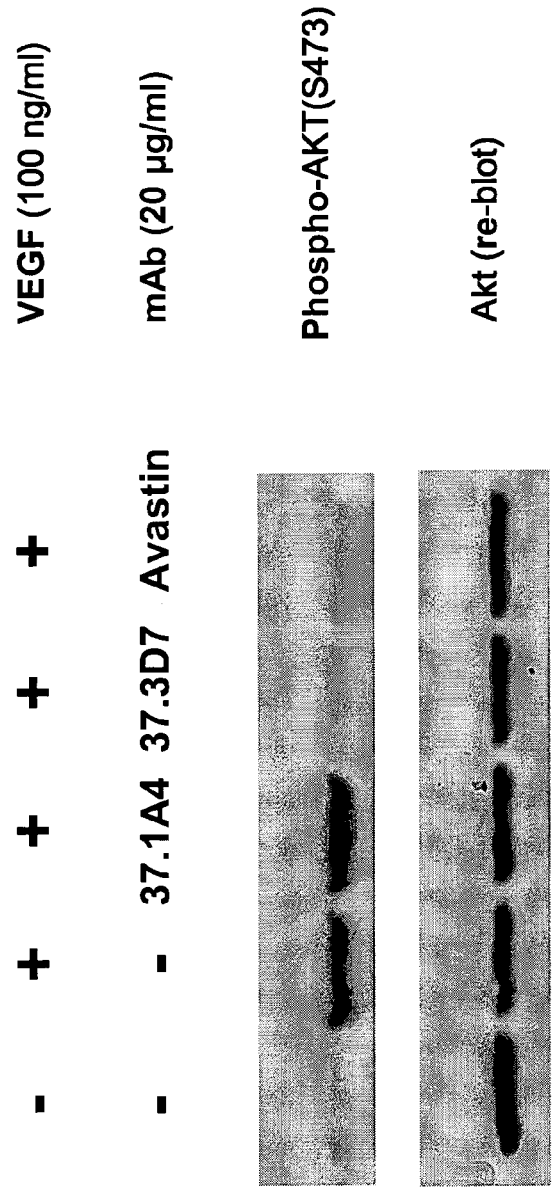
FIG. 13 shows the inhibition of VEGF-induced Akt phosphorylation by 37.3D7 antibody in HUVEC cells.

The inhibition is similar to that of Avastin®, an anti-VEGF blocking antibody (Genentech) (FIG. 13). agonistic anti-EphA2 antibody did not inhibit VEGF-induced Akt phosphorylation in HUVEC cells. In FIG. 13, HUVEC cell were starved for 12-14 h in serum-free medium plus EC supplements lacking VEGF. Cells were treated with antibodies (20 µg/mL) for 1 h before addition of VEGF (100 ng/mL). Cells were lysed 15 min after VEGF addition and immunoblots were probed with the indicated antibodies.

Example 7

Figure 14:
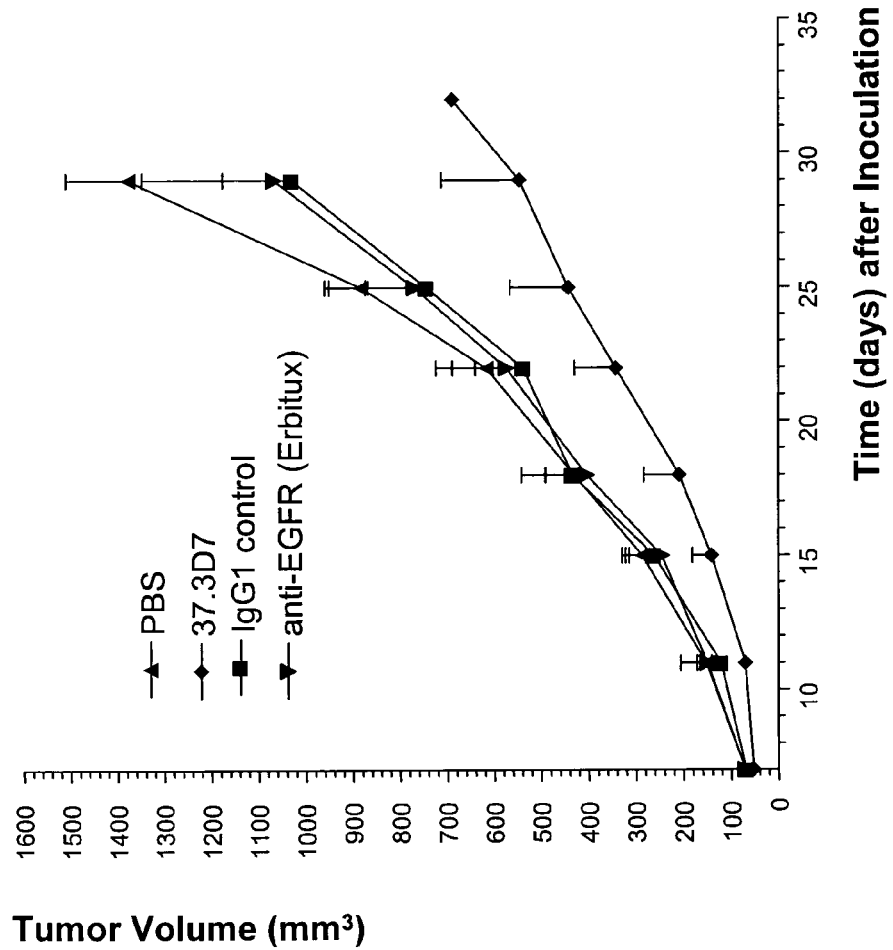
FIG. 14 shows the effect of the treatment with 37.3D7 antibody on the growth of HT-29 colon cancer xenograft in mice. The effect is compared with that of an anti-EGFR antibody and a non-binding control IgG1 antibody.

Suppression of Growth of Human Colon Cancer HT-29 Xenograft in Mice by 37.3D7 Antibody (FIG. 14)

Human colon cancer HT-29 xenografts were established in SCID mice by subcutaneous injection of $2 \times 10^6$ HT-29 cells. When the mice showed palpable (50 mm$^3$) HT-29 xenograft tumors, they were treated with 37.3D7 antibody or a control antibody (IgG$_1$) (1 mg/mouse, i. v., two times per week) or PBS alone (100 µL/mouse, i. v., two times per week). The growth of tumors was significantly slowed by 37.3D7 antibody treatment compared to a control antibody treatment or PBS alone. No toxicity of 37.3D7 antibody was observed, based on measurements of the weights of the mice.

Example 8

Inhibition of Early Mammary MDA-MB-231 Metastasis by the Anti-EphA2 Antibody hu53.2H11

Anti-tumor activity of the anti-EphA2 antibody hu532H11 was evaluated at one dose level against early mammary MDA-MB-231 tumor implanted subcutaneously in female SCID mice. The effect of this antibody on the MDA-MB-231 tumor invasion in the superficial axial and inguinal lymph nodes was also investigated. To do so, hu532H11 was administered at 40 mg/kg/adm by iv route, on days 1, 5, 8, 12, 15, 19, 22 and 26 post tumor implantation. Control group was left untreated.

For the evaluation of anti-tumor activity of hu532H11, animals were weighed daily and tumors were measured 2-3 times weekly by caliper. Tumor weights were calculated using the formula mass (mg)=[length (mm)×width (mm)$^2$]/2. Antitumor activity was evaluated according to 3 criteria: 1) including T/C, defined as median tumor weight (mg) of a treated group divided by median tumor weight of the non-treated control; 2) the determination of tumor growth delay (T-C), where T is defined as the median time in days required for treatment group tumors to reach 750 mg and C is the median time for the control group tumors to reach the same size, and 3) tumor cell kill is defined as log 10 cell kill (gross)=[T-C value in days]/(Td×3.32). T-C is defined above, and Td is the tumor volume doubling time in days of the control tumors, which is estimated from the best fit straight line from a log-linear growth plot of the control group tumors in exponential growth (100-1,000 mg range).

In a parallel study, animals were treated as described before, and on day 28 post tumor implantation all mice were sacrificed and axillary and inguinal lymph nodes were collected (median tumor size in the control group=1558 mg). The human Ki67 antibody was used in order to specifically identify MDA-MB-231 tumor cells in the lymph nodes by immunostaining. The surface area of metastases in lymph nodes was calculated (mean of 2 sections) as S=human Ki67 surface area×100/lymph node surface area.

Efficacy on primary tumor:
hu532H11 was well tolerated at 40 mg/kg/adm (total dose 320 mg/kg) with +8.9% body weight change on day 27. This dose delayed tumor growth of the primary tumor (T/C=27% and 1.0 log cell kill gross), even though the tumor escaped under therapy.

Anti-metastatic activity:
hu532H11 induced a reduction of metastases surface (>50%) in both axilliary and inguinal lymph nodes.

In conclusion in mice bearing mammary tumor MDA-MB-231, hu532H11 delays the growth of the primary tumor treated at an early stage of tumor development (T/C=27% and 1.0 log cell kill gross), and reduces the metastases surface (>50%) in both axillary and inguinal lymph nodes.

In another study, the activity of an anti-EphA2 antibody can be evaluated in the human colon HT29 liver "metastasis" model. The murine anti-EphA2 antibody 53.2H11 is administered iv, twice weekly, from day 4 post intrasplenic implantation of HT29 cells in SCID female mice (n=20 mice per group for non-tumor bearing animals (NTBA), treated and control). On day 50, 3 days post the 13$^{th}$ anti-EphA2 administration, the mice are necropsied and their spleen and liver are weighed in order to evaluate tumor mass either at the primary tumor site (spleen) or at site of metastasis (liver). Number of metastases is also evaluated. Data is analysed using the statistical tools known to the person skilled in the art.

Treatment with anti-EphA2 at 40 mg/kg/inj (total dose of 520 mg/kg) is well tolerated.

Primary tumor weight (spleen): A significant difference of spleen weight is observed between NTBA and control-implanted mice, the latter being bigger. There is no significant difference between spleen weight of control implanted mice and the one of anti-EphA2 treated mice.

Metastases weight (liver): the liver weight of control-implanted mice is significantly bigger than the liver weight of NTBA; on the other hand, it is significantly smaller in anti-EphA2 treated mice than in control-implanted mice.

Number of liver metastases: no statistical difference is observed between control implanted and anti-EphA2 treated mice.

In conclusion, intrasplenic implantation of human colic adenocarcinoma HT-29 significantly induces an increase in liver weight due to the metastatic tumor burden. Anti-EphA2 treatment is able to significantly decrease metastatic tumor burden as observed by the reduction of the liver weight of implanted mice without affecting the number of metastases counted on the liver.

Example 9

Cloning and Sequencing of the Light and Heavy Chains of 37.1F5 Antibody

RNA Preparation from Hybridoma Cells that Produces the 37.1F5 Antibody

Preparations of total RNA were obtained from $5\times10^6$ hybridoma cells, which produce 37.1F5 antibody, using Qiagen's RNeasy miniprep kit. Briefly, $5\times10^6$ cells were pelleted and resuspended in 350 µL RLT buffer (containing 1% β-mercaptoethanol). The suspension was homogenized by passing it through a 21.5 gauge needle and syringe roughly 10-20 times or until it was no longer viscous. Ethanol (350 µL of 70% aqueous ethanol) was added to the homogenate, which was mixed well. The solution was transferred to a spin column, placed in a 2-mL collection tube and spun at >8000×g for 15 seconds. The column was washed twice with 500 µL RPE buffer, then transferred to a fresh tube and eluted with 30 µL RNase free water and a 1-minute spin. The eluate (30 µL) was placed back on the column for a second 1-minute elution spin. An aliquot of the 30 µL eluate was diluted with water and used to measure the UV absorption at 260 nm for RNA quantitation.

cDNA Preparation with Reverse Transcriptase (RT) reaction

The variable region 37.1F5 antibody cDNA was generated from the total RNA using Invitrogen's SuperscriptII kit. The kit protocols were followed closely, utilizing up to 5 µg of total RNA from the Qianeasy mini preps. Briefly, the RNA, 1 µL random primers, and 1 µL dNTP mix were brought up to 12 µL with RNase free sterile distilled water and incubated at 65° C. for 5 minutes. The mix was then put on ice for at least 1 minute. Next 4 µL of 5× reaction buffer, 2 µL 0.1 M DTT, and 1 µL RNaseOUT were added and the mix was incubated at 25° C. for 2 minutes in an MJ Research thermalcycler. The thermalcycler was paused so that 1 µL of SuperscriptII enzyme could be added and then restarted for an additional 10 minutes at 25° C. before shifting to 55° C. for 50 minutes. The reaction was heat inactivated by heating to 70° C. for 15 min and the RNA was removed by adding 1 µL RNase H and incubating at 37° C. for 20 minutes.

Degenerate PCR Reactions

The procedure for the first round degenerate PCR reaction on the cDNA derived from hybridoma cells was based on methods described in Wang et al. (2000; *J Immunol Methods.*; 233(1-2):167-77) and Co et al. (1992; *J. Immunol.*; 148(4):1149-54). The primers for this round (Table 2) contain restriction sites to facilitate cloning into the pBluescriptII plasmids.

The PCR reaction components (Table 3) were mixed on ice in thin walled PCR tubes and then transferred to an MJ research thermalcycler preheated and paused at 94° C. The reactions were performed using a program derived from Wang et al. (2000; *J Immunol Methods.*; 233(1-2):167-77), as follows:

Name: Wang45
1) 94° C. 3:00 min
2) 94° C. 0:15 sec
3) 45° C. 1:00 min
4) 72° C. 2:00 min
5) Goto 2 29 times
6) 72° C. 6:00 min
7) 4° C. for ever
8) end The PCR reaction mixtures were then run on a 1% low melt agarose gel, the 300 to 400 by bands were excised, purified using Zymo DNA mini columns, and sent to Agencourt biosciences for sequencing. The respective 5' and 3' PCR primers were used as sequencing primers to generate the 37.1F5 variable region cDNAs from both directions.

Cloning the 5' End Sequence

Since the degenerate primers used to clone the 37.1F5 variable region light chain and heavy chain cDNA sequences alters the 5' end sequences, additional sequencing efforts were needed to decipher the complete sequences. The preliminary cDNA sequence from the methods described above were used to search the NCBI IgBlast site (http://www.ncbi.nlm.nih.gov/igblast/) for the murine germline sequences from which the 37.1F5 sequence is derived. PCR primers were designed (Table 4) to anneal to the leader sequence of the murine antibody so that a new PCR reaction could yield the complete variable region cDNA, unaltered by the PCR primers. The PCR reactions, band purifications, and sequencing were performed as described above. The germline sequences from which the light chain and heavy chain of mu37.1F5 are likely derived, are accessible under the Genbank accession numbers MUSIGKVR3 and AF303839, respectively.

Peptide Analysis for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine 37.1F5 antibody.

Table 5 gives the calculated mass from the cDNA sequences for 37.1F5 LC and HC together with the values measured by LC/MS. The molecular weight measurements are consistent with the cDNA sequences for both the 37.1F5 light and heavy chain.

Essentially the same method was used for cloning of the light and heavy chains of 37.3D7 and 53.2H11. The Genbank accession numbers of the germline sequences from which the light chain and of the heavy chain of 37.3D7 are likely derived, are respectively MMU231217 and AF303868. For 53.2H11, they are respectively MMU231196 and AF303833; for EphA2-N1, K02161 and J00488 respectively; and for EphA2-N2, AJ231222 and J00488 respectively.

Example 10

Inhibition of the Growth of EphA2 Expressing Tumor Cells by Humanized-37.3D7-SPDB-DM4 and Humanized-53.2H11-SPDB-DM4

Humanized 37.3D7 and humanized 53.2H11 antibodies were conjugated to L-DM4 $N^{2'}$deacetyl-$N^{2'}$(4-methyl-4-mercapto-1-oxopentyl)-maytansine using SPDB (4-[2-pyridyldithio]butanoic acidN-hydroxsuccinimde ester) linker. Briefly, the antibody was modified at 8 mg/mL with 5.5 or 6.5 folds molar excess of SPDB for hu53.2H11 and hu37.3D7 respectively. The reaction was carried out in Buffer A (50 mM $KP_i$/50 mM NaCl/2 mM EDTA, pH 6.5, 95% v/v) with EtOH (5% v/v) for 90 minutes at room temperature. The modified antibody was then purified by SephadexG25 desalting column with Buffer A. Next, the modified antibody was reacted with a 1.7-fold molar excess of DM4 over SPDB linker. The reaction was carried out at 2.5 mg/mL antibody in Buffer A (97% v/v) and DMA (dimethylacetamide, 3% v/v) at room temperature for 20 hours. The conjugate was purified by SephadexG25 desalting column with 10 mM Histidine, 130 mM Glycine, 5% sucrose, pH5.5. The drug to antibody ratio was 4.0 for hu37.3D7-SPDB-DM4 and 3.1 for hu53.2H11-SPDB-DM4.

The effects of hu37.3D7-SPDB-DM4 and hu53.2H11-SPDB-DM4 on the growth of EphA2 expressing tumor cells were first tested using the in vitro cell proliferation WST-8 ((2-(2-methoxy-4-nitrophenyl)-3-(4-nitrophenyl)-5-(2,4-disulfophenyl)-2H-tetrazolium, monosodium salt) assay (Catalog# CK04-11, Dojindo Molecular Technogies, Inc). Several human tumor cell lines were tested. Approximately 2000 cells/well were plated in a 96-well plate in regular medium (as suggested from ATCC for each cell line) with 10% serum in the presence of a variety of concentration of hu37.3D7-SPDB-DM4 or hu53.2H11-SPDB-DM4. The cells were then allowed to grow for 5 days. A solution of WST-8 [20 µL solution] was then added and the cells were returned to the incubator for 2-3 h. The absorbance of the plate was measured at 450 nm and 650 nm. Two control groups were used in the experiments. 0% survival is the medium only control. 100% survival is the cells only control. For data analysis, the A650 nm (reference wavelength) values were first subtracted from the corresponding A450 nm values. Then, A450 nm values of each sample were normalized by subtraction of A450 nm values of the background control (medium only). The survival fractions were calculated by the normalized A450 values of the samples dividied by the normalized A450 values from the cells only controls (100% survival –0% survival). Log [Ab-DM4] values were plotted on the x-axis and survival fractions were plotted on y-axis.

Figure 15A:
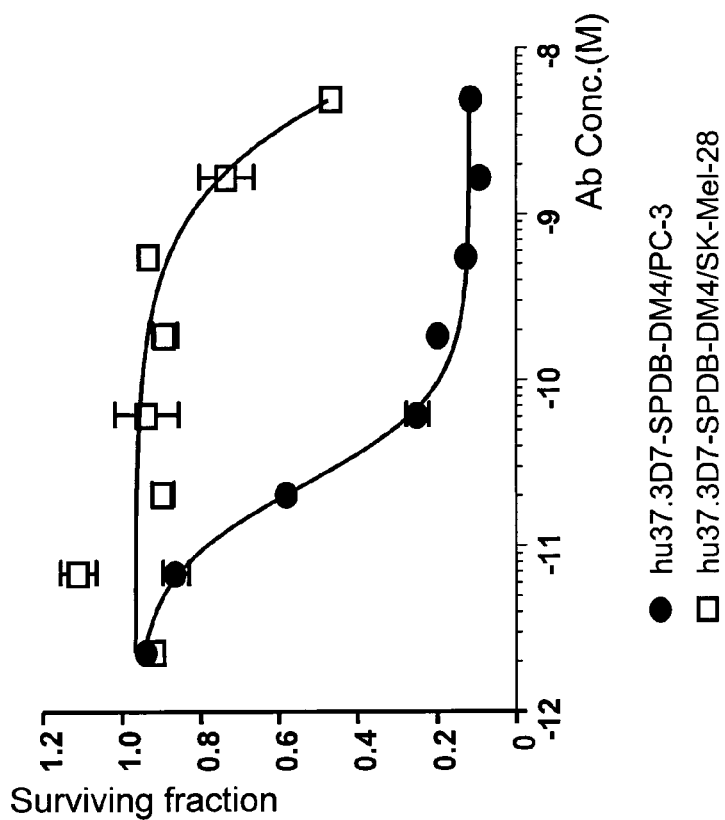
FIG. 15A shows the inhibition of the growth of PC3 prostate tumor cells by hu37.3D7-SPDB-DM4.
Figure 15B:
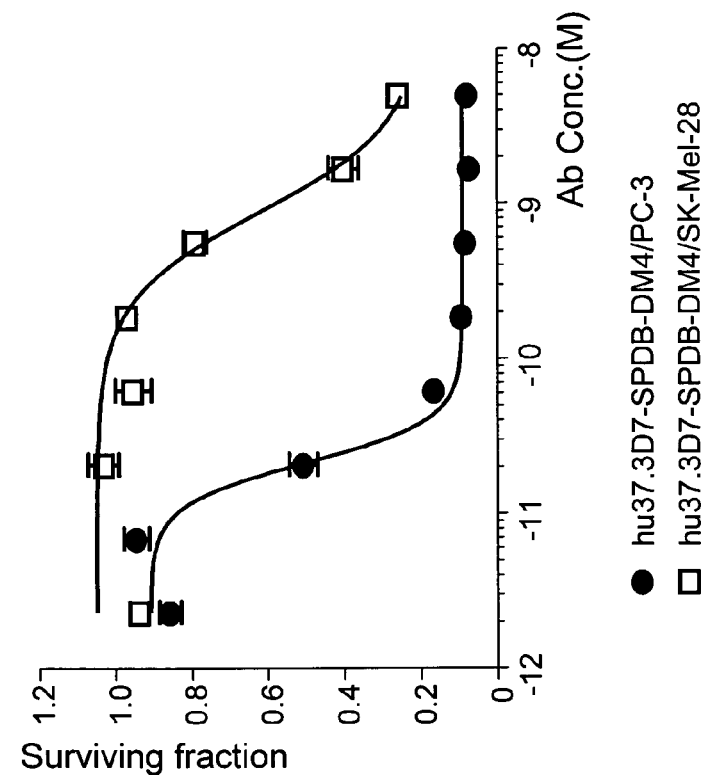
FIG. 15B shows the inhibition of the growth of PC3 prostate tumor cells by hu53.2H11-SPDB-DM4.

Hu37.3D7-SPDB-DM4 and hu53.2H11-SPDB-DM4 significantly inhibited the growth of EphA2 expressing human tumor cells, including PC3 prostate tumor cells, MDA-MDA-MB-231 breast tumor cells, WM-115 melanoma cells, A375 melanoma cells and LoVo colon tumor cells. As an example, the findings with the PC3 prostate tumor cells are shown. The hu37.3D7-SPDB-DM4 or hu53.2H11-SPDB-DM4 strongly inhibited the growth of PC3 cells in a dose-dependent manner with an similar $IC_{50}$ value of 0.02 nM (FIGS. 15A &15B). The potency of conjugates correlated with the EphA2 expression levels. More than 50-fold higher concentration of hu37.3D7-SPDB-DM4 or hu53.2H11-SPDB-DM4 was required to inhibit the growth of the SK-Mel28 cells ($IC_{50}$ values: 1.3 nM and >5 nM, respectively; FIGS. 15A & 15B), which expressed almost undetectable level of EphA2 on cell surface (measured by FACS data not shown) (FIGS. 15A &15B). Therefore, results of the in vitro growth inhibition assays demonstrated the ability of antagonist anti-EphA2 antibody-conjugates to specifically inhibit the growth of EphA2 expressing tumor cell lines.

Figure 16B:
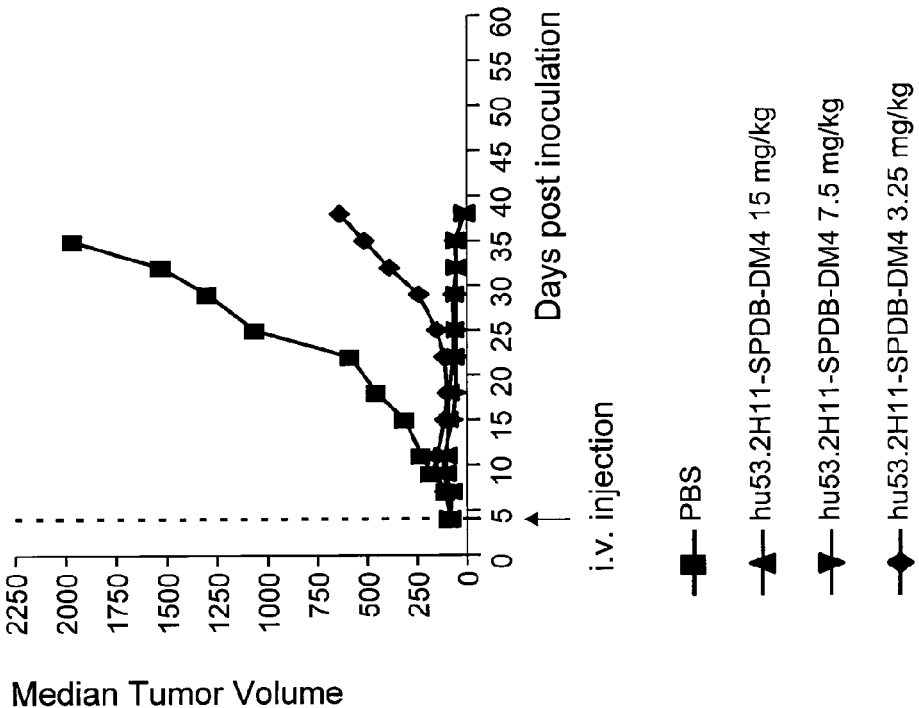
FIG. 16B shows the effect of the treatment with hu53.2H11-SPDB-DM4 on the growth of MDA-MB-231 breast tumor xenograft in mice.
Figure 16A:
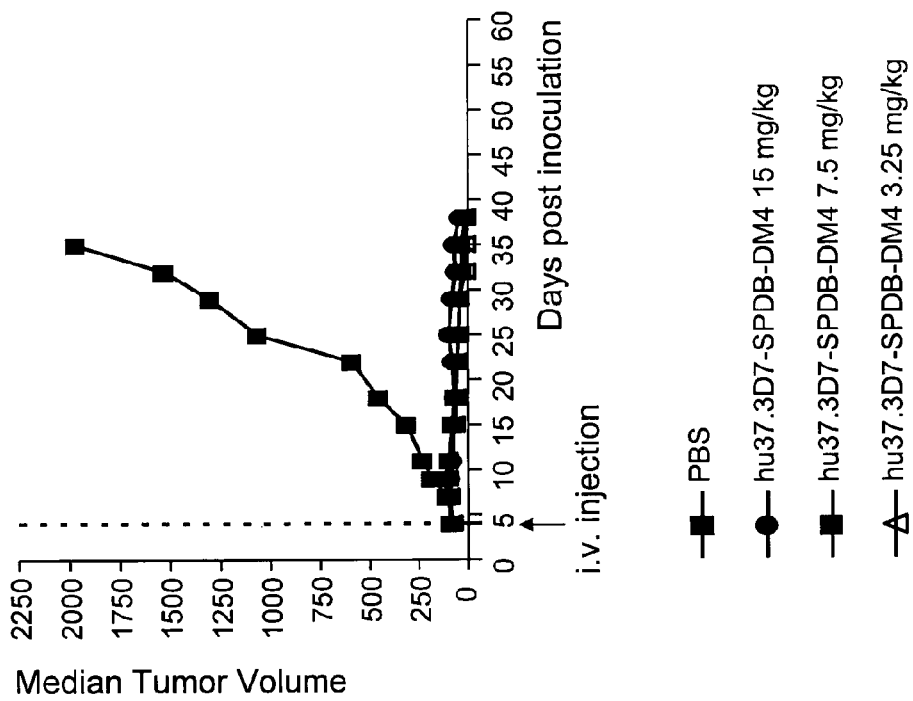
FIG. 16A shows the effect of the treatment with hu37.3D7-SPDB-DM4 on the growth of MDA-MB-231 breast tumor xenograft in mice.

The effects of hu37.3D7-SPDB-DM4 and hu53.2H11-SPDB-DM4 on the growth of EphA2 expressing tumor xenografts were tested. A study using MDA-MB-231 breast tumor xenograft model is shown as one example. Human breast cancer MDA-MB-231 xenografts were established in female CB17 SCID mice 5 weeks of age by subcutaneous injection of $1 \times 10^7$ MDA-MB-231 cells. When MDA-MB-231 xenograft tumors were established (average size of 83 $mm^3$), mice were treated with a single i. v injection of hu3D7-SPDB-DM4 or hu2H11-SPDB-DM4 or PBS. The doses of antibodies were 15 mg/kg of mouse body weight, 7.5 mg/kg of mouse body weight and 3.25 mg/kg of mouse body weight. The growths of MDA-MB-231 tumors were completely inhibited by either hu3D7-SPDB-DM4 or hu2H11-SPDB-DM4 antibody-conjugates at all of the tested concentrations except at 3.25 mg/kg of hu2H11-SPDB-DM4, which shows marked delay of tumor cell growth relative to PBS control (FIGS. 16A &16B). The median tumor volumes in each group (6 mice per group) are shown in the FIGS. 16A & B. In summary, both hu3D7-SPDB-DM4 and hu2H11-SPDB-DM4 have potent growth inhibitory activities on EphA2 expressing tumors in vivo. No toxicities of both antibody-conjugates were observed, based on the body weight measurements.

Tables

TABLE 1A

The mu37.3D7 light chain framework surface residues and corresponding residues at the same Kabat position in the human 28E4 antibody.
mu37.3D7 Light Chain Framework Surface Residues And Corresponding Residues In The Human 28E4 Antibody

| Kabat Position | mu37.3D7 | 28E4 |
|---|---|---|
| 1 | Q | E |
| 3 | V | V |
| 5 | T | T |
| 9 | A | A |
| 10 | I | T |
| 15 | L | P |
| 18 | R | R |
| 40 | P | P |
| 41 | G | G |
| 57 | G | G |
| 60 | A | A |
| 67 | S | S |
| 80 | S | S |
| 81 | E | E |
| 100 | S | G |
| 107 | K | K |
| 108 | R | R |

The residues that are different and therefore changed in the hu37.3D7 antibody are in grayed boxes.

TABLE 1B

The mu37.3D7 heavy chain framework surface residues and corresponding residues at the same Kabat position in the human 28E4 antibody.
mu37.3D7 Heavy Chain Framework Surface Residues And Corresponding Residues In The Human 28E4 Antibody

| Kabat Position | mu37.3D7 | 28$^E$4 |
| --- | --- | --- |
| 1 | Q | Q |
| 3 | Q | Q |
| 5 | Q | V |
| 9 | S | A |
| 11 | L | V |
| 13 | R | K |
| 14 | P | P |
| 15 | G | G |
| 19 | Q | K |
| 23 | K | K |
| 28* | S* | N* |
| 41 | P | P |
| 42 | G | G |
| 43 | Q | Q |
| 61 | E | Q |
| 62 | K | K |
| 64 | M | Q |
| 65 | N | G |
| 73 | T | T |
| 74* | Y* | S* |
| 75 | S | T |
| 82B | S | S |
| 84 | S | S |
| 85 | E | E |
| 105 | Q | Q |
| 112 | S | S |

The residues that are different and therefore changed in the hu37.3D7 antibody are in grayed boxes.
The starred (*) residues are back mutated to the mu37.3D7 residue in one or more hu37.3D7 variants.

TABLE 2

Primers used for the degenerate PCR reactions are based on those in Wang et al., 2000 except HindKL (SEQ ID NO: 58) which is based on Co et al. 1992. Mixed bases are defined as follows: H = A + T + C, S = g + C, Y = C + T, K = G + T, M = A + C, R = A + g, W = A + T, V = A + C + G.

| Primer | Sequence |
| --- | --- |
| BamIgG1 (SEQ ID NO: 53) | GGAGGATCCATAGACAGATGGGGGTGTCGTTTTGGC |
| IgG2Abam (SEQ ID NO: 54) | GGAGGATCCCTTGACCAGGCATCCTAGAGTCA |
| EcoMH1 (SEQ ID NO: 55) | CTTCCGGAATTCSARGTNMAGCTGSAGSAGTC |
| EcoMH2 (SEQ ID NO: 56) | CTTCCGGAATTCSARGTNMAGCTGSAGSAGTCWGG |
| SacIMK (SEQ ID NO: 57) | GGAGCTCGAYATTGTGMTSACMCARWCTMCA |
| HindKL (SEQ ID NO: 58) | TATAGAGCTCAAGCTTGGATGGTGGGAAGATGGATACAGTTGGTGC |

TABLE 3

The light and heavy chain PCR reaction mixes for cloning of the 37.1F5 variable region cDNA sequences.

| Light Chain Reaction Mix | | Heavy Chain Reaction Mix | |
| --- | --- | --- | --- |
| 5 µl | 10 × PCR reaction buffer (Roche) | 5 µl | 10 × PCR reaction buffer (Roche) |
| 4 µl | 10 mM dNTP mix (2.5 mM each) | 4 µl | 10 mM dNTP mix (2.5 mM each) |
| 2 µl | Template (RT reaction) | 2 µl | Template (RT reaction) |
| 5 µl | 10 µM Sac1MK left primer | 2.5 µl | 10 µM EcoMH1 left primer |
| 5 µl | 10 µM HindKL right primer | 2.5 µl | 10 µM EcoMH2 left primer |
| 5 µl | DMSO | 5 µl | 10 µM BamIgG1 right primer |
| 0.5 µl | Taq Polymerase (Roche) | 5 µl | DMSO |
| 23.5 µl | sterile distilled H$_2$O | 0.5 µl | Taq Polymerase (Roche) |
| | | 23.5 µl | sterile distilled H$_2$O |
| 50 µl | Total | 50 µl | Total |

TABLE 4

The 5'end murine leader sequence primers used for the 37.1F5 second round PCR reactions. The 3'end primers are identical to those used in the first round reactions since they prime to the respective constant region sequences.

| Primer | Sequence |
| --- | --- |
| Light Chain 38SB13 LC Leader (SEQ ID NO: 59) | GACAGACACACTCCTGCTATGGG |
| Heavy Chain 5F85 HC Leader (SEQ ID NO: 60) | GCAGAATTCATGGGATGGAGCYGGATCTTTCT |

TABLE 5

The cDNA calculated and LC/MS measured molecular weights of the murine 37.1 F5 antibody light and heavy chains.

| | Light Chain | | | Heavy Chain | | |
| --- | --- | --- | --- | --- | --- | --- |
| | cDNA | LC/MS | Difference | cDNA | LC/MS | Difference |
| 37.1 F5 | 24031 Da | 24029 Da | 2 Da | 49316 Da | 49333 Da | 17 Da |

The invention claimed is:

1. A method for treating or inhibiting progression of cancer in a patient in need thereof, comprising administering an isolated antibody or an epitope-binding fragment or conjugate thereof that specifically binds to an EphA2 receptor to the patient, wherein the isolated antibody or epitope-binding fragment or conjugate thereof comprises a light chain variable region having at least 90% sequence identity to an amino acid sequence selected from the group consisting of SEQ ID NOS: 47, 48, 49, 50, and 52, and a heavy chain variable region having at least 90% sequence identity to an amino acid sequence selected from the group consisting of SEQ ID NOS: 32, 34, 36, 37, 38, 40, 42, 43, and 45, thereby treating or inhibiting progression of the cancer in the patient.

2. The method of claim 1, wherein the antibody, conjugate or epitope-binding fragment is an antagonist of said receptor.

3. The method of claim 1, wherein the cancer is metastatic.

4. The method of claim 1, wherein said antibody inhibits tumor neovascularization.

5. The method of claim 1, wherein the cancer is selected from breast cancer, colon cancer, endometrial cancer, ovarian carcinoma, osterosarcoma, cervical cancer, kidney cancer, prostate cancer, lung cancer, synovial carcinoma, pancreatic cancer, a sarcoma, glioma, head and neck cancer, gastric cancer, liver cancer, and other carcinomas.

6. The method of claim 1, wherein the antibody is a monoclonal antibody.

7. The method of claim 1, wherein the epitope-binding fragment is a Fab, Fab', F(ab')2, or Fv fragment.

8. The method of claim 1, wherein the antibody is a humanized or resurfaced antibody.

9. The method of claim 8, wherein the humanized or resurfaced antibody comprises a light chain variable region having an amino acid sequence with at least 95% sequence homology to the amino acid sequence comprising SEQ ID NO: 47.

10. The method of claim 9, wherein the humanized or resurfaced antibody comprises a heavy chain variable region having an amino acid sequence with at least 95% sequence homology to an amino acid sequence selected from the group consisting of SEQ ID NOs: 32, 34, and 36.

11. The method of claim 9, wherein the humanized or resurfaced antibody comprises a heavy chain variable region having an amino acid sequence with at least 98% sequence homology to the amino acid sequence comprising SEQ ID NO: 32.

12. The method of claim 9, wherein the humanized or resurfaced antibody comprises a heavy chain variable region having an amino acid sequence with at least 98% sequence homology to the amino acid sequence comprising SEQ ID NO: 34.

13. The method of claim 9, wherein the humanized or resurfaced antibody comprises a heavy chain variable region having an amino acid sequence with at least 98% sequence homology to the amino acid sequence comprising SEQ ID NO: 36.

14. The method of claim 8, wherein said humanized or resurfaced antibody comprises a light chain variable region having an amino acid sequence with at least 95% sequence homology to an amino acid sequence selected from the group consisting of SEQ ID NOs: 48, 49, and 50.

15. The method of claim 14, wherein the humanized or resurfaced antibody comprises a heavy chain variable region having an amino acid sequence with at least 95% sequence homology to an amino acid sequence selected from the group consisting of SEQ ID NOs: 37 and 38.

16. The method of claim 14, wherein the humanized or resurfaced antibody comprises a heavy chain variable region having an amino acid sequence with at least 98% sequence homology to the amino acid sequence of SEQ ID NO: 37.

17. The method of claim 14, wherein the humanized or resurfaced antibody comprises a heavy chain variable region having an amino acid sequence with at least 98% sequence homology to the amino acid sequence of SEQ ID NO: 38.

18. The method of claim 8, wherein the humanized or resurfaced antibody comprises a light chain variable region with at least 95% sequence homology to an amino acid sequence having the amino acid sequence of SEQ ID NO: 52.

19. The method of claim 18, wherein the humanized or resurfaced antibody comprises a heavy chain variable region with at least 95% sequence homology to an amino acid sequence having an amino acid sequence selected from the group consisting of SEQ ID NOs: 40, 42, 43, and 45.

20. The method of claim 18, wherein the humanized or resurfaced antibody comprises a heavy chain variable region with at least 98% sequence homology to an amino acid sequence having the amino acid sequence of SEQ ID NO: 40.

21. The method of claim 18, wherein the humanized or resurfaced antibody comprises a heavy chain variable region with at least 98% sequence homology to an amino acid sequence having the amino acid sequence of SEQ ID NO: 42.

22. The method of claim 18, wherein the humanized or resurfaced antibody comprises a heavy chain variable region with at least 98% sequence homology to an amino acid sequence having the amino acid sequence of SEQ ID NO: 43.

23. The method of claim 18, wherein the humanized or resurfaced antibody comprises a heavy chain variable region with at least 98% sequence homology to an amino acid sequence having the amino acid sequence of SEQ ID NO: 45.

24. The method of claim 1, wherein the conjugate comprises an antibody or an epitope-binding fragment thereof that specifically binds to an EphA2 receptor linked to a cytotoxic agent, thereby treating or inhibiting progression of the cancer in the patient.

25. The method of claim 24, wherein said cytotoxic agent is selected from the group consisting of a maytansinoid, a small drug, a tomaymycin derivative, a leptomycin derivative, a prodrug, a taxoid, CC-1065 and a CC-1065 analog.

26. The method of claim 25, wherein said cytotoxic agent is the maytansine DM1 of formula:

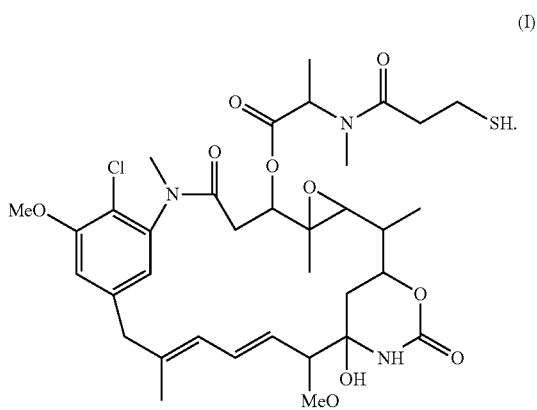 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

(I)

27. The method of claim 25, wherein said cytotoxic agent is the maytansine DM4 of formula:

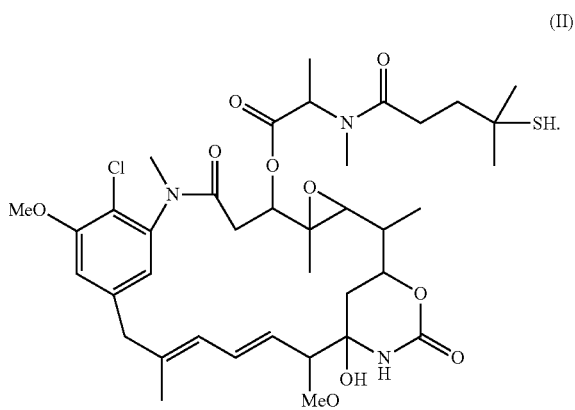 [SMILES: COc1cc2cc(c1Cl)N(C)C(=O)CC(OC(=O)C(C)N(C)C(=O)CCC(C)(C)S)C1(C)OC1C(C)C1CC(O)(NC(=O)O1)C(OC)/C=C/C=C(\C)C2]

(II)

28. The method of claim 25, wherein said cytotoxic agent is a tomaymycin derivative selected from the group consisting of:
- 8,8'-[1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[5-methoxy-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[4-(3-tert-butoxycarbonylaminopropyloxy)-2,6-pyridinediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[5-(3-aminopropyloxy)-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one];
- 8,8'-[5-(N-methyl-3-tert-butoxycarbonylaminopropyl)-1,3-benzenediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one];
- 8,8'-{5-[3-(4-methyl-4-methyldisulfanyl-pentanoylamino)propyloxy]-1,3-benzenediylbis(methyleneoxy)}-bis[(S)-2-eth-(E)-ylidene-7-methoxy-1,2,3,11a-tetrahydro-5H-pyrrolo[2,1-c][1,4]benzodiazepin-5-one];
- 8,8'-[5-acetylthiomethyl-1,3-benzenediylbis(methyleneoxy)]-bis[(S)-2-methylene-7-methoxy-1,2,3,11a-tetrahydro-5H-pyrrolo[2,1-c][1,4]benzodiazepin-5-one];
- bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester;
- 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one];
- 8,8'-[5-(N-4-mercapto-4,4-dimethylbutanoyl)amino-1,3-benzenediylbis(methyleneoxy)]-bis[7-methoxy-2-methylene-1,2,3,11a-tetrahydro-5H-pyrrolo[2,1-c][1,4]benzodiazepin-5-one];
- 8,8'-[5-(N-4-methyldithio-4,4-dimethylbutanoyl)-amino-1,3-benzenediylbis(methyleneoxy)]-bis[7-methoxy-2-methylene-1,2,3,11a-tetrahydro-5H-pyrrolo[2,1-c][1,4]benzodiazepin-5-one];
- 8,8'-[5-(N-methyl-N-(2-mercapto-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one];
- 8,8'-[5-(N-methyl-N-(2-methyldithio-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one];
- 8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];
- 8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one];
- 8,8'-[(4-(3-(4-methyl-4-methyldisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];
- 8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];
- 8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];
- 8,8'-[(1-(3-[4-(4-methyl-4-methyldisulfanyl-pentanoyl)-piperazin-1-yl]-propyl)-benzene-3,5-dimethyl)-dioxy]- bis[(S)-2-eth-(E)-ylidene-7-dimethoxy-1,2,3,11a-tetrahydro-pyrrolo[2,1-c][1,4]benzodiazepin-5-one];

8,8'-[(4-(2-{2-[2-(4-methyl-4-methyldisulfanyl-pentanoylamino)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];

8,8'-[(1-(2-{2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one];

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one];

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one];

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one];

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]; and 8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]; and 8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one].

29. The method of claim 25, wherein the cytotoxic agent is a leptomycin derivative selected from the group consisting of:

(2-Methylsulfanyl-ethyl)-amid of (2E,10E,12E,16Z,18E)-(R)-6-Hydroxy-3,5,7,9,11,15,17-heptamethyl-19-((2S,3S)-3-6-oxo-3,6-dihydro-2H-pyran-2-yl)-8-oxo-nonadeca-2,10,12,16,18-pentaenoic acid (2-methylsulfanyl-ethyl)-amid;

Bis-[(2-mercaptoethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid];

(2-Mercapto-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid;

(2-Methyldisulfanyl-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid;

(2-Methyl-2-methyldisulfanyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid; and (2-Mercapto-2-methyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid.

\* \* \* \* \*